(12) United States Patent
Ohlmeyer et al.

(10) Patent No.: US 9,937,180 B2
(45) Date of Patent: Apr. 10, 2018

(54) CONSTRAINED TRICYCLIC SULFONAMIDES

(71) Applicant: ICAHN SCHOOL OF MEDICINE AT MOUNT SINAI, New York, NY (US)

(72) Inventors: Michael Ohlmeyer, Plainsboro, NJ (US); David Kastrinsky, Fair Lawn, NJ (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 0 days.

(21) Appl. No.: 15/124,888

(22) PCT Filed: Mar. 10, 2015

(86) PCT No.: PCT/US2015/019764
§ 371 (c)(1),
(2) Date: Sep. 9, 2016

(87) PCT Pub. No.: WO2015/138496
PCT Pub. Date: Sep. 17, 2015

(65) Prior Publication Data
US 2017/0015630 A1    Jan. 19, 2017

Related U.S. Application Data

(60) Provisional application No. 61/951,186, filed on Mar. 11, 2014.

(51) Int. Cl.
| | |
|---|---|
| *A61K 31/517* | (2006.01) |
| *A61K 31/55* | (2006.01) |
| *A61K 31/18* | (2006.01) |
| *A61K 31/5415* | (2006.01) |
| *C07D 223/26* | (2006.01) |
| *C07D 223/32* | (2006.01) |
| *C07C 311/29* | (2006.01) |
| *C07D 279/36* | (2006.01) |
| *A61K 31/5377* | (2006.01) |
| *C07D 223/28* | (2006.01) |
| *C07D 279/26* | (2006.01) |

(52) U.S. Cl.
CPC ........ *A61K 31/517* (2013.01); *A61K 31/18* (2013.01); *A61K 31/5377* (2013.01); *A61K 31/5415* (2013.01); *A61K 31/55* (2013.01); *C07C 311/29* (2013.01); *C07D 223/26* (2013.01); *C07D 223/32* (2013.01); *C07D 279/36* (2013.01); *C07C 2601/08* (2017.05); *C07C 2601/14* (2017.05); *C07C 2603/32* (2017.05); *C07D 223/28* (2013.01); *C07D 279/26* (2013.01)

(58) Field of Classification Search
CPC ....... A61K 31/18; A61K 31/517; A61K 31/55
USPC ........................................................ 514/217
See application file for complete search history.

(56) References Cited

U.S. PATENT DOCUMENTS

| | | | |
|---|---|---|---|
| 4,634,766 A | 1/1987 | Atkinson et al. | |
| 4,668,671 A | 5/1987 | Gribble et al. | |
| 4,882,351 A | 11/1989 | Oshima et al. | |
| 6,583,138 B1 | 6/2003 | Miyamoto et al. | |
| 9,540,358 B2 | 1/2017 | Ohlmeyer et al. | |
| 2002/0103189 A1 | 8/2002 | Miyamoto et al. | |
| 2008/0275023 A1 | 11/2008 | Guidi et al. | |
| 2015/0376191 A1 | 12/2015 | Ohlmeyer et al. | |
| 2017/0015625 A1 | 1/2017 | Ohlmeyer et al. | |

FOREIGN PATENT DOCUMENTS

| | | | |
|---|---|---|---|
| CN | 102942562 A | 2/2013 | |
| EP | 0679641 A1 | 11/1995 | |
| EP | 0881220 A1 | 12/1998 | |
| WO | 2004052847 A2 | 6/2004 | |
| WO | 2006116157 A2 | 11/2006 | |
| WO | 2006117183 A1 | 11/2006 | |
| WO | 2013025882 A2 | 2/2013 | |
| WO | WO2013025882 A2 * | 2/2013 | .......... C07D 417/04 |

(Continued)

OTHER PUBLICATIONS

Zhang et al, "Akt, FoxO and regulation of apoptosis," Biochimica et Biophysica Acta, 2011, vol. 1813, pp. 1978-1986.*
Extended EP Search Report for EP 12823881.3 dated Mar. 3, 2015.
International Search Report for PCT/US2012/051097 dated Feb. 20, 2013.
Alfredsson et al., "Mass Fragmentographic Analysis of Clomipramine and Its Mono-Demethylated Metabolite in Human Plasma" Psychopharmacology, 52, 25-30 (1977).
Midgley et al., "Synthesis of [13C$_2$]-Amitriptyline, Nortriptyline and Desmethynortriptyline" Journal of Labelled Compounds and Radiopharmaceuticals, vol. XV, pp. 511-521 (1978).
Hadrich et al., "Synthesis and Characterization of Fluorescent Ligands for the Norepinephrine Transporter: Potential Neuroblastoma Imaging Agents", J. Med. Chem., 1999, (published on web Jul. 16, 1999).

(Continued)

*Primary Examiner* — Kathrien A Cruz
*Assistant Examiner* — Janet L. Coppins
(74) *Attorney, Agent, or Firm* — Heslin Rothenberg Farley & Mesiti P.C.

(57) ABSTRACT

Tricyclic chemical modulators of protein phosphatase 2A are disclosed. The compounds are useful to treat cancer, age-onset proteotoxicity, stress-induced depression, inflammation, and acne. The compounds are of the following phenothiazine and dibenzoazepine compounds and similar genera:

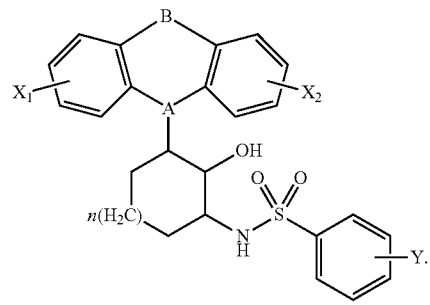

18 Claims, No Drawings

(56) References Cited

FOREIGN PATENT DOCUMENTS

| WO | 2014031986 A1 | 2/2014 |
|---|---|---|
| WO | 2014130534 A1 | 8/2014 |
| WO | 2015138500 A1 | 9/2015 |
| WO | 2017/024229 A1 | 2/2017 |
| WO | 2017/044567 A1 | 3/2017 |
| WO | 2017/044569 A1 | 3/2017 |
| WO | 2017/044571 A1 | 3/2017 |
| WO | 2017/044572 A1 | 3/2017 |
| WO | 2017/044575 A1 | 3/2017 |

OTHER PUBLICATIONS

Runyon et al., "Influence of Chain Length and N-Alkylation on the Selective Serotonin Receptor Ligand 9-(Aminomethyl)-9,10-dihydroanthracene", Bioorganic & Medicinal Chemistry Letters 11 (2001), 655-658.

Van Dort et al., Synthesis of $^{11}$C-Labeled Desipramine and its Metabolite 2-Hydroxydesipramine: Potential Radiotracers for PET Studies of the Norepinephrine Transporter, Nuclear Medicine & Biology, vol. 24, pp. 707-711, 1997.

Ilies et al., "Protease Inhibitors: Synthesis of Bacterial Collagenase and Matrix Metalloproteinase Inhibitors Incorporating Arylsulfonylureido and 5-Dibenzo-suberenyl/subelyl Moieties", Bioorganic & Medicinal Chemistry, 11 (2003) 2227-2239.

Yang et al., "Catalytic decarboxylative alkylationof B -keto acids with sulfonamides via the cleavage of carbon-nitrogen and carbon-carbon bonds," Chemical Communications, 2011 (published on Web: Jun. 22, 2011), vol. 47, No. 29, pp. 8343-8345.

Azuine et al., "Cancer chemopreventive effect of phenothiazines and related tri-heterocyclic analogues in the 12-0-tetradecanoylphorbol-13-acetate promoted Epstein-Barr virus early antigen activation and the mouse skin two-stage carcinogenes is models," Pharmacological Research, 2004, vol. 49, No. 2, pp. 161-169.

Ohshima, et al., "Non-Prostanoid Thromboxane $A_2$ Receptor Antagonists with a Dibenzoxepin Ring System. 2" J. Med. Chem, 1992, 35, 3402-3413.

Morak-Mlodawska et al., "Acyl and Sulfonyl Derivatives of 10-Aminoalkyl-2,7-Diazaphenothiazines#, Hetrocycles", vol. 78, No. 5, 2009.

Alfonso et al., "Synthesis of a $C_{11}$ Spiropiperdino derivative of 8-Chloro-6,11-dihydro 5H—Benzo [5,6] cyclohepta[1,2-b]pyridine", Tetrahedron Letters 39, 1998, 7661-7664.

Kau et al., A chemical genetic screen identifies inhibitors of regulated nuclear export of a Forkhead transcription factor in PTEN-deficient tumor cells, Cancer Cell, XP008037524, Dec. 2003.

Jelen et al., "Synthesis of 6-Aminoalkyldiquino-1,4-Thiazines and Their Acyl and Sulfonyl Derivatives, Heterocycles", vol. 4, No. 4, XP055279565, 2008.

Pluta et al., "Anticancer activity of newly synthesized azaphenothiazines from NCI's anticancer screening bank#", Pharmaceutical Reports, 2010, 62, 319-332.

Motohashi et al., "Synthesis and Biological Activity of N-acylphenothiazines" International Journal of Antimicrobial Agents, 2000, pp. 203-207, vol. 14.

Database PubChemCompound, "N-[4-methoxy-3-(3-phenothiazin-10-ylpropylsulfamoyl)phenyl]acetamide," URL: http://pubchem.ncbi.nlm.nih.gov/search/search.cgi, 2005-2009.

RN 1350122-38-1 CAS Registry.

International Search Report for PCT/US2014/017127 dated May 20, 2014.

International Search Report for PCT/US2015/019770 dated May 8, 2015.

International Search Report for PCT/US2016/050685 dated Oct. 18, 2016.

International Search Report for PCT/US2016/050688 dated Oct. 18, 2016.

International Search Report for PCT/US2016/045779 dated Sep. 30, 2016.

International Search Report for PCT/US2016/050690 dated Oct. 18, 2016.

International Search Report for PCT/US2016/050696 dated Oct. 18, 2016.

International Search Report for PCT/US2016/050692 dated Oct. 18, 2016.

O'Brien et al., "cis- and trans-Stereoselective Epoxidation of N-protected 2-Cyclohexen-1-ylamines," Organic Letters, 2003, 14(23), 6012-6015.

International Search Report and Written Opinion issued in PCT/US2015/019764, dated May 8, 2015.

* cited by examiner

CONSTRAINED TRICYCLIC SULFONAMIDES

CROSS REFERENCE TO RELATED APPLICATIONS

This application is a U.S. National Phase filing under 35 U.S.C. § 371 of International Application PCT/US2015/019764, filed Mar. 10, 2015, and published as WO 2015/138496 on Sep. 17, 2015. PCT/US2015/019764 claims priority of U.S. provisional application 61/951,186, filed Mar. 11, 2014. The entire contents of each of the prior applications are incorporated herein by reference.

FIELD OF THE INVENTION

The invention relates to the use of tricyclic chemical modulators of PPA2 and FOXO transcription factor proteins to treat cancer, proteotoxicity induced neurodegeneration, stress-induced depression, inflammation, acne, and viral infections.

BACKGROUND

Protein kinases have gained acceptance as therapeutic targets and have become a major focus of drug development efforts in oncology, with hundreds of inhibitors either in the pipeline or already in the clinic. Protein phosphatases, on the other hand, have been largely ignored for drug development because of their reputed lack of substrate specificity and the toxicity associated with natural products discovered as potent active site inhibitors. In contrast to the narrow substrate specificity of protein kinases, PP2A interacts with multiple substrates, and therefore its activation is, in effect, a combination therapy that coordinately inhibits multiple signaling pathways, including oncogenic signaling pathways. Protein phosphatase 2A (PP2A), composed of ABC subunits, dephosphorylates key oncogenic signaling proteins to function as a tumor suppressor.

Protein phosphatase 2A is one of the four major serine threonine phosphatases and is implicated in the negative control of cell growth and division. Protein phosphatase 2A holoenzymes are heterotrimeric proteins composed of a structural subunit A, a catalytic subunit C, and a regulatory subunit B. The PP2A heterotrimeric protein phosphatase is a ubiquitous and conserved phosphatase with broad substrate specificity and diverse cellular functions. Among the targets of PP2A are proteins of various signaling cascades, such as Raf, MEK, AKT, ERK, and FOXO.

PP2A interacts directly with FOXO1 and dephosphorylates FOXO1. Inhibition of PP2A phosphatases rescues FOXO1-mediated cell death by regulating the level of the pro-apoptotic protein BIM. In addition, PP2A directly regulates FOXO3a subcellular localization and transcriptional activation. Without wishing to be held to any particular theory, it may be that the compounds described herein promote apoptosis by acting on FOXO transcription factors via activation of PP2A.

The FOXO (Forkhead transcription factors, Class O) proteins are a group of transcription factors involved in control of a variety of physiological, metabolic and developmental pathways. They are downstream effectors in a number of signaling pathways including insulin and growth factor signaling; they are also regulated by oxidative stress and nutrient deprivation. Cellular processes affected by FOXO activity include cell cycle control, differentiation, proliferation and apoptosis. Disregulation of FOXO mediated processes has been implicated in a number of pathologies including tumorigenesis, inflammation, diabetes and neurodegenerative conditions amongst others. Activity of FOXO transcription factors are controlled in part by their sub-cellular localization, in particular their localization to the nucleus from the cytosol, and their subsequent transcriptional activation.

Four FOXO proteins designated FOXO1, FOXO3a, FOXO4 and FOXO6 are present in human cells and their activity is controlled by a variety of mechanisms including stability (proteolytic cleavage), sub-cellular localization and transcriptional activation. Activity of the first three members of the family is controlled by cytosolic-nuclear translocation.

FOXO1 regulates expression of a number of genes that play critical roles in cell cycle and apoptosis. A pivotal regulatory mechanism of FOXO is reversible phosphorylation, catalyzed by kinases and phosphatases. Phosphorylation of FOXO1 is associated with 14-3-3 binding and cytosolic localization, whereas dephosphorylated FOXO1 translocates to the nucleus and is transcriptionally active.

SUMMARY OF THE INVENTION

A genus of tricyclics has now been found that activates PPA2. The compounds described herein have anti-proliferative effects, but are devoid of amine transporter inhibitory properties, GPCR mediated pharmacology (including dopamine, serotonin and adrenergic receptors) which are associated with the CNS and cardiovascular effects of tricyclic neuroleptics such as clomipramine and chlorpromazine. The compounds described herein, which are based on tricyclic scaffolds, exhibit anti-proliferative effects and are useful as monotherapy in cancer treatment. Additionally, they can be used in combination with other drugs to restore sensitivity to chemotherapy where resistance has developed.

In a first aspect the invention relates to compounds of formula (I):

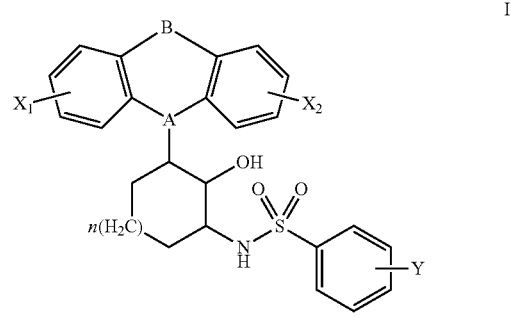

wherein:
B is selected from the group consisting of: —S—, —(CH$_2$—CH$_2$)—, and —CH═CH—;
A is selected from N and CH;
n is zero, 1 or 2;
X$^1$ is selected from —H, —F, —Cl, —CF$_3$, and —CN;
X$^2$ is selected from —H, —F, —Cl, —CF$_3$, and —CN; and
Y represents one or two substituents each independently selected from —H, —F, —Cl, —(C$_1$-C$_3$)haloalkyl, —(C$_1$-C$_3$)haloalkoxy, —(C$_1$-C$_3$)alkoxy, —C(═O)(C$_1$-C$_3$)alkyl, —C(═O)H, —(C$_1$-C$_3$)hydroxyalkyl, —(C$_1$-C$_3$)haloalkylthio, —N$_3$, and —CN.

In a second aspect, the invention relates to methods and uses of the above-described compounds in medicine, particularly for the treatment of a disease chosen from: (a) cancer; (b) diabetes; (c) autoimmune disease; (d) age onset proteotoxic disease; (e) mood disorder; (f) acne vulgaris; (g) solid organ transplant rejection; (h) graft vs. host disease; (i) cardiac hypertrophy; (j) viral infection; (k) parasitic infection; and (l) psychostimulant abuse. These methods include administering to a patient a therapeutically effective amount of a compound described above.

In a third aspect, the invention relates to a method for restoring sensitivity to one or more chemotherapeutic agents in the treatment of cancer. The method includes administering an effective amount of a compound described above.

In a fourth aspect, the invention relates to a method for treating a disease or disorder in a patient where the disease or disorder involves the dysregulation of PP2A influenced signaling cascades such as the PI3K-AKT, MAP kinase and mTOR pathways. These methods include administering to a patient a therapeutically effective amount of a compound described above.

In a fifth aspect, the invention relates to pharmaceutical compositions comprising the above-described compounds.

DETAILED DESCRIPTION OF THE INVENTION

Substituents are generally defined when introduced and retain that definition throughout the specification and in all independent claims.

In a composition aspect, the invention relates to compounds of formula (I):

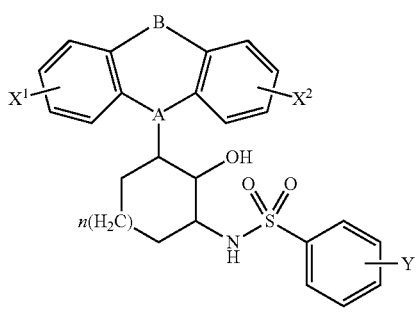

I as described above.

In some embodiments, the invention relates to compounds of formula (II), wherein the relative configurations are such that the amine and the tricycle are both trans to the alcohol:

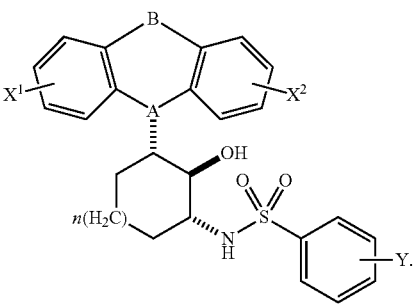

II

In this trans:trans subgroup, compounds can be either single enantiomers IIIa and IIIb or a mixture of the two. If a mixture, the mixture will most commonly be racemic, but it need not be. Substantially pure single enantiomers of biologically active compounds such as those described herein often exhibit advantages over their racemic mixture.

In some embodiments, the invention relates to compounds of formula (Ma):

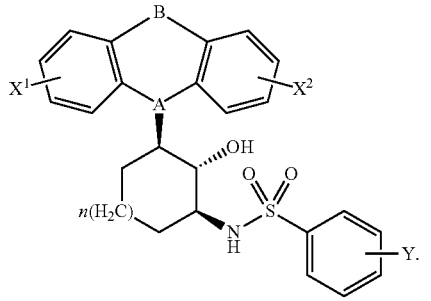

IIIa

In some embodiments, the invention relates to compounds of formula (Mb):

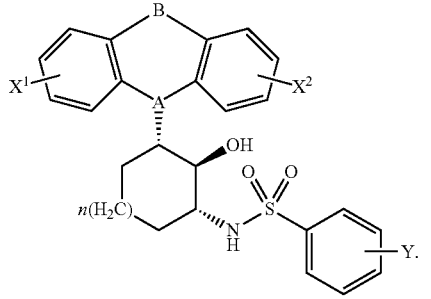

IIIb

In the embodiments described below, the compound may be of formula I, II, IIIa or IIIb, unless otherwise indicated.

In some embodiments, B is —(CH$_2$—CH$_2$)—. In some embodiments, B is —S—. In some embodiments, B is —CH=CH—.

In some embodiments, A is N. In some embodiments, A is CH.

In some embodiments, n is zero. In some embodiments, n is one. In some embodiments, n is two.

In some embodiments, $X^1$ is —H. In some embodiments, $X^1$ is —F. In some embodiments, $X^1$ is —Cl. In some embodiments, $X^1$ is —CF$_3$. In some embodiments, $X^1$ is —CN.

In some embodiments, $X^2$ is —H. In some embodiments, $X^2$ is —F. In some embodiments, $X^2$ is —Cl. In some embodiments, $X^2$ is —CF$_3$. In some embodiments, $X^2$ is —CN.

In some embodiments, $X^1$ and $X^2$ are both —H.

In some embodiments, Y is —H. In some embodiments, Y is —F. In some embodiments, Y is —Cl. In some embodiments, Y is —(C$_1$-C$_3$)haloalkyl. In some embodiments, Y is —CF$_3$. In some embodiments, Y is —CH$_2$CF$_3$ or —CF$_2$CF$_3$. In some embodiments, Y is —(C$_1$-C$_3$)haloalkoxy. In some embodiments, Y is —OCF$_3$. In some embodiments, Y is —OCHF$_2$. In some embodiments, Y is —(C$_1$-C$_3$)alkoxy. In some embodiments, Y is —OCH$_3$. In some embodiments, Y is —C(═O)(C$_1$-C$_3$)alkyl. In some embodiments, Y is —C(═O)CH$_3$. In some embodiments, Y is —C(═O)H. In some embodiments, Y is —(C$_1$-C$_3$)hydroxyalkyl. In some embodiments, Y is —C(CH$_3$)$_2$OH. In some embodiments, Y is —(C$_1$-C$_3$)haloalkylthio. In some embodiments, Y is —SCF$_3$. In some embodiments, Y is —N$_3$. In some embodiments, Y is —CN. In some embodiments, one instance of Y is H or Cl, and another instance of Y is selected from —H, —F, —Cl, —(C$_1$-C$_3$)haloalkyl, —(C$_1$-C$_3$)haloalkoxy, —(C$_1$-C$_3$)alkoxy, —C(═O)(C$_1$-C$_3$)alkyl, —C(═O)H, —(C$_1$-C$_3$)hydroxyalkyl, —(C$_1$-C$_3$)haloalkylthio, —N$_3$, and —CN. In some embodiments, one instance of Y is Cl, and another instance of Y is —OCF$_3$.

In some embodiments, B is —(CH$_2$—CH$_2$)— and n is one. One such example is shown below:

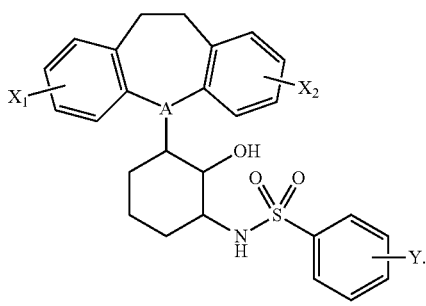

In some embodiments, B is —(CH$_2$—CH$_2$)—, A is N, and n is one. One such example is shown below:

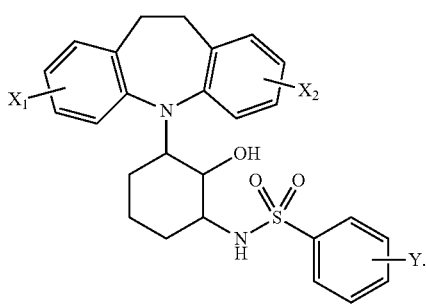

In some embodiments, B is —(CH$_2$—CH$_2$)— and A is N. One such example is shown below:

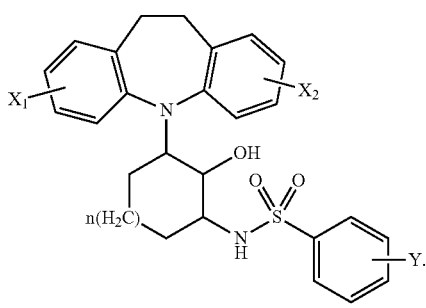

In some of these embodiments, X$^1$ and X$^2$ are both —H. In some embodiments, Y is in the para position, as shown below:

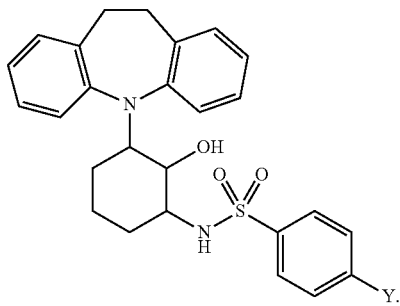

In some embodiments, Y is selected from —H, —F, —Cl, —(C$_1$-C$_3$)haloalkyl, —(C$_1$-C$_3$)haloalkoxy, —(C$_1$-C$_3$)alkoxy, —C(═O)(C$_1$-C$_3$)alkyl, —C(═O)H, —(C$_1$-C$_3$)hydroxyalkyl, —(C$_1$-C$_3$)haloalkylthio, —N$_3$, and —CN. In some embodiments, Y is selected from —H, —F, —Cl, —CF$_3$, —CH$_2$CF$_3$, —CF$_2$CF$_3$—OCF$_3$, —OCHF$_2$, —OCH$_3$, —C(═O)CH$_3$, —C(═O)H, —C(CH$_3$)$_2$OH, —SCF$_3$, —N$_3$, and —CN. In some embodiments, Y is —OCF$_3$.

The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Unless otherwise stated, all tautomeric forms of the compounds of the invention are within the scope of the invention.

The compounds described herein contain one or more asymmetric centers and may thus give rise to enantiomers, diastereomers, and other stereoisomeric forms which may be defined in terms of absolute stereochemistry as (R)- or (S)-. The present invention is meant to include all such possible isomers. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; wavy lines indicate disavowal of any stereochemical implication which the bond it represents could generate; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

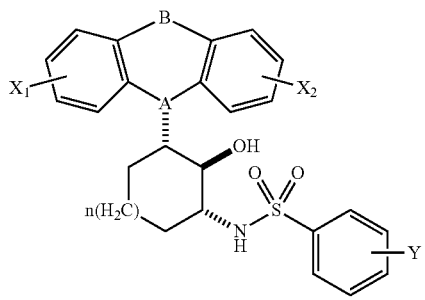

indicates either, or both, of the two trans:trans enantiomers:

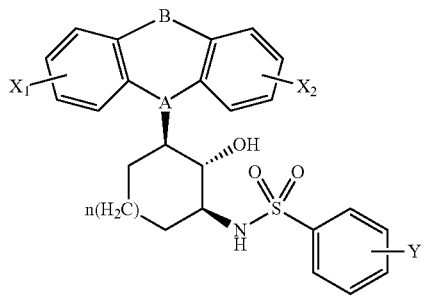

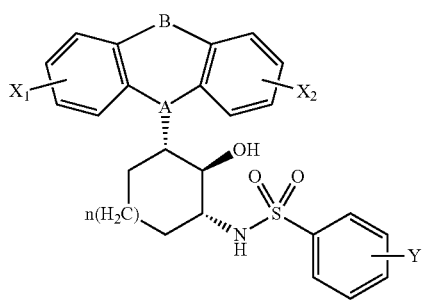

in any ratio, from pure enantiomers to racemates. The graphic representation:

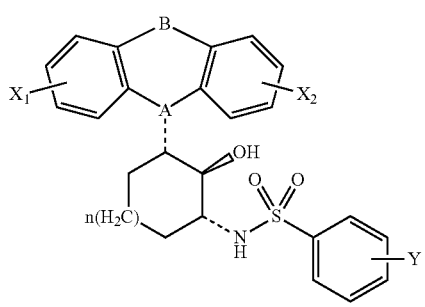

indicates a single enantiomer of unknown absolute stereochemistry, i.e. it could be either of the two preceding structures, as a substantially pure single enantiomer. And, finally, the representation:

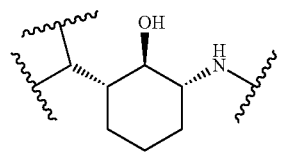 [SMILES: *N[C@@H]1CCC[C@H](C(*)*)[C@H]1O]

indicates a pure (1R,2R,6S)-2-amino-6-(C-attached tricycle) cyclohexanol. For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(1R, 2R,6S)-rel-" indicates that the three chiral centers are in that relative relationship, which would be depicted in a structural diagram by solid bold and dashed lines, whereas "(1R,2R, 6S)" without the "rel" indicates a single enantiomer of that absolute configuration, which would be depicted in a structural diagram by solid and broken wedges.

In some embodiments, the invention relates to compounds of formula:

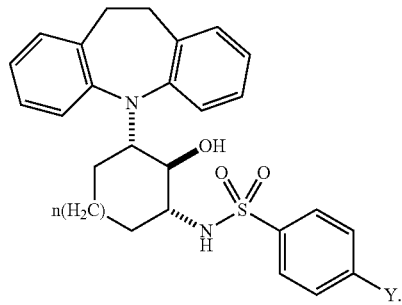

In some embodiments, the invention relates to compounds of formula:

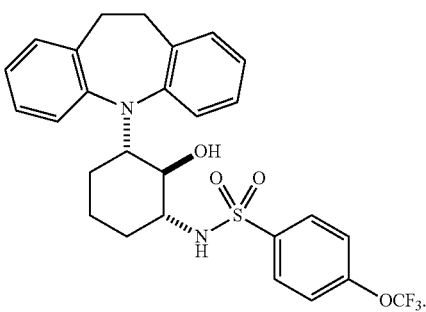

In some embodiments, the invention relates to a compound of formula:

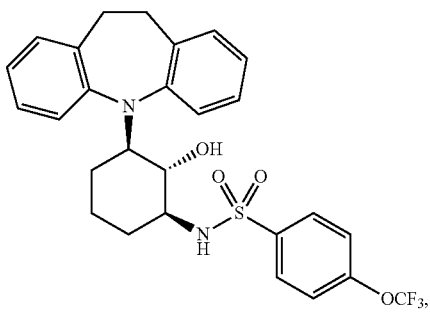 [SMILES: O=S(=O)(N[C@H]1CCC[C@@H](N2c3ccccc3CCc3ccccc32)[C@@H]1O)c1ccc(OC(F)(F)F)cc1]

while in other embodiments, the invention relates to a compound of formula:

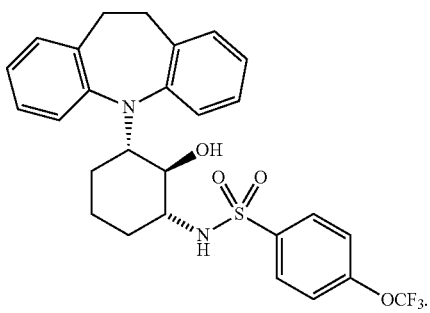 [SMILES: O=S(=O)(N[C@@H]1CCC[C@H](N2c3ccccc3CCc3ccccc32)[C@H]1O)c1ccc(OC(F)(F)F)cc1]

All the members of the genus described above exhibit biological activity in screens that are predictive of utility. However, it may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genus that are not in the public's possession.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating cancer in a patient, the method comprising administering to the patient a therapeutically effective amount of a compound of formula (I), or a pharmaceutically acceptable salt form thereof. In some embodiments, the cancer is characterized by dysregulation of the PI3K-AKT-FOXO signaling pathway. For example, the cancer can be selected from the group consisting of: ovarian, pancreatic, renal cell, breast, prostate, lung, hepatocellular carcinoma, glioma, leukemia, lymphoma, colorectal cancers, and sarcomas.

In some embodiments, the method further comprises administering one or more additional cancer chemotherapeutic agents. In some embodiments, the one or more additional cancer chemotherapeutic agents are EGFR inhibitors. For example, the additional chemotherapeutic agent may be erlotinib or gefitinib.

In some embodiments, the cancer is chemotherapy resistant cancer. In some embodiments, the method further comprises administering one or more cancer chemotherapeutic agents. In some embodiments, the one or more cancer chemotherapeutic agents are EGFR inhibitors. For example, the chemotherapeutic agent is erlotinib or gefitinib.

In some embodiments, administration of a compound of formula (I) or a pharmaceutically acceptable salt form thereof, can restore sensitivity to one or more chemotherapeutic agents in a patient wherein the patient has developed a resistance to the one or more chemotherapeutic agents.

Also provided herein is a method for treating diabetes in a patient, the method comprising administering to the patient a therapeutically effective amount of a compound of formula (I), or a pharmaceutically acceptable salt form thereof.

Further provided herein is a method for treating an autoimmune disease in a patient, the method comprising administering to the patient a therapeutically effective amount of a compound of formula (I). The autoimmune disease can be, for example, inflammatory bowel disease (IBD). Immune responses are constantly and tightly regulated and one important cellular component in maintaining self tolerance (i.e., prevention of autoimmunity) and tolerance of benign commensal gut flora are regulatory T cells (Treg). Treg can be subdivided into multiple phenotypes, but the most common are CD4+CD25+ T cells that express the transcription factor Foxp3. Foxp3 is a direct transcriptional target of FOXO proteins, particularly FOXO1 and FOXO3. Thus activation of FOXO proteins in naïve T-cells promotes and directs differentiation to maintain a population of Treg cells.

Acute immune mediated rejection and chronic immune mediated rejection are key obstacles to successful solid organ transplantation. It is believed that these forms of rejection can be prevented/overcome by amplifying Treg number and or function. Similarly, a common and morbid complication of allogeneic hematopoietic cell transplants (Allo-HCT) used to treat various malignant and non-malignant conditions, is graft versus host disease, in which the transplanted immune cells from the donor damage multiple organs in the recipient (most notably skin, gut, and liver). Increasing experimental and clinical data indicate that Tregs can be harnessed to prevent and or treat this disease process.

Thus compounds of the present invention are useful in treatment of autoimmune and related diseases, by activating FOXO proteins and inducing T cell differentiation to Tregs. Compounds may be administered therapeutically to subjects directly, or alternatively, T cells may be collected from a subject and differentiated ex vivo to Tregs as described by Taylor et al. [*Blood* 99, 3493-3499 (2002)]. Compounds of the present invention may be used alone or in combination with conventional immunosuppressive drugs such as cyclosporine, FK506 or rapamycin and its analogs. In addition compounds of the present invention may be co-administered with histone deacetylase inhibitors (HDACi) which have been shown to enhance Treg function by maintaining Foxp3 acetylation and activity.

Aspects of the invention include methods for treatment of autoimmune disease characterized by deficiency in Treg function comprising administering a therapeutically useful amount of compound of Formula I, optionally in combination with an HDAC inhibitor. The method can also include extraction of naïve T-cells from a patient, differentiation of T-cells to Tregs ex vivo by treatment with a compound of Formula I, optionally supplemented with an HDACi, followed by administration of Tregs to patient with optional separation of compound of Formula I from Tregs prior to their administration. As stated above, autoimmune diseases that can be so treated include IBD, solid organ transplant rejection, and GvHD in allo-HCT.

In some embodiments, the compounds can be administered to a patient to treat an autoimmune disorder, for example, Addison's disease, Amyotrophic Lateral Sclerosis, celiac disease, Crohns disease, diabetes, eosinophilic fasciitis, Guillain-Barré syndrome (GBS), Graves' disease, Lupus erythematosus, Miller-Fisher syndrome, psoriasis, rheumatoid arthritis, ulcerative colitis, and vasculitis.

In some embodiments, the compound provided herein can be used for treating a disease or disorder in a patient wherein the disease or disorder involves excessive or unregulated cellular proliferation, the method comprising administering to the patient a therapeutically effective amount of a compound of formula (I). Also provided herein is a method for treating a disease or disorder in a patient where the disease or disorder involves the dysregulation of the pi3K-AKT- FOXO signaling pathway, the method comprising administering to the patient a therapeutically effective amount of a compound of formula (I).

Further provided herein is a method for treating a disease in a patient wherein the disease is characterized by proteotoxicity, including age onset proteotoxicity leading to neurodegeneration, the method comprising administering to the patient a therapeutically effective amount of a compound of formula I. Hyperphosphorylated Tau has been implicated as the pathogenic protein in several neurodegenerative diseases and furthermore PP2A has been shown to be an important phosphatase in reversing aberrant phosphorylation of Tau; see for example Ludovic Martin et al., Tau protein phosphatases in Alzheimer's disease: The leading role of PP2A in Ageing Research Reviews 12 (2013) 39-49; Miguel Medina and Jesus Avila, Further understanding of tau phosphorylation: implications for therapy in Expert Rev. Neurotherapy, 15(1), 115-112 (2015) and Michael Voronkov et al., Phosphoprotein phosphatase 2A: a novel druggable target for Alzheimer's disease in Future Med Chem. 2011 May, 3(7) 821-833. Hyperphosphorylated alpha-Synuclein is a second exemplar of a toxic protein, and again PP2A has been shown to reverse its aberrantly phosphorylated state; see for example Kang-Woo Lee et al., Enhanced Phosphatase Activity Attenuates alpha-Synucleinopathy in a Mouse Model in Neurobiology of Disease, May 11, 2011, 31(19) 6963-6971. In some embodiments, the disease is selected from the group consisting of: Alzheimer's disease, Parkinson's disease, Huntington's disease, amyotrophic lateral sclerosis, frontotemporal dementia, progressive supranuclear palsy, corticobasal degeneration and Pick's disease.

The compounds provided herein may further be used in a method for treating a mood disorder in a patient by administering to the patient a therapeutically effective amount of a compound of formula (I). In some embodiments, the mood disorder is stress induced depression.

Also provided herein is a method for treating acne vulgaris in a patient by administering to the patient a therapeutically effective amount of a compound of formula (I).

Further provided herein is a method for treating cardiac hypertrophy in a patient by administering to the patient a therapeutically effective amount of a compound of formula (I). In some embodiments, the cardiac hypertrophy is associated with a disease selected from hypertension, myocardial infarction, and valvular heart disease.

PP2A enzymes are involved in the regulation of cell transcription, cell cycle, and viral transformation. Many viruses, including cytomegalovirus, parainfluenza, DNA tumor viruses, and HIV-1, utilize different approaches to exploit PPA2 in order to modify, control, or inactivate cellular activities of the host [Garcia et al., Microbes and Infection, 2, 2000, 401-407]. Therefore, the compounds provided herein may further be used in a method for treating a viral infection in a patient by administering to the patient a therapeutically effective amount of a compound of formula (I). Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

In addition to viruses, parasites also have developed methods to interact with a host cell's PP2A-dependent regulatory pathways [Garcia et al., Microbes and Infection, 2, 2000, 401-407]. Further provided herein is a method for treating a parasitic infection in a patient by administering to the patient a therapeutically effective amount of a compound of formula (I). Examples of parasites that may cause viral infections to be treated include, but are not limited to, *Plasmodium* and *Theileria*.

The compounds are useful in the treatment of a variety of disorders, including as a monotherapy in cancer treatment, or used in combination with other drugs to restore sensitivity to chemotherapy where resistance has developed.

More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angio sarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

Serine/Threonine phosphatases, including PP2A are involved in modulation of synaptic plasticity (D. G. Winder and J. D. Sweatt, Nature Reviews Neuroscience, vol 2, July 2001, pages 461-474). Persistently decreased PP2A activity is associated with maintenance of Long Term Potentiation (LTP) of synapses, thus treatment PP2A activators such as those described here may reverse synaptic LTP. Psychostimulant drugs of abuse such as cocaine and methamphetamine are associated with deleterious synaptic LTP (L. Mao et al, Neuron 67, Sep. 9, 2010 and A. Stipanovich et al, Nature vol 453, 2008, pages 879-884), which may underlie the pathology of addiction and relapse therefore PP2A activators described here may be useful as treatments for psychostimulant abuse.

Abnormalities in synaptic structure and signaling are linked to autistic spectrum disorder, see for example, Y Chen et al., CTTNBP2, but not CTTNBP2NL, regulates dendritic spinogenesis and synaptic distribution of the striatin-PP2A complex, Molecular Biology of the Cell, 23, Nov. 15, 2012, 4383-4392. PP2A has been shown to be important in normal development of dendritic spines, and treatment with compounds of the present invention may ameliorate or reverse autistic spectrum disorder.

The compounds described herein can also be administered in combination with existing methods of treating cancers, for example by chemotherapy, irradiation, or surgery. Thus, there is further provided a method of treating cancer comprising administering an effective amount of a compound according to formula (I), or a pharmaceutically acceptable salt form thereof, to a patient, wherein a therapeutically effective amount of one or more additional cancer chemotherapeutic agents are administered to the patient. Examples of suitable chemotherapeutic agents include EGFR inhibitors such as erlotinib or gefitinib.

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations", is incorporated herein by reference. In the event that there is a plurality of definitions for terms cited herein, those in this section prevail unless otherwise stated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents.

Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "modulate" with respect to a protein (such as a FOXO transcription factor protein) refers to activation of the protein and its biological activities associated with the protein pathway. Modulation of proteins includes up-regulation (i.e., agonizing, activation or stimulation). The mode of action of a modulator can be direct, e.g., through binding to the protein as a ligand. The modulation can also be indirect, e.g., through binding to and/or modifying another molecule which otherwise binds to and activates the protein.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1$^{st}$ Ed., Oxford University Press, 2000; and in *March's Advanced Organic chemistry: Reactions, Mechanisms, and Structure*, 5$^{th}$ Ed., Wiley-Interscience Publication, 2001.

In general, compounds of formula I can be prepared as shown in the syntheses below.

Synthesis of Example 1

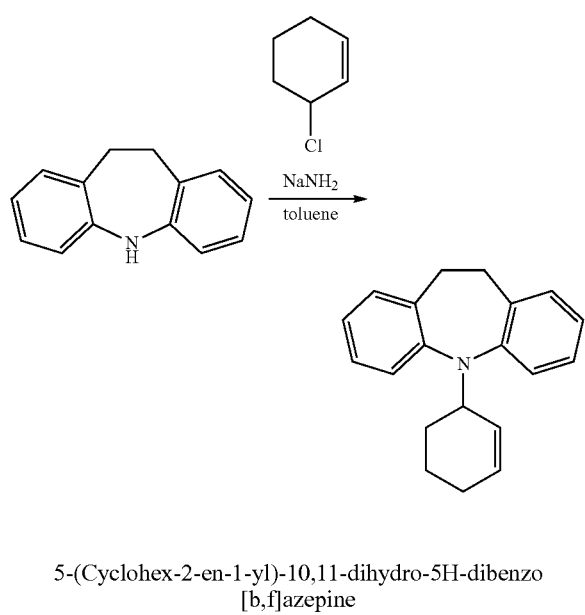

5-(Cyclohex-2-en-1-yl)-10,11-dihydro-5H-dibenzo[b,f]azepine

A solution of 10,11-dihydro-5H-dibenzo[b,f]azepine (8.37 g, 42.9 mmol) in toluene (50.0 mL) was treated with sodium amide (50% wt. suspension in toluene, 5.03 g, 64.3 mmol), and 3-chlorocyclohexene (5.0 mL, 45.0 mmol) and heated to 90° C. for 3 h. The mixture was cooled to 25° C. and poured over a solution of saturated aqueous ammonium chloride (100 mL). The organic layer was separated and the aqueous layer was extracted with CH$_2$Cl$_2$ (3×100 mL). The organic layers were combined, dried (Na$_2$SO$_4$), and concentrated in vacuo. The residue was dissolved in a minimal amount of CH$_2$Cl$_2$ and purified by flash chromatography (SiO$_2$, 100% hexanes). The purified fractions were combined, suspended in a minimal amount of methanol and treated with H$_2$O while stirring. The white precipitate that had formed was collected by filtration to afford the title compound as a white solid (8.99 g, 76%). $^1$H NMR (600 MHz, CDCl$_3$) δ 7.37 (2H, d, J=8.4 Hz), 7.17 (2H, t, J=8.4 Hz), 7.14 (2H, d, J=7.2 Hz), 6.99 (2H, t, J=7.2 Hz), 6.41 (1H, d, J=10.8 Hz), 5.88-5.90 (1H, m), 4.62-4.64 (1H, m), 3.24 (2H, d, J=9.0 Hz), 3.10 (2H, d, J=10.8 Hz), 2.05-2.07 (2H, m), 1.94-1.98 (1H, m), 1.81-1.84 (1H, m), 1.69-1.75 (1H, m), 1.62-1.66 (1H, m); $^{13}$C NMR (150 MHz, CDCl$_3$) δ 147.6, 132.8, 129.9, 129.1, 126.3, 126.1, 123.5, 122.8, 59.4, 33.0, 28.7, 25.2, 22.1; LCMS m/z 276.1936 ([M+H$^+$], C$_{20}$H$_{21}$N requires 276.1747).

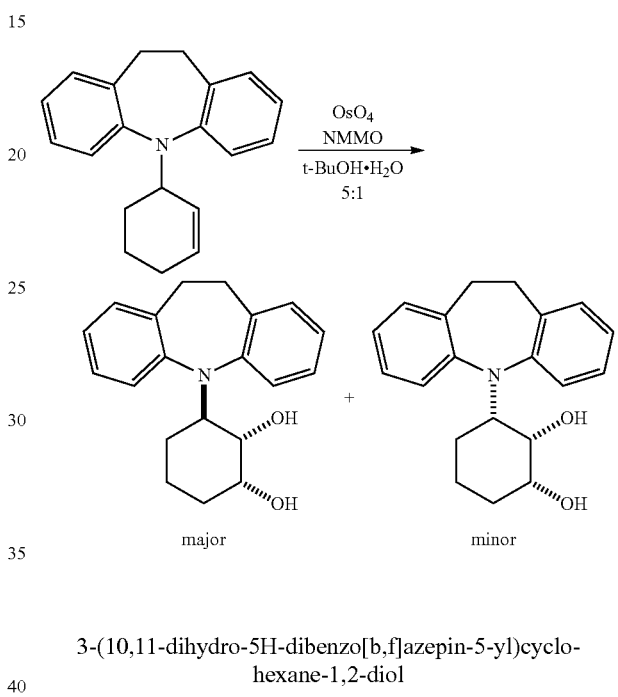

3-(10,11-dihydro-5H-dibenzo[b,f]azepin-5-yl)cyclohexane-1,2-diol

Example 10

A solution of 5-(cyclohex-2-en-1-yl)-10,11-dihydro-5H-dibenzo[b,f]azepine (4.93 g, 17.9 mmol) in t-BuOH—H$_2$O 5:1 (20.0 mL) at 25° C. was treated with OsO$_4$ (2.5 wt. % solution in t-BuOH, 2.23 mL, 0.178 mmol) and N-methyl morpholine N-oxide (2.31 g, 19.7 mmol). The mixture was stirred for 14 h at 25° C., treated with a saturated aqueous solution of sodium hydrosulfite (5 mL) and stirred for an additional 1 h. The mixture was concentrated in vacuo and the residue was taken up in a minimal amount of CH$_2$Cl$_2$ and purified by flash chromatography (SiO$_2$, 0-35% ethyl acetate-hexanes) to afford the mixture of two diastereomers as a beige foam (4.05 g, 73%). $^1$H NMR (600 MHz, CDCl$_3$) δ 7.30 (2H, d, J=5.4 Hz), 7.16 (2H, dd, J=8.4, 1.8 Hz), 7.13 (2H, d, J=7.2 Hz), 7.00-7.04 (2H, m), 4.24 (1H, td, J=9.0, 3.6 Hz), 4.16 (1H, br s), 3.64-3.76 (1H, m), 3.20-3.70 (2H, br m), 3.16 (1H, s), 2.70-3.10 (2H, br m), 2.76 (1H, br s), 2.13-2.15 (1H, m), 1.78-1.82 (1H, m), 1.60-1.64 (1H, m), 1.40-1.48 (3H, m); $^{13}$C NMR (150 MHz, CDCl$_3$) δ 142.9, 130.2, 126.6, 125.5, 124.0, 121.5, 118.8, 73.0, 69.6, 63.3, 32.8, 29.8, 28.2, 19.5; LCMS m/z 310.3236 ([M+H$^+$], C$_{20}$H$_{23}$NO$_2$ requires 310.1802).

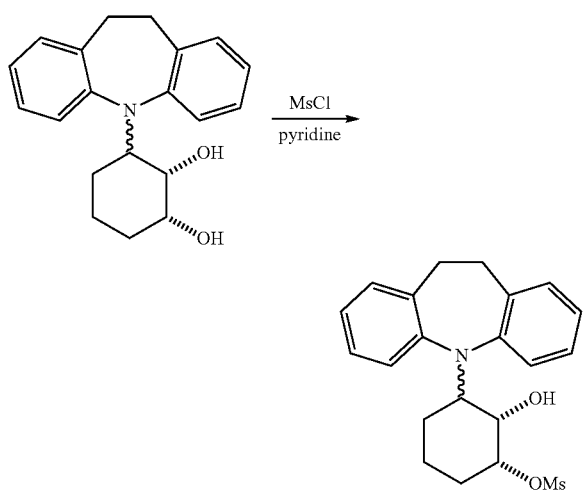

3-(10,11-dihydro-5H-dibenzo[b,f]azepin-5-yl)-2-hydroxycyclohexyl methanesulfonate A solution of 3-(10,11-dihydro-5H-dibenzo[b,f]azepin-5-yl)cyclohexane-1,2-diol (6.18 g, 20.0 mmol) in pyridine (10.0 mL) was cooled to 0° C. and treated dropwise with methanesulfonyl chloride (1.55 mL, 20.0 mmol). The mixture was warmed to 25° C., stirred for 3 h, and then concentrated in vacuo. The residue was suspended in $CH_2Cl_2$ (200 mL) and the organic phase was washed with 1 M HCl (3×100 mL), dried ($Na_2SO_4$), and concentrated in vacuo. The residue was dissolved in a minimal amount of $CH_2Cl_2$ and purified by flash chromatography ($SiO_2$, 0-35% ethyl acetate-hexanes) to afford the mixture of diastereomers as a white solid (6.32 g, 82%). $^1$H NMR (600 MHz, $CDCl_3$) δ 7.27-7.38 (2H, br m), 7.13-7.20 (4H, br m), 7.02 (2H, t, J=7.2 Hz), 5.02-5.03 (1H, m), 4.70 (1H, br s), 3.35-3.71 (2H, br m), 3.12 (3H, s), 2.72-3.01 (2H, br m), 2.54 (2H, br s), 2.04 (1H, br s), 1.93-1.97 (2H, m), 1.85-1.90 (1H, m), 1.56-1.62 (1H, m), 1.51-1.55 (1H, m); LCMS m/z 388.1527 ([M+H$^+$], $C_{17}H_{19}ClN_2$ requires 388.1577).

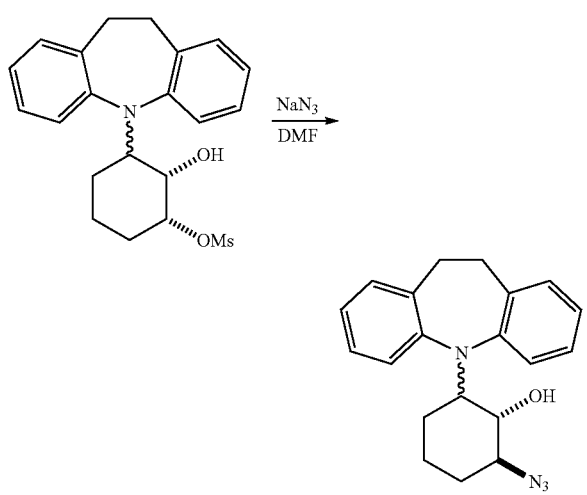

2-azido-6-(10,11-dihydro-5H-dibenzo[b,f]azepin-5-yl)cyclohexanol

A solution of 3-(10,11-dihydro-5H-dibenzo[b,f]azepin-5-yl)-2-hydroxycyclohexyl methanesulfonate (6.32 g, 16.3 mmol) in DMF (10.0 mL) was treated with $NaN_3$ (1.28 g, 19.6 mmol) and heated to 70° C. for 14 h. The mixture was cooled to 25° C. and partitioned between saturated aqueous NaCl (100 mL) and $CH_2Cl_2$ (300 mL). The organic layer was washed with saturated aqueous NaCl (3×100 mL), dried ($Na_2SO_4$), and concentrated in vacuo. $^1$H NMR (600 MHz, $CDCl_3$) δ 7.25-7.34 (2H, m), 7.17 (2H, t, J=7.2 Hz), 7.07-7.13 (2H, m), 6.95-7.06 (2H, m), 3.70 (2H, ddd, J=13.2, 10.2, 3.6 Hz), 3.49 (1H, t, J=9.6 Hz), 3.44 (1H, td, J=9.1, 4.2 Hz), 3.10-3.63 (2H, br m), 2.96 (1H, s), 2.64-3.10 (2H, br m), 2.17-2.19 (1H, m), 1.95-1.98 (1H, m), 1.73 (1H, dt, J=10.2, 3.0 Hz), 1.32 (1H, qt, J=13.3, 3.5 Hz), 1.24 (1H, qt, J=12.2, 3.2 Hz); LCMS m/z 335.2007 ([M+H$^+$], $C_{20}H_{22}N_4O$ requires 335.1866).

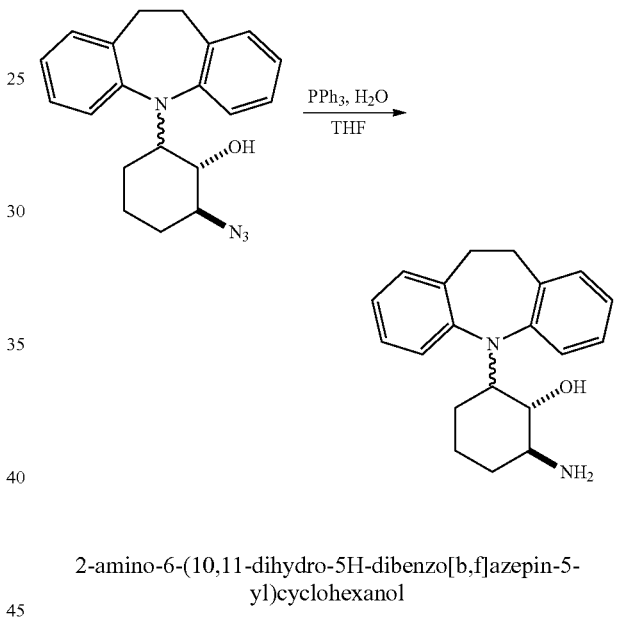

2-amino-6-(10,11-dihydro-5H-dibenzo[b,f]azepin-5-yl)cyclohexanol

The 2-azido-6-(10,11-dihydro-5H-dibenzo[b,f]azepin-5-yl)cyclohexanol residue was dissolved in THF (50 mL), treated with $PPh_3$ (4.71 g, 18.0 mmol), $H_2O$ (0.5 mL), and stirred for 14 h at 25° C. The mixture was concentrated in vacuo, taken up in a minimal amount of $CH_2Cl_2$ and purified by flash chromatography ($SiO_2$, 0-50% ethyl acetate-hexanes to remove nonpolar impurities, followed by 0-3% MeOH—$CH_2Cl_2$ to remove triphenylphosphine oxide, followed by 17:2:1 $CH_2Cl_2$:MeOH:$NH_4OH$ to elute the product). The purified fractions were combined, dried azeotropically with toluene to afford the title compound as a beige oil (3.14 g, 62%). $^1$H NMR (600 MHz, $CDCl_3$) δ 7.22 (2H, t, J=7.2 Hz), 7.15 (2H, t, J=7.2 Hz), 7.08-7.13 (2H, br m), 6.95-7.05 (2H, br m), 3.71 (1H, td, J=10.8, 3.0 Hz), 3.49 (2H, br s), 3.36 (1H, t, J=9.6 Hz), 2.79 (1H, td, J=12.6, 4.2 Hz), 2.55-3.10 (2H, br m), 2.40 (1H, s), 2.15-1.28 (1H, m), 1.83-1.85 (1H, m), 1.62-1.64 (1H, m), 1.23-1.34 (1H, m), 1.08-1.13 (1H, m); $^{13}$C NMR (150 MHz, $CDCl_3$) δ 137.9, 132.8, 128.7, 128.6, 126.7, 125.4, 77.6, 69.9, 56.5, 33.2, 30.3, 23.1, 21.6; LCMS m/z 309.1982 ([M+H$^+$], $C_{20}H_{24}N_2O$ requires 309.1961).

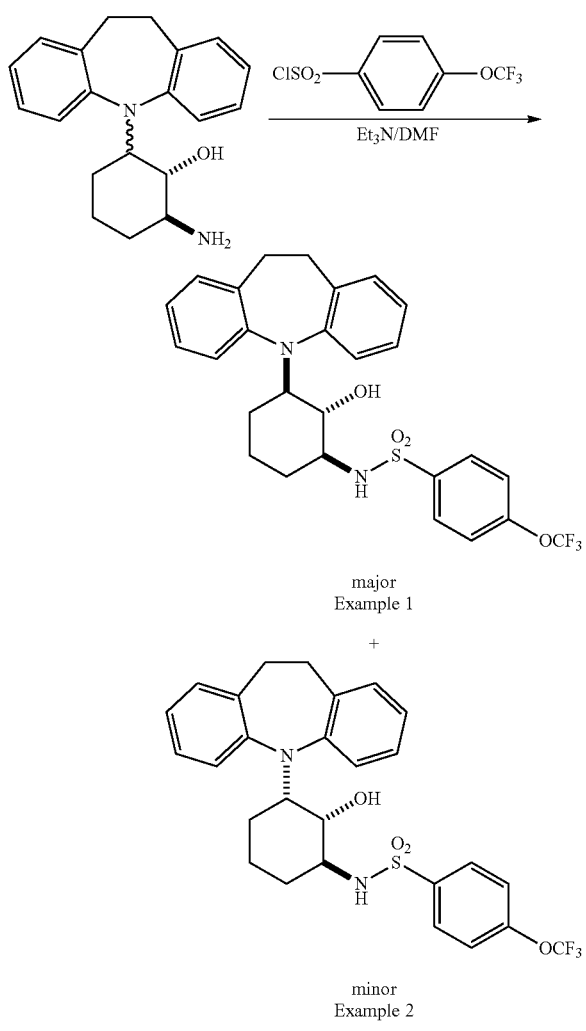

major
Example 1

+ minor
Example 2

N-((1,2-trans)-3-(10,11-dihydro-5H-dibenzo[b,f]azepin-5-yl)-2-hydroxycyclohexyl)-4-(trifluoromethoxy)benzenesulfonamide A solution of 2-amino-6-(10,11-dihydro-5H-dibenzo[b,f]azepin-5-yl)cyclohexanol (3.14 g, 10.2 mmol) in DMF (10.0 mL) was cooled to 0° C., treated with Et$_3$N (1.41 mL, 10.2 mmol), and 4-trifluoromethoxybenzenesulfonyl chloride (1.73 mL, 10.2 mmol). The mixture was warmed to 25° C., and stirred for 2 h. The mixture was partitioned between saturated aqueous NaCl (100 mL), and CH$_2$Cl$_2$ (300 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-25% ethyl acetate-hexanes). The purified fractions were combined, dissolved in a minimal amount of ethyl ether, and could either be recrystallized or precipitated with the addition of hexanes to afford the major diastereomer (Example 1), (1S,2S,3R)-rel, as a white solid (3.01 g, 55%). $^1$H NMR (600 MHz, CD$_3$OD) δ 7.93 (2H, t, J=9.0 Hz), 7.41 (2H, t, J=8.4 Hz), 7.32-7.41 (2H, br m), 7.06 (2H, t, J=7.8 Hz), 7.02-7.08 (2H, br m), 6.93 (2H, br s), 3.65 (1H, td, J=12.6, 3.6 Hz), 3.29-3.33 (2H, m), 3.17-3.57 (2H, br m), 3.11 (1H, ddd, J=12.6, 10.8, 4.2 Hz), 2.48-2.95 (2H, br m), 2.08-2.10 (1H, m), 1.58-1.60 (1H, m), 1.51 (1H, dt, J=13.2, 3.6 Hz), 1.27 (1H, qd, J=14.4, 3.0 Hz), 1.17 (1H, qt, J=12.6, 3.0 Hz), 1.08 (1H, qd, J=9.0, 3.6 Hz); $^{13}$C NMR (150 MHz, CD$_3$OD) δ 152.2, 141.1, 129.9, 129.6, 126.5, 126.4, 123.4, 121.7, 121.3, 120.0, 118.3, 74.4, 68.6, 59.3, 33.1, 31.8, 30.3, 22.1; LCMS m/z 533.3625 ([M+H$^+$], C$_{27}$H$_{27}$F$_3$N$_2$O$_4$S requires 533.1716).

A second group of fractions yielded Example 2, the minor diastereomer, (1S,2S,3 S)-rel, $^1$H NMR (600 MHz, CDCl$_3$) δ 7.74 (1H, s), 7.65 (2H, d, J=7.8 Hz), 7.23-7.25 (2H, m), 7.16 (1H, br s), 7.08-7.15 (4H, m), 7.00 (2H, br s), 5.48 (1H, br s), 4.92 (1H, t, J=7.8 Hz), 3.91 (1H, ddd, J=10.8, 8.4, 3.0 Hz), 3.38 (1H, ddd, J=17.4, 9.0, 4.8 Hz), 2.64-2.95 (2H, br m), 2.12-2.14 (1H, m), 1.86-1.91 (1H, m), 1.60-1.65 (1H, m), 1.52-1.58 (1H, m), 1.39-1.48 (1H, m), 1.26-1.31 (1H, m); LCMS m/z 533.3625 ([M+H$^+$], C$_{27}$H$_{27}$F$_3$N$_2$O$_4$S requires 533.1716).

Chiral chromatography was then utilized to separate the enantiomers of Example 1 into Examples 3a and 3b. Pure enantiomers were obtained from Chiralcel OD-H Resolution of Example 1 (Preparative Scale 80:20 hexane:iso-propanol) and Chiralcel IB-3 (Analytical Scale, 80:20 hexane:iso-propanol). The retention time for Example 3a was t$_R$=7.2 minutes and the material has specific optical rotation [α]$_D$=+16 (c=1.0, EtOH). The retention time for Example 3b was t$_R$=9.3 minutes and the material has specific optical rotation [α]$_D$=−16 (c=1.0, EtOH).

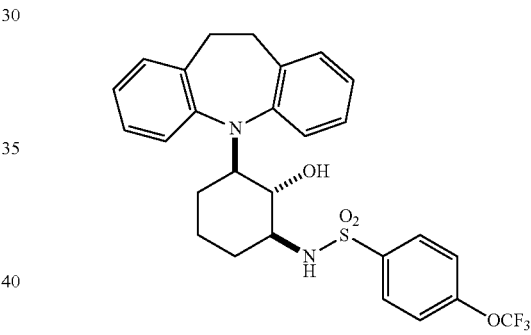

Example 1

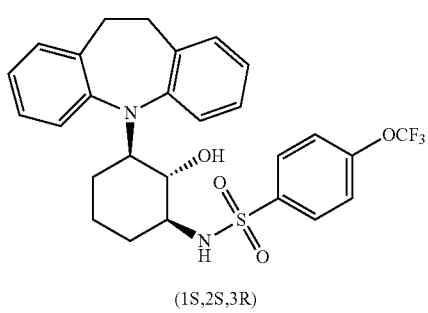

Example 3a (1S,2S,3R)

Example 3b

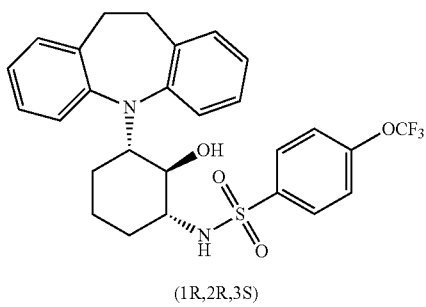

(1R,2R,3S)

Alternative Synthesis of Example 10, a single enantiomer of 3-(10,11-dihydro-5H-dibenzo[b,f]azepin-5-yl)cyclohexane-1,2-diol.

Resolution of Example 10

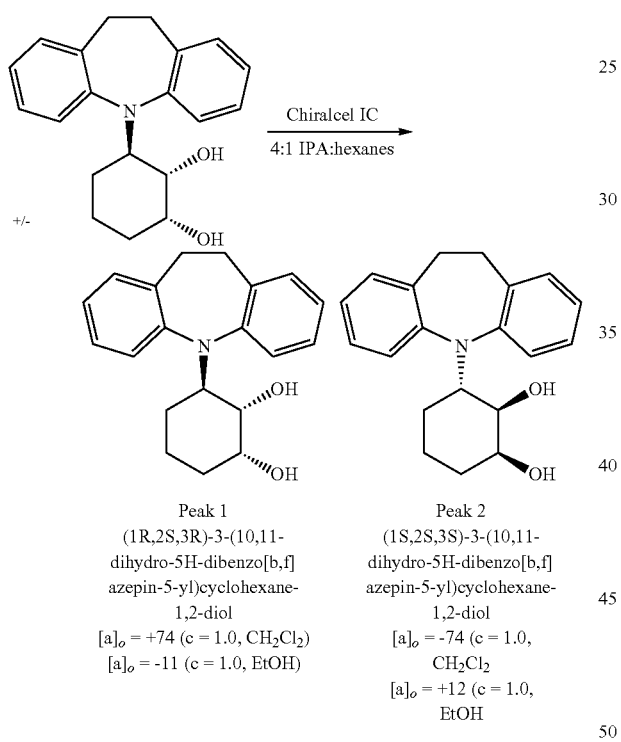

Peak 1
(1R,2S,3R)-3-(10,11-dihydro-5H-dibenzo[b,f]azepin-5-yl)cyclohexane-1,2-diol
$[a]_o = +74$ (c = 1.0, $CH_2Cl_2$)
$[a]_o = -11$ (c = 1.0, EtOH)

Peak 2
(1S,2S,3S)-3-(10,11-dihydro-5H-dibenzo[b,f]azepin-5-yl)cyclohexane-1,2-diol
$[a]_o = -74$ (c = 1.0, $CH_2Cl_2$)
$[a]_o = +12$ (c = 1.0, EtOH)

The racemic material was resolved by chiral HPLC. CHIRALPAK® IC column, 4:1 hexanes-IPA, retention times: peak 1, 4.94 min $[\alpha]_D=-11$ (c=1.0, EtOH) and ($[\alpha]_D=+74$ (c=1.0, $CH_2Cl_2$), peak 2, 7.92 min $[\alpha]_D=+12$ (c=1.0, EtOH) and $[\alpha]_D=-74$ (c=1.0, $CH_2Cl_2$).

The material was analyzed on (CHIRALCEL® IC-3 column, 4.6 mm×150 mmL, 3 μm, 4:1 hexanes-IPA, 1 mL/min, retention times: peak 1: 6.54 min; peak 2: 8.52 min).

Asymmetric Synthesis of Example 10

The compounds of formula I may also be synthesized by utilizing a known chiral starting material in a stereoselective route, removing the necessity of chiral separation of the enantiomers after synthesis of the racemate (or other mixture). The synthesis shown below employs a chiral allylic alcohol that can then be epoxidized and the chiral epoxide opened with the anion of a tricyclic moiety.

To establish the absolute configuration of these compounds, an asymmetric synthesis was carried out (Scheme 1).

The starting material methyl cyclohex-2-enecarboxylate (1) was synthesized according to methods detailed in the supporting information of the following reference: Timothy R. Ramadhar, Jun-ichi Kawakami, Alan J. Lough, and Robert A. Batey, Org. Lett., 2010, 12 (20), pp 4446-4449.

This material (1) was deracemized according to procedures described in Bernhard J. Lussem and Hans-Joachim Gais. J. Am. Chem. Soc. 2003, 125, 6066-6067 to provide the chiral (S)-cyclohex-2-enol (2). Literature lit. $[\alpha]_D=-42$ (c=1.0, $CHCl_3$), found $[\alpha]_D=-39$ (c=1.0, $CHCl_3$) establishing S absolute stereochemistry.

The epoxidation of (S)-cyclohex-2-enol (2) was performed according to procedures in Toshio Sato, Yoshihiko Gotoh, Makoto Watanabe, and Tamotsu Fujisawa Chemistry Letters, 1983, 1533-1536 to provide the chiral epoxide (1S,2S,3R)-cis-2,3-epoxycyclohexan-1-ol (3).

Benzylation of (1S,2S,3R)-cis-2,3-epoxycyclohexan-1-ol (3) was performed using procedures in Federico Calvani, Paolo Crotti, Cristina Gardelli, Mauro Pineschi. Tetrahedron, 1994, 50(45), 12999-13022 to provide (4) in Scheme 1.

Scheme 1

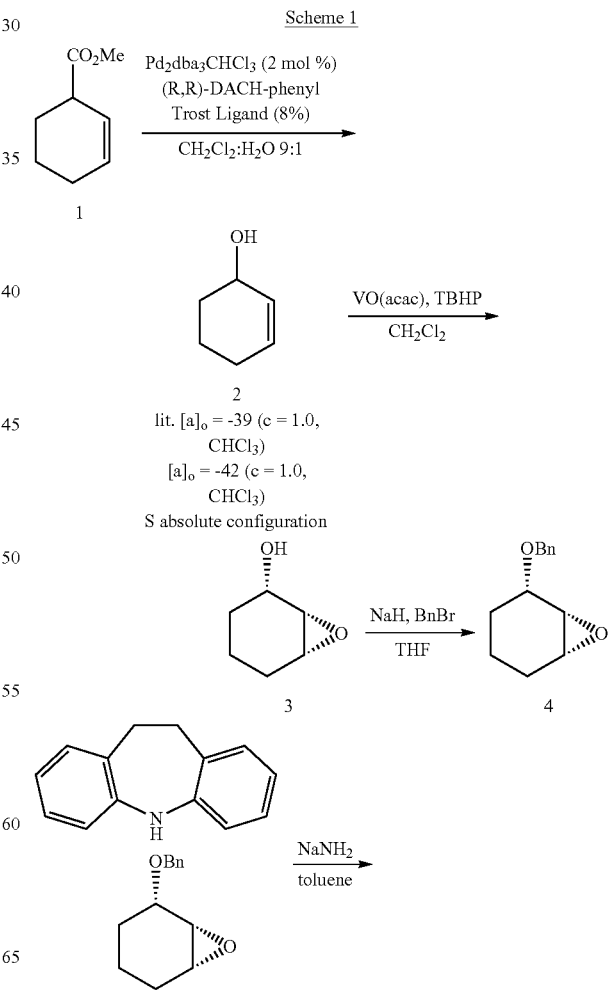

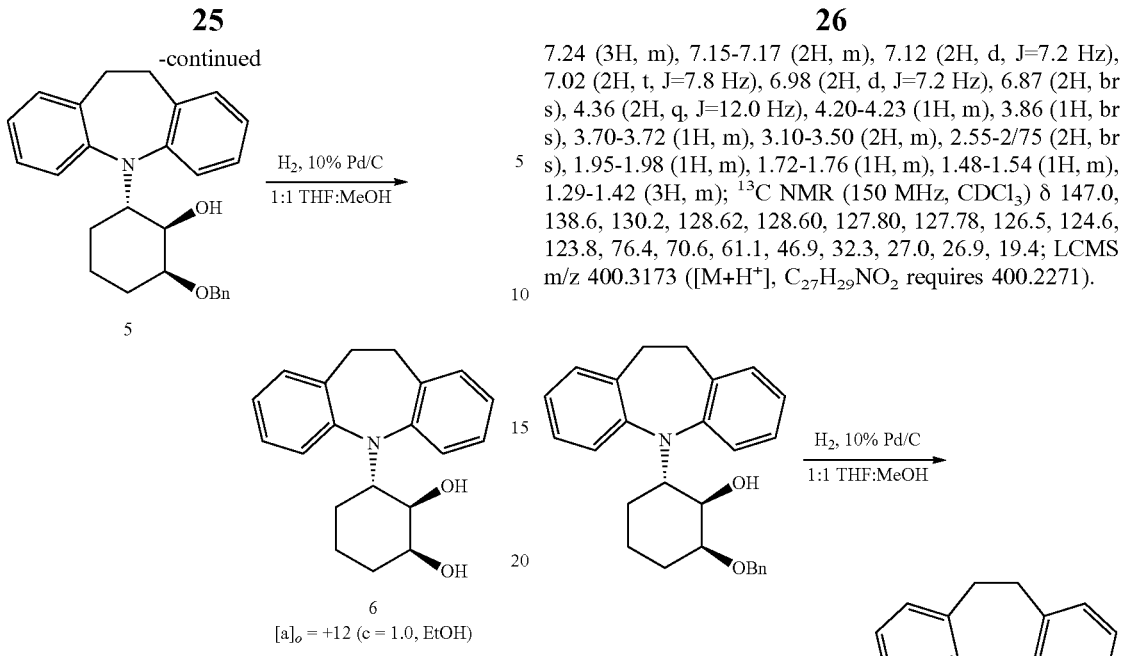

7.24 (3H, m), 7.15-7.17 (2H, m), 7.12 (2H, d, J=7.2 Hz), 7.02 (2H, t, J=7.8 Hz), 6.98 (2H, d, J=7.2 Hz), 6.87 (2H, br s), 4.36 (2H, q, J=12.0 Hz), 4.20-4.23 (1H, m), 3.86 (1H, br s), 3.70-3.72 (1H, m), 3.10-3.50 (2H, m), 2.55-2/75 (2H, br s), 1.95-1.98 (1H, m), 1.72-1.76 (1H, m), 1.48-1.54 (1H, m), 1.29-1.42 (3H, m); $^{13}$C NMR (150 MHz, CDCl$_3$) δ 147.0, 138.6, 130.2, 128.62, 128.60, 127.80, 127.78, 126.5, 124.6, 123.8, 76.4, 70.6, 61.1, 46.9, 32.3, 27.0, 26.9, 19.4; LCMS m/z 400.3173 ([M+H$^+$], C$_{27}$H$_{29}$NO$_2$ requires 400.2271).

Example 10
1S, 2R, 3S-absolute stereochemistry (1S,2R,3S)-3-(10,11-dihydro-5H-dibenzo[b,f]azepin-5-yl)cyclohexane-1,2-diol ((1S,2R,3S)

Example 10

A solution of (1R,2S,6S)-2-(benzyloxy)-6-(10,11-dihydro-5H-dibenzo[b,f]azepin-5-yl)cyclohexanol (0.570 g, 1.43 mmol) in THF:MEOH (1:1, 6.0 mL) was treated with 10% Pd/C (0.152 g, 0.143 mmol) and then placed under an atmosphere of H$_2$ (g). The mixture was stirred for 2 h at 25° C. then filtered thru Celite and concentrated in vacuo. The residue was dissolved in a minimal amount of CH$_2$Cl$_2$ and purified by flash chromatography (SiO$_2$, 0-35% ethyl acetate-hexanes) to afford the title compound as a clear foam (0.417 g, 94%) which correlated with the compound Example 10 by all spectroscopic methods. Material produced in this fashion exhibited [α]$_D$=+12 (c=1.0, EtOH), and the absolute stereochemistry is established as (−)-(1S, 2R,3S) by stereospecific synthetic steps and correlation with the known chiral (S)-cyclohex-2-enol starting material. The enantiomeric identity and purity was also confirmed by analytical chiral HPLC>98% (CHIRALCEL® IC-3 column, 4:1 hexanes-IPA, 1 mL/min, retention times: 8.62 min.

(1S,2R,3S)-3-(10,11-dihydro-5H-dibenzo[b,f]azepin-5-yl)cyclohexane-1,2-diol was carried forward to Example 3b by the methods described above to give material with specific optical rotation [α]$_D$=−16 (c=1.0, EtOH) and chiral HPLC identical to Example 3b obtained from the chromatographic resolution described above. This establishes the absolute configuration of Example 3b as 1R,2R,3S; furthermore the absolute configuration of the enantiomer Example 3a is also established as 1S,2S,3R.

(1R,2S,6S)-2-(benzyloxy)-6-(10,11-dihydro-5H-dibenzo[b,f]azepin-5-yl)cyclohexanol (5)

A solution of 10,11-dihydro-5H-dibenzo[b,f]azepine (1.30 g, 6.66 mmol) in toluene (10.0 mL) was treated with sodium amide (50% wt. suspension in toluene, 1.04 g, 13.3 mmol), and (1R,2S,6R)-2-(benzyloxy)-7-oxabicyclo[4.1.0]heptane (1.13 g, 5.55 mmol) and heated to 100° C. for 14 h. The mixture was cooled to 25° C. and poured over a solution of saturated aqueous ammonium chloride (100 mL). The organic layer was separated and the aqueous layer was extracted with toluene (3×100 mL). The organic layers were combined, dried (Na$_2$SO$_4$), and concentrated in vacuo. The residue was dissolved in a minimal amount of toluene and purified by flash chromatography (SiO$_2$, 0-10% ethyl acetate-hexanes) to afford the title compound as a white foam (1.10 g, 42%). $^1$H NMR (600 MHz, CDCl$_3$) δ 7.19-

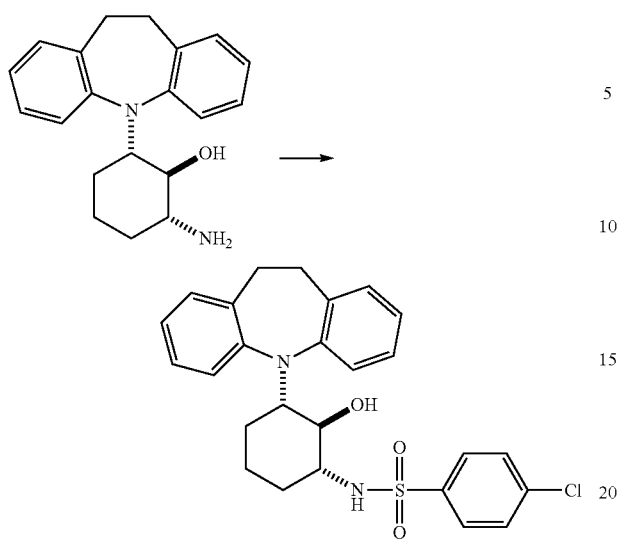

Example 4

N-(3-(10,11-dihydro-5H-dibenzo[b,f]azepin-5-yl)-2-hydroxycyclohexyl)-4-(chloro)benzenesulfonamide A solution of 2-amino-6-(10,11-dihydro-5H-dibenzo[b,f]azepin-5-yl)cyclohexanol (0.095 g, 0.307 mmol) in DMF (1.0 mL) was cooled to 0° C., treated with Et$_3$N (43.0 μL, 0.307 mmol), and 4-chlorobenzenesulfonyl chloride (0.065 g, 0.307 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes). The purified fractions were combined, dissolved in a minimal amount of ethyl ether, and were precipitated with the addition of hexanes to afford the title compound as a white solid (0.0671 g, 45%). $^1$H NMR (600 MHz, CDCl$_3$) δ 7.84 (2H, t, J=9.0 Hz), 7.50 (2H, t, J=9.0 Hz), 7.20-7.30 (1H, br m), 7.14 (3H, t, J=7.2 Hz), 7.09 (2H, br s), 7.02 (2H, br s), 5.02 (1H, d, J=4.8 Hz), 3.63 (1H, td, J=9.6, 3.6 Hz), 3.20-3.55 (2H, br s), 3.36 (1H, td, J=10.8, 1.2 Hz), 3.12 (1H, septet, J=5.4 Hz), 2.70-3.00 (2H, br s), 2.93 (1H, s), 2.14 (1H, m), 1.89 (1H, m), 1.60 (1H, m), 1.16-1.26 (2H, m), 1.08-1.16 (1H, m); LCMS m/z 483.1665 ([M+H$^+$], C$_{26}$H$_{27}$ClN$_2$O$_3$S requires 483.1504).

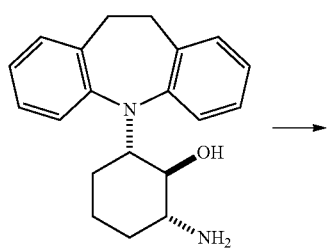

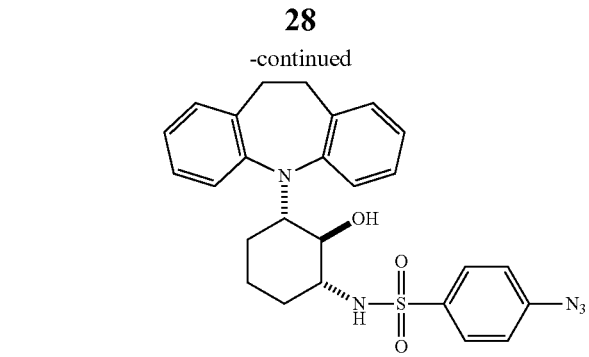

Example 5

N-(3-(10,11-dihydro-5H-dibenzo[b,f]azepin-5-yl)-2-hydroxycyclohexyl)-4-(azido)benzenesulfonamide A solution of 2-amino-6-(10,11-dihydro-5H-dibenzo[b,f]azepin-5-yl)cyclohexanol (0.0928 g, 0.301 mmol) in DMF (1.0 mL) was cooled to 0° C., treated with Et$_3$N (42.0 μL, 0.301 mmol), and 4-azidobenzenesulfonyl chloride (reference) (0.065 g, 0.301 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes). The purified fractions were combined, dissolved in a minimal amount of ethyl ether, and were precipitated with the addition of hexanes to afford the title compound as a white solid (0.0605 g, 41%). $^1$H NMR (600 MHz, CDCl$_3$) δ 7.88 (2H, t, J=8.4 Hz), 7.20-7.40 (1H, br s), 7.14 (2H, d, J=8.5 Hz), 7.12 (3H, t, J=8.0 Hz), 7.09 (2H, br s), 6.89-7.05 (2H, br s), 4.97 (1H, d, J=5.4 Hz), 3.63 (1H, td, J=9.6, 3.6 Hz), 3.20-3.55 (2H, br s), 3.34 (1H, t, J=9.0 Hz), 3.10 (1H, septet, J=5.4 Hz), 2.70-3.00 (2H, br s), 2.90 (1H, s), 2.14 (1H, m), 1.87 (1H, m), 1.60 (1H, m), 1.16-1.26 (2H, m), 1.08-1.16 (1H, m); LCMS m/z 490.2198 ([M+H$^+$], C$_{26}$H$_{27}$N$_5$O$_3$S requires 490.1907).

Carbon-linked compounds of the invention may be made by the general synthesis below:

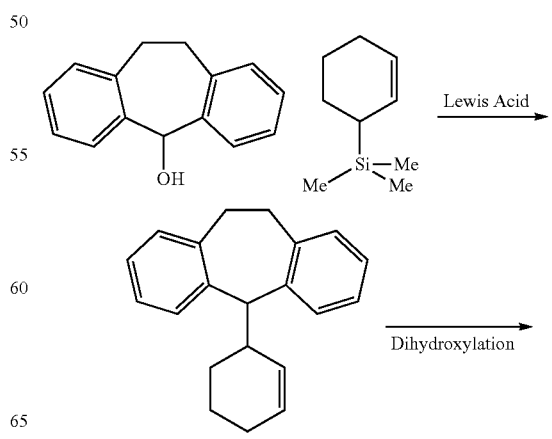

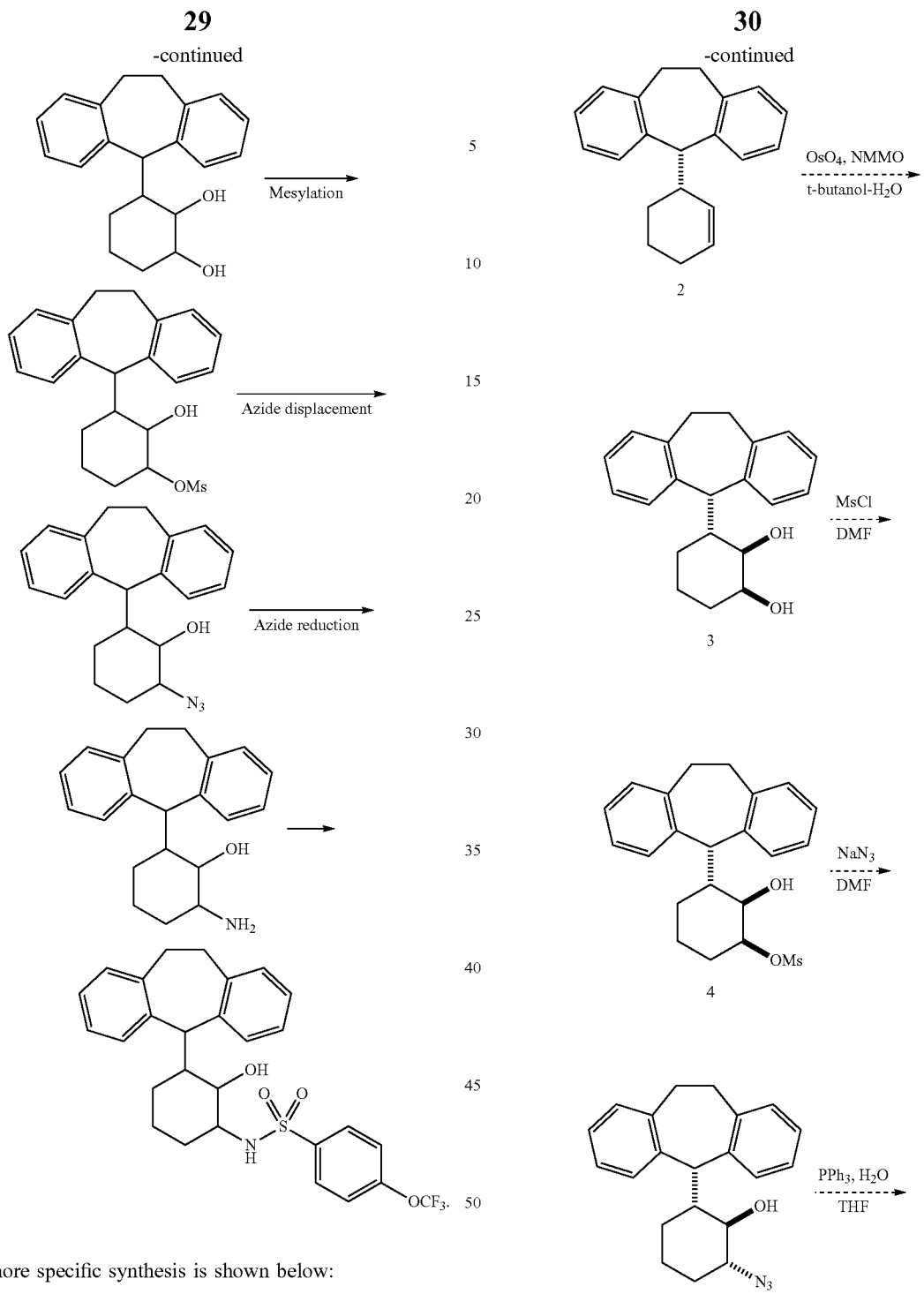
A more specific synthesis is shown below:
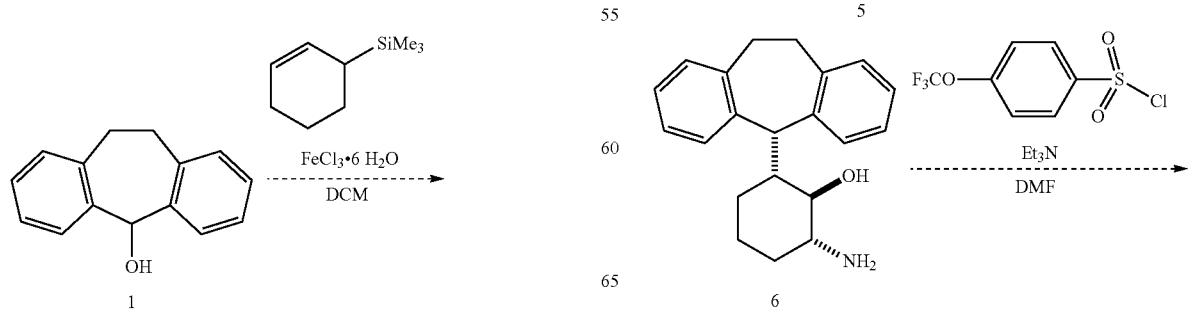

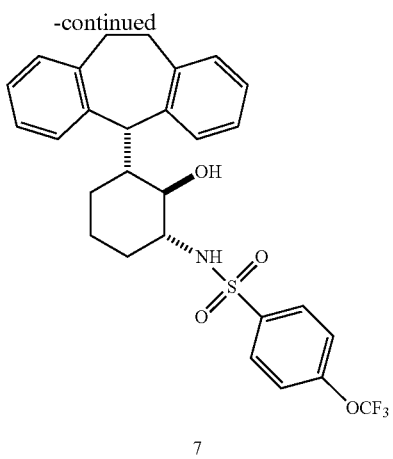

7

Example 7

The synthesis will be commenced by an iron-catalyzed allylation of commercially available 10,11-dihydro-5H-dibenzo[a,d][7]annulen-5-ol 1 with cyclohex-2-en-1-yltrimethylsilane to afford alkene 2 (*Synthetic Communications* 2010, 2042-2046). An osmium tetroxide catalyzed dihydroxylation of 2 will afforded diol 3. Treatment of diol 3 with methanesulfonyl choride will furnish mesylate 4. A sodium azide induced azide displacement of 4 will afforded azide 5. Amine 6 will be synthesized from 5 via a Staudinger reaction. Treating 6 with commercially available 4-(trifluoromethoxy)benzene-1-sulfonyl chloride will afford target sulfonamide 7.

Synthesis of Five-Membered Ring Compounds

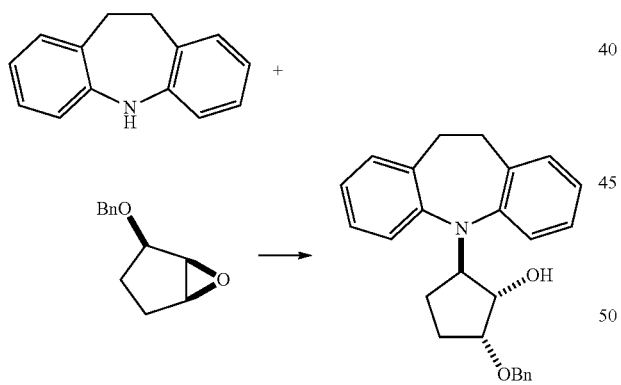

Example 12

(1S,2R,5R)-rel-2-(benzyloxy)-5-(10,11-dihydro-5H-dibenzo[b,f]azepin-5-yl)cyclopentanol A solution of 10,11-dihydro-5H-dibenzo[b,f]azepine (1.00 g, 5.12 mmol) in toluene (10 mL) was treated with sodium hydride (60% dispersion in mineral oil (0.286 g, 7.17 mmol) and (1S,2R,5S)-rel-2-(benzyloxy)-6-oxabicyclo [3.1.0]hexane at 25° C. stirred for 0.5 h. The vessel was then sealed and the mixture heated to 90° C. for 14 h. The vessel was cooled, treated with a solution of saturated ammonium chloride (50 mL), and then extracted with toluene (2×100 mL). The combined organic layers were washed with saturated aqueous NaCl (100 mL), dried ($Na_2SO_4$), and concentrated in vacuo. The residue was dissolved in a minimal amount of $CH_2Cl_2$ and purified by flash chromatography ($SiO_2$, 0-10% ethyl acetate-hexanes) to afford the title compound as a clear oil (1.00 g, 51%). $^1H$ NMR (600 MHz, $CD_3OD$) δ 7.23-7.26 (6H, m), 7.08 (3H, br s), 7.04 (2H, d, J=7.2 Hz), 6.91 (2H, t, J=7.2 Hz), 4.50 (1H, d, J=12.0 Hz), 4.41 (1H, d, J=11.9 Hz), 4.40 (1H, ddd, J=7.0, 4.2, 2.0 Hz), 4.05 (1H, dd, J=4.2, 2.0 Hz), 3.88 (1H, td, J=8.4, 4.2 Hz), 3.22-3.45 (2H, br s), 2.56-2.76 (2H, br s), 2.14-2.20 (1H, m), 1.78-1.83 (2H, m), 1.42-1.48 (1H, m); $^{13}C$ NMR (150 MHz, $CD_3OD$) δ 149.6, 139.6, 130.7, 129.3, 129.1, 128.9, 128.74, 128.67, 127.2, 124.4, 80.9, 75.0, 72.5, 65.3, 32.7, 28.1, 24.6; LCMS m/z 386.3178 ([M+H$^+$], $C_{26}H_{27}NO_2$ requires 386.2115).

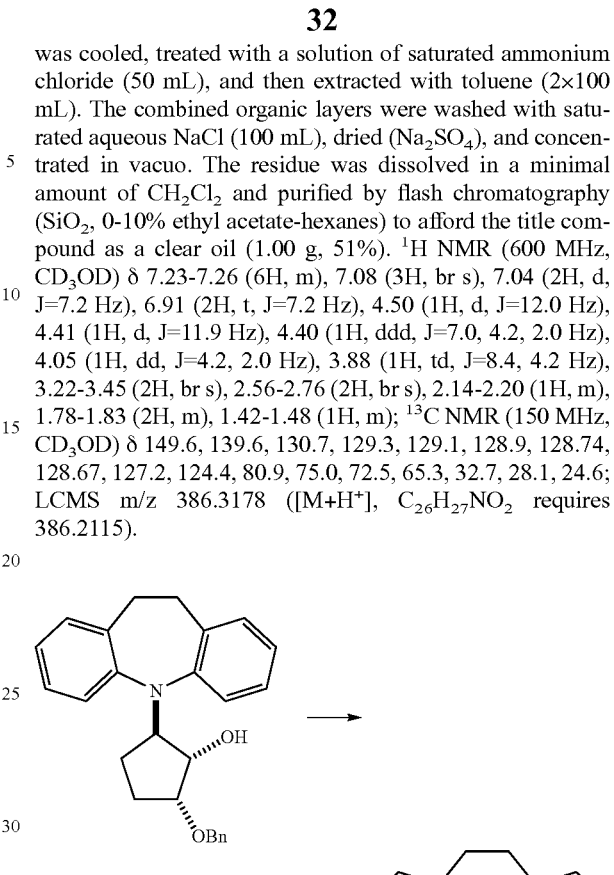

Example 13

(1R,2S,3R)-rel-3-(10,11-dihydro-5H-dibenzo[b,f] azepin-5-yl)cyclopentane-1,2-diol A solution of (1S,2R,5R)-rel-2-(benzyloxy)-5-(10,11-dihydro-5H-dibenzo[b,f]azepin-5-yl)cyclopentanol (1.00 g, 2.59 mmol) in THF:MeOH (1:1, 8.0 mL) was treated with 10% Pd/C (0.276 g), placed under an atmosphere of $H_2$ (g), and stirred for 6 h at 25° C. The mixture was filtered thru Celite and concentrated in vacuo to afford the title compound as a clear oil (0.772 g, 99%). $^1H$ NMR (600 MHz, $CDCl_3$) δ 7.13 (2H, t, J=7.2 Hz), 7.10 (2H, d, J=7.2 Hz), 7.05-7.31 (2H, br s), 6.96 (2H, t, J=7.2 Hz), 4.47 (1H, ddd, J=7.8, 5.4, 3.6 Hz), 4.16 (1H, q, J=6.0 Hz), 3.98 (1H, t, J=3.6 Hz), 3.30-3.60 (2H, br s), 2.60-2.90 (2H, br s), 2.44 (1H, br s), 2.28 (1H, sextet, J=7.8 Hz), 1.93 (1H, sextet, J=6.0 Hz), 1.74 (1H, sextet, J=7.2 Hz), 1.54 (1H, sextet, J=7.8 Hz); $^{13}C$ NMR (150 MHz, $CDCl_3$) δ 148.3, 135.5, 130.0, 126.5, 123.7, 122.4, 76.8, 73.2, 65.0, 31.9, 30.4, 28.3; LCMS m/z 296.1851 ([M+H$^+$], $C_{19}H_{21}NO_2$ requires 296.1645).

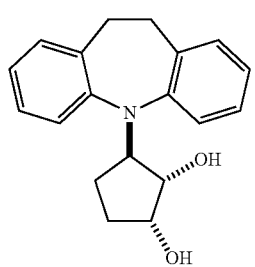

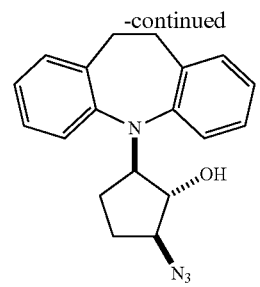

Example 15

Example 14

(3aS,4R,6aR)-rel-4-(10,11-dihydro-5H-dibenzo[b,f]azepin-5-yl)tetrahydro-3aH-cyclopenta[d][1,3,2]dioxathiole 2-oxide A solution of (1R,2S,3R)-rel-3-(10,11-dihydro-5H-dibenzo[b,f]azepin-5-yl)cyclopentane-1,2-diol (0.772 g, 2.61 mmol) in CH$_2$Cl$_2$ (10.0 mL) at 0° C. was treated dropwise with triethylamine (2.90 mL, 20.9 mmol), and SOCl$_2$ (0.57 mL, 7.84 mmol). The mixture was warmed to 25° C., stirred for 2 h, poured over a solution of saturated aqueous sodium chloride (100 mL), and then extracted into CH$_2$Cl$_2$ (3×100 mL). The combined organic layers were washed with water (2×100 mL), saturated aqueous sodium chloride (100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as a beige oil (0.782 g, 84%). $^1$H NMR (600 MHz, CDCl$_3$) δ (as a mixture of sulfite diastereomers) 7.21-7.24 (1H, m), 7.12-7.20 (3H, m), 7.07-7.10 (1H, m), 6.96-7.04 (3H, m), 1H [5.43 (t, J=5.4 Hz), 5.16 (t, J=6.0 Hz)], 1H [5.26 (d, J=6.0 Hz), 5.00 (d, J=6.6 Hz)], 1H [4.87 (d, J=5.4 Hz), 4.66 (d, J=3.6 Hz)], 2H [3.46-3.55 (m), 3.36-3.44 (m)], 2H [2.77-2.83 (m), 2.73-2.77 (m)], 2H [2.61 (sextet, J=6.0 Hz), 2.05-2.17 (m)], 1.91-1.99 (2H, m); LCMS m/z 357.3056 ([M+H$^+$], C$_{19}$H$_{20}$N$_2$O$_3$S requires 357.1267).

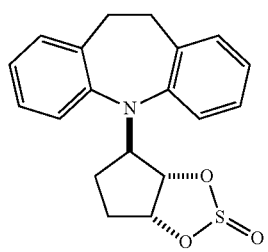

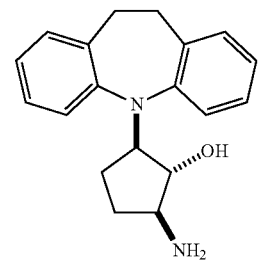

Example 16

(1R,2S,5R)-rel-2-amino-5-(10,11-dihydro-5H-dibenzo[b,f]azepin-5-yl)cyclopentanol A solution of (3aS,4R,6aR)-rel-4-(10,11-dihydro-5H-dibenzo[b,f]azepin-5-yl)tetrahydro-3aH-cyclopenta[d][1,3,2]dioxathiole 2-oxide (0.782 g, 2.19 mmol) in DMF (5.0 ml) was treated with potassium azide (0.404 g, 4.98 mmol), and heated to 100° C. under microwave irradiation for 14 h. The mixture was diluted with CH$_2$Cl$_2$ (200 mL) and this organic layer was washed with saturated aqueous NaCl (3×100 mL), dried (Na$_2$SO$_4$), and concentrated in vacuo. A small amount of the residue was purified by flash chromatography (SiO$_2$, 0-75% ethyl acetate-hexanes) to afford (1S,2S,5R)-rel-2-azido-5-(10,11-dihydro-5H-dibenzo[b,f]azepin-5-yl)cyclopentanol as a crude oil. $^1$H NMR (600 MHz, CDCl$_3$) δ 7.15 (4H, t, J=6.6 Hz), 7.00 (2H, t, J=7.8 Hz), 7.10-7.24 (2H, br m), 4.40 (1H, dt, J=4.8, 2.4 Hz), 3.97 (1H, t, J=4.8 Hz), 3.76 (1H, q, J=7.2 Hz), 3.42-3.66 (2H, br s), 2.60-2.95 (2H, br s), 2.26-2.36 (1H, br m), 2.16 (1H, dq, J=21.6, 7.2 Hz), 2.02 (1H, dq, J=18.6, 6.6 Hz), 1.84 (1H, dq, J=21.6, 5.4 Hz), 1.74 (1H, sextet, J=7.8 Hz); LCMS m/z 321.2008 ([M+H$^+$], C$_{19}$H$_{20}$N$_4$O requires 321.1710).

The residue was dissolved in THF (20.0 mL), treated with PPh$_3$ (0.689 g, 2.63 mmol), H$_2$O (0.5 mL), and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene to afford the title compound as a beige foam (0.401 g, 62% over 2 steps). $^1$H NMR (600 MHz, CDCl$_3$) δ 7.03-7.08 (2H, m), 6.94-6.98 (4H, m), 6.81 (2H, t, J=7.2 Hz), 4.11 (1H, dt, J=7.8, 4.8 Hz), 3.41 (1H, t, J=5.4 Hz), 3.12-3.48 (2H, br s), 2.76 (1H, q, J=6.6 Hz), 2.70-2.98 (2H, br s), 2.55-2.70 (2H, br m), 1.93 (1H, sextet, J=8.4 Hz), 1.70 (1H, sextet, J=7.2 Hz), 1.62 (1H, dq, J=21.6, 4.8 Hz), 1.21 (1H, dq, J=21.0, 9.0 Hz); LCMS m/z 295.3589 ([M+H$^+$], C$_{19}$H$_{22}$N$_2$O requires 295.1805).

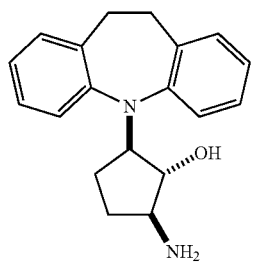

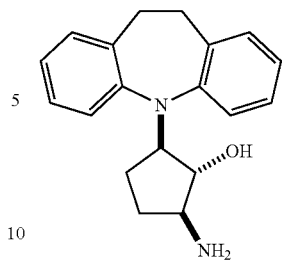

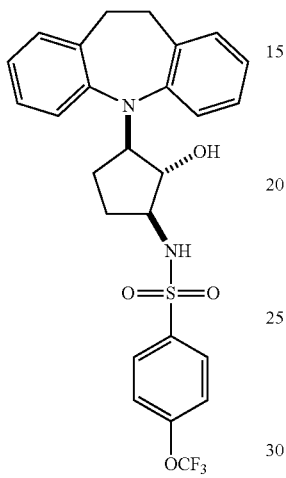

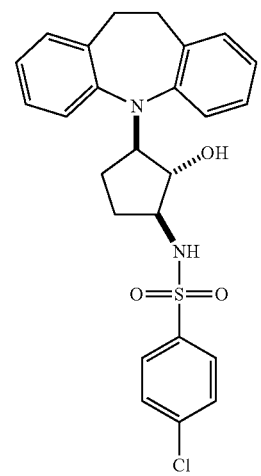

Example 17

N-((1S,2S,3R)-rel-3-(10,11-dihydro-5H-dibenzo[b,f]azepin-5-yl)-2-hydroxycyclopentyl)-4-(trifluoromethoxy)benzenesulfonamide A solution of (1R,2S,5R)-rel-2-amino-5-(10,11-dihydro-5H-dibenzo[b,f]azepin-5-yl)cyclopentanol (0.070 g, 0.238 mmol) in DMF (1.0 mL) was cooled to 0° C., treated with Et$_3$N (32.0 μL, 0.238 mmol), and 4-trifluoromethoxybenzenesulfonyl chloride (40.0 μL, 0.238 mmol). The mixture was warmed to 25° C., and stirred for 2 h. The mixture was partitioned between saturated aqueous NaCl (50 mL) and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-50% ethyl acetate-hexanes). The pure fractions were combined, concentrated, and the residue was dissolved in a minimal amount of ethyl acetate and precipitated with the addition of hexanes to afford the title compound as a white solid (0.081 g, 65%). $^1$H NMR (600 MHz, CDCl$_3$) δ 7.80 (2H, d, J=8.4 Hz), 7.25 (2H, d, J=8.4 Hz), 7.10-7.20 (1H, br m), 7.09-7.11 (4H, m), 7.03-7.08 (1H, br m), 6.95-7.02 (2H, br m), 4.94 (1H, d, J=7.2 Hz), 4.33 (1H, quintet, J=3.6 Hz), 3.84 (1H, dd, J=7.2, 3.6 Hz), 3.44-3.56 (2H, br s), 3.48 (1H, dq, J=12.0, 7.2 Hz), 2.82 (2H, br s), 2.28 (1H, d, J=3.6 Hz), 2.00-2.05 (1H, m), 1.96-1.99 (1H, m), 1.74 (1H, dq, J=21.6, 3.6 Hz), 1.62 (1H, dq, J=21.0, 7.2 Hz); LCMS m/z 519.1812 ([M+H$^+$], C$_{26}$H$_{25}$F$_3$N$_2$O$_4$S requires 519.1560).

Example 18

4-chloro-N-((1S,2S,3R)-rel-3-(10,11-dihydro-5H-dibenzo[b,f]azepin-5-yl)-2-hydroxycyclopentyl)benzenesulfonamide A solution of (1R,2S,5R)-2-amino-5-(10,11-dihydro-5H-dibenzo[b,f]azepin-5-yl)cyclopentanol (0.070 g, 0.238 mmol) in DMF (1.0 mL) was cooled to 0° C., treated with Et$_3$N (32.0 μL, 0.238 mmol), and 4-chlorobenzenesulfonyl chloride (0.050 g, 0.238 mmol). The mixture was warmed to 25° C., and stirred for 2 h. The mixture was partitioned between saturated aqueous NaCl (50 mL) and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-50% ethyl acetate-hexanes) to afford the title compound as a white solid (0.0855 g, 77%). $^1$H NMR (600 MHz, CDCl$_3$) δ 7.68 (2H, d, J=8.4 Hz), 7.39 (2H, d, J=8.4 Hz), 7.09-7.11 (4H, m), 7.02-7.20 (2H, br m), 6.98 (1H, t, J=7.2 Hz), 5.24 (1H, d, J=7.2 Hz), 4.31 (1H, quintet, J=3.0 Hz), 3.83 (1H, t, J=3.6 Hz), 3.42-3.56 (2H, br s), 3.45 (1H, dt, J=12.0, 7.2 Hz), 2.79 (2H, br s), 2.65 (1H, br s), 2.01 (1H, sextet, J=8.4 Hz), 1.92 (1H, sextet, J=7.8 Hz), 1.75 (1H, dq, J=22.2, 3.6 Hz), 1.57 (1H, dq, J=21.0, 7.8 Hz); LCMS m/z 469.1748 ([M+H$^+$], C$_{25}$H$_{25}$ClN$_2$O$_3$S requires 469.1347).

Synthesis of Phenothiazines

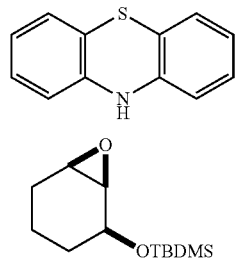

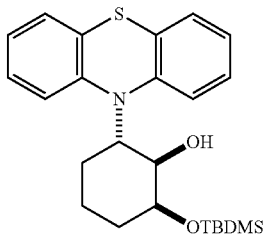

Example 20a (1R,2S,6S)-rel-2-((tert-butyldimethylsilyl)oxy)-6-(10H-phenothiazin-10-yl)cyclohexanol A solution of phenothiazine (1.00 g, 5.02 mmol) in toluene (10 mL) was treated with sodium hydride (60% dispersion in mineral oil, 0.281 g, 7.03 mmol) and (((1R,2S,6R)-rel-7-oxabicyclo[4.1.0]heptan-2-yloxy)(tert-butyl)dimethylsilane (1.26 g, 5.52 mmol) at 25° C. and stirred for 0.5 h. The vessel was then sealed and the mixture heated to 90° C. for 14 h. The vessel was cooled, treated with a solution of saturated ammonium chloride (50 mL), and extracted with toluene (2×100 mL). The combined organic layers were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as a beige oil (2.00 g, 93%). $^1$H NMR (600 MHz, CD$_3$OD) δ 7.28 (2H, d, J=8.4 Hz), 7.12 (2H, td, J=9.0, 1.8 Hz), 7.06 (2H, dd, J=7.8, 1.8 Hz), 6.93 (2H, td, J=7.8, 1.2 Hz), 4.22 (1H, br s), 4.07 (1H, td, J=10.8, 3.6 Hz), 3.85 (1H, dd, J=10.2, 2.4 Hz), 2.04-2.07 (1H, m), 1.65-1.73 (3H, m), 1.37-1.44 (2H, m), 0.91 (9H, s), 0.15 (3H, s), 0.09 (3H, s); $^{13}$C NMR (150 MHz, CD$_3$OD) δ 147.1, 131.1, 128.2, 127.8, 124.6, 123.5, 75.8, 73.4, 68.0, 33.2, 32.0, 26.5, 20.8, 19.1, −4.2, −4.6; LCMS m/z 428.2693 ([M+H$^+$], C$_{24}$H$_{33}$NO$_2$SSi requires 428.2074).

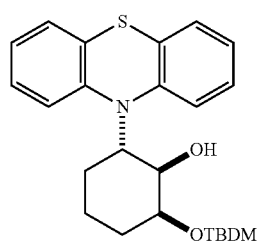

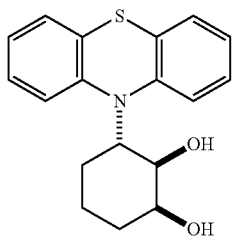

Example 20b (1S,2R,3S)-rel-3-(10H-phenothiazin-10-yl)cyclohexane-1,2-diol. A solution of (1R,2S,6S)-rel-2-((tert-butyldimethylsilyl)oxy)-6-(10H-phenothiazin-10-yl)cyclohexanol (2.00 g, 4.68 mmol) in THF (10 mL) was cooled to 0° C., treated with a solution of tetrabutylammonium fluoride (1 M, 5.14 mL, 5.14 mmol), allowed to warm to 25° C., and stirred for 6 h. The mixture was poured over a saturated aqueous solution of NaCl (50 mL), and extracted with CH$_2$Cl$_2$ (3×100 mL). The combined organic layers were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-50% ethyl acetate-hexanes) to afford the title compound as a beige film (1.74 g, 99%). $^1$H NMR (600 MHz, CD$_3$OD) δ 7.28 (2H, d, J=8.4 Hz), 7.15 (2H, td, J=9.0, 1.8 Hz), 7.07 (2H, dd, J=7.8, 1.2 Hz), 6.95 (2H, td, J=7.2, 0.6 Hz), 4.15 (1H, br s), 3.98 (1H, td, J=11.4, 3.6 Hz), 3.85 (1H, dd, J=10.2, 2.4 Hz), 2.18-2.20 (1H, m), 1.79-1.82 (1H, m), 1.70-1.74 (2H, m), 1.43-1.48 (2H, m); $^{13}$C NMR (150 MHz, CD$_3$OD) δ 147.0, 131.3, 128.3, 127.9, 124.7, 123.4, 74.4, 71.7, 68.3, 32.6, 32.0, 20.7; LCMS m/z 314.2188 ([M+H$^+$], C$_{18}$H$_{19}$NO$_2$S requires 314.1209.

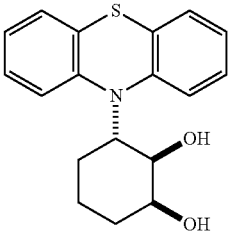

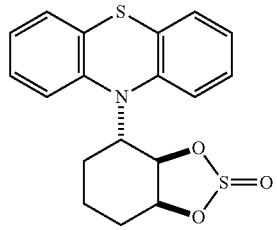

Example 20c (3aR,4S,7aS)-rel-4-(10H-phenothiazin-10-yl)hexahydrobenzo[d][1,3,2]dioxathiole 2-oxide A solution of (1S,2R,3 S)-rel-3-(10H-phenothiazin-10-yl)cyclohexane-1,2-diol (1.74 g, 5.56 mmol) in CH$_2$Cl$_2$ (20.0 mL) at 0° C. was treated dropwise with triethylamine (6.17 mL, 44.5 mmol), and SOCl$_2$ (1.21 mL, 16.7 mmol). The mixture was warmed to 25° C., stirred for 2 h, poured over a solution of saturated aqueous sodium chloride (100 mL), and then extracted into CH$_2$Cl$_2$ (3×100 mL). The combined organic layers were washed with water (2×100 mL), saturated aqueous sodium chloride (100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as two closely eluting compounds (sulfite diastereoisomers) as a white solid (1.05 g, 53%). $^1$H NMR (600 MHz, CD$_3$OD) δ (of the purified less polar isomer) 7.20 (2H, td, J=7.8, 1.2 Hz), 7.17 (2H, td, J=8.4, 1.8 Hz), 7.13 (2H, dd, J=7.8, 1.2 Hz), 7.00 (2H, td, J=8.4, 1.2 Hz), 4.92 (1H, dd, J=10.2, 5.4 Hz), 4.81-8.83 (1H, m), 4.36-4.41 (1H, m), 2.33-2.36 (1H, m), 2.24-2.27 (1H, m), 1.79-1.87 (1H, m), 1.71-1.77 (3H, m); $^{13}$C NMR (150 MHz, CD$_3$OD) δ 146.0, 128.4, 128.2, 127.9, 125.3, 124.2, 85.0, 81.5, 70.4, 32.2, 27.8, 21.1; LCMS m/z 360.0725 ([M+H$^+$], C$_{18}$H$_{17}$NO$_3$S$_2$ requires 360.0723).

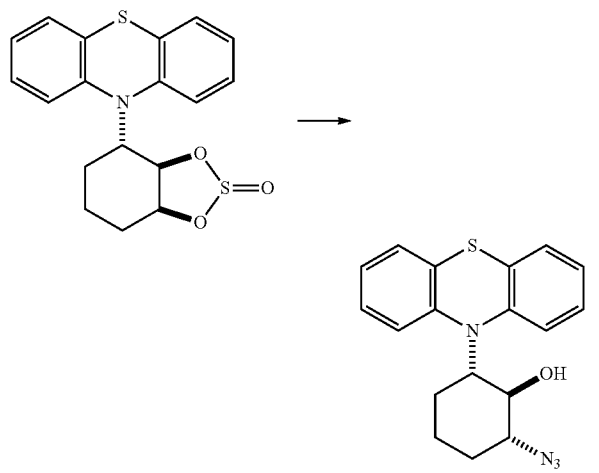

Example 20d (1R,2R,6S)-rel-2-azido-6-(10H-phenothiazin-10-yl)cyclohexanol

A solution of (3aR,4S,7aS)-rel-4-(10H-phenothiazin-10-yl)hexahydrobenzo[d][1,3,2]dioxathiole 2-oxide (1.05 g, 2.92 mmol) in DMF (5.0 ml) was treated with potassium azide (0.711 g, 8.76 mmol), and heated to 100° C. under microwave irradiation for 14 h. The mixture was diluted with CH$_2$Cl$_2$ (200 mL) and this organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound (0.630 g, 64%) as a crude oil. $^1$H NMR (600 MHz, CD$_3$OD) δ 7.27 (2H, dd, J=7.8, 1.2 Hz), 7.16 (2H, td, J=7.2, 1.2 Hz), 7.07 (2H, dd, J=7.8, 1.2 Hz), 6.95 (2H, td, J=7.8, 1.2 Hz), 3.73 (1H, t, J=9.0 Hz), 3.48-3.52 (1H, m), 3.28-3.33 (1H, m), 2.16-2.20 (1H, m), 1.89-1.93 (1H, m), 1.68-1.73 (2H, m), 1.36 (1H, qt, J=13.8, 3.0 Hz), 1.22 (1H, qd, J=13.2, 3.6 Hz); $^{13}$C NMR (150 MHz, CD$_3$OD) δ 147.0, 131.5, 128.4, 128.0, 124.5, 123.5, 77.0, 73.0, 67.8, 32.4, 31.6, 23.5; LCMS m/z 339.1260 ([M+H$^+$], C$_{18}$H$_{18}$N$_4$OS requires 339.1274).

Example 20e (1S,2R,6S)-rel-2-amino-6-(10H-phenothiazin-10-yl)cyclohexanol

A solution of (1R,2R,6S)-rel-2-azido-6-(10H-phenothiazin-10-yl)cyclohexanol (0.630 g, 1.87 mmol) was dissolved in THF (10.0 mL), treated with PPh$_3$ (0.586 g, 2.23 mmol), H$_2$O (0.5 mL), and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene to afford the title compound as a beige foam (0.464 g, 80%). $^1$H NMR (600 MHz, CD$_3$OD) δ 7.28 (2H, d, J=8.4 Hz), 7.15 (2H, td, J=9.0, 1.2 Hz), 7.09 (2H, dd, J=7.8, 1.2 Hz), 6.97 (2H, td, J=7.8, 1.2 Hz), 3.58 (1H, t, J=10.2 Hz), 3.46-3.51 (1H, m), 2.65 (1H, ddd, J=13.2, 9.0, 4.2 Hz), 2.20-2.25 (1H, m), 1.84-1.87 (1H, m), 1.77 (1H, qd, J=13.2, 3.6 Hz), 1.72-1.75 (1H, m), 1.39 (1H, qt, J=13.2, 3.6 Hz), 1.21 (1H, qd, J=13.2, 3.6 Hz); $^{13}$C NMR (150 MHz, CD$_3$OD) δ 146.9, 131.3, 128.4, 128.0, 124.9, 123.4, 78.0, 73.3, 57.4, 33.1, 32.9, 24.1; LCMS m/z 313.2201 ([M+H$^+$], C$_{18}$H$_{20}$N$_2$OS requires 313.1369).

-continued

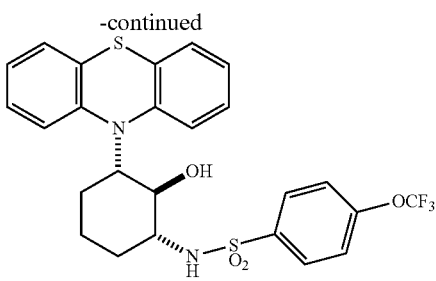

Example 20

N-((1R,2R,3S)-rel-2-hydroxy-3-(10H-phenothiazin-10-yl)cyclohexyl)-4-(trifluoromethoxy)benzenesulfonamide A solution of (1S,2R,6S)-rel-2-amino-6-(10H-phenothiazin-10-yl)cyclohexanol (0.065 g, 0.208 mmol) in DMF (1.0 mL) was cooled to 0° C., treated with Et₃N (29.0 μL, 0.208 mmol), and 4-trifluoromethoxybenzenesulfonyl chloride (35.0 μL, 0.208 mmol). The mixture was warmed to 25° C., and stirred for 2 h. The mixture was partitioned between saturated aqueous NaCl (50 mL) and CH₂Cl₂ (100 mL). The organic layer was washed with saturated aqueous NaCl (3×50 mL), dried (Na₂SO₄), and concentrated in vacuo. The residue was dissolved in a minimal amount of CH₂Cl₂ and purified by flash chromatography (SiO₂, 0-20% ethyl acetate-hexanes). The pure fractions were combined, concentrated, and the residue was dissolved in a minimal amount of ethyl acetate and precipitated with the addition of hexanes to afford the title compound as a white solid (0.084 g, 76%). ¹H NMR (600 MHz, CD₃OD) δ 8.00 (2H, d, J=9.0 Hz), 7.42 (2H, d, J=8.4 Hz), 7.22 (2H, dd, J=8.4, 1.2 Hz), 7.14 (2H, td, J=7.2, 1.2 Hz), 7.06 (2H, dd, J=7.2, 1.2 Hz), 6.96 (2H, td, J=7.2, 1.2 Hz), 3.64 (1H, t, J=9.6 Hz), 3.44 (1H, ddd, J=12.6, 10.2, 4.2 Hz), 3.10 (1H, ddd, J=11.4, 9.6, 4.8 Hz), 2.15-2.18 (1H, m), 1.75-1.79 (1H, m), 1.68 (1H, qd, J=12.6, 3.6 Hz), 1.59-1.63 (1H, m), 1.21-1.31 (2H, m); ¹³C NMR (150 MHz, CD₃OD) δ 152.9, 146.7, 142.2, 131.4, 130.5, 128.4, 127.9, 124.9, 123.5, 122.0, 120.9, 75.2, 73.4, 60.4, 33.7, 32.4, 23.7; LCMS m/z 537.1246 ([M+H]⁺, C₂₅H₂₃F₃N₂O₄S₂ requires 537.1124).

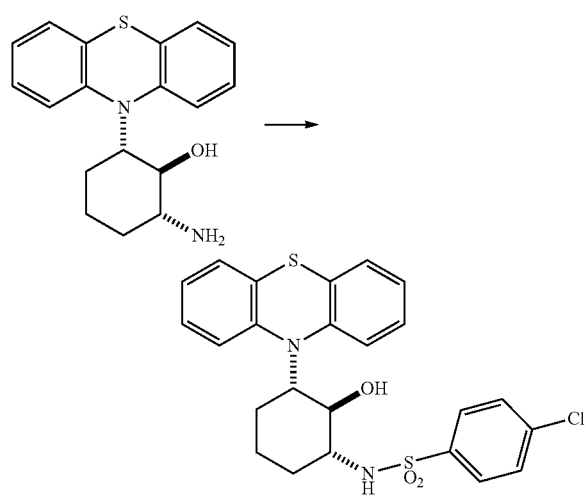

Example 21

4-chloro-N-((1R,2R,3S)-rel-2-hydroxy-3-(10H-phenothiazin-10-yl)cyclohexyl)benzenesulfonamide A solution of (1S,2R,6S)-rel-2-amino-6-(10H-phenothiazin-10-yl)cyclohexanol (0.065 g, 0.208 mmol) in DMF (1.0 mL) was cooled to 0° C., treated with Et₃N (29.0 μL, 0.208 mmol), and 4-chlorobenzenesulfonyl chloride (0.044 g, 0.208 mmol). The mixture was warmed to 25° C., and stirred for 2 h. The mixture was partitioned between saturated aqueous NaCl (50 mL) and CH₂Cl₂ (100 mL). The organic layer was washed with saturated aqueous NaCl (3×50 mL), dried (Na₂SO₄), and concentrated in vacuo. The residue was dissolved in a minimal amount of CH₂Cl₂ and purified by flash chromatography (SiO₂, 0-20% ethyl acetate-hexanes). The pure fractions were combined, concentrated, and the residue was dissolved in a minimal amount of ethyl acetate and precipitated with the addition of hexanes to afford the title compound as a white solid (0.078 g, 77%). ¹H NMR (600 MHz, CD₃OD) δ 7.87 (2H, dt, J=9.0, 2.4 Hz), 7.53 (2H, dt, J=8.4, 1.8 Hz), 7.22 (2H, dd, J=7.8, 1.2 Hz), 7.14 (2H, td, J=7.2, 1.2 Hz), 7.06 (2H, dd, J=7.8, 1.8 Hz), 6.96 (2H, td, J=7.8, 1.2 Hz), 3.64 (1H, t, J=9.6 Hz), 3.43 (1H, ddd, J=12.6, 10.2, 3.6 Hz), 3.07 (1H, ddd, J=11.4, 9.0, 4.2 Hz), 2.15-2.18 (1H, m), 1.73-1.76 (1H, m), 1.66 (1H, qd, J=9.0, 3.6 Hz), 1.60-1.64 (1H, m), 1.18-1.30 (2H, m); ¹³C NMR (150 MHz, CD₃OD) δ 146.7, 142.1, 139.5, 131.5, 130.2, 129.9, 128.4, 127.9, 125.0, 123.5, 75.3, 73.4, 60.4, 33.6, 32.4, 23.7; LCMS m/z 487.0894 ([M+H]⁺, C₂₄H₂₃ClN₂O₃S₂ requires 487.0911

Example 22

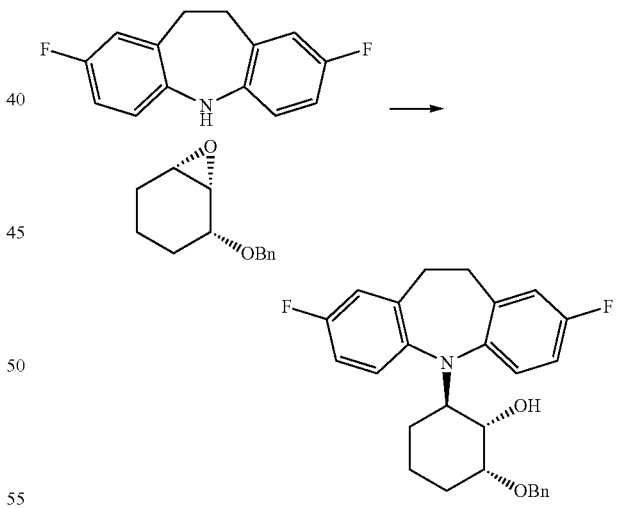

(1S,2R,6R)-2-(benzyloxy)-6-(2,8-difluoro-10,11-dihydro-5H-dibenzo[b,f]azepin-5-yl)cyclohexanol A solution of 2,8-difluoro-10,11-dihydro-5H-dibenzo[b,f]azepine (1.00 g, 4.32 mmol) in toluene (5.0 mL) was treated with NaH (60% dispersion in mineral oil (0.345 g, 0.865 mmol) at 25° C. and stirred for 0.5 h. The mixture was then treated with (1S,2R,6S)-2-(benzyloxy)-7-oxabicyclo[4.1.0]heptane (0.882 g, 4.32 mmol) and heated to 100° C. for 14 h. The vessel was cooled, treated with a solution of saturated ammonium chloride (50 mL), and then extracted with toluene (3×50 mL). The combined organic layers were washed with saturated aqueous NaCl (100 mL), dried (Na₂SO₄), and concentrated in vacuo. The residue was dissolved in a minimal amount of toluene and purified by flash chromatography (SiO₂, 0-10% ethyl acetate-hexanes) to afford the title compound as a white foam (1.59 g, 85%). ¹H NMR (600 MHz, CDCl₃) δ 7.31-7.38 (3H, m), 7.24 (2H, d, J=7.2 Hz), 7.22 (1H, br s), 7.17 (1H, br s), 6.78-6.81 (2H, br m), 6.77 (2H, dd, J=9.0, 2.4 Hz), 4.53 (1H, d, J=12.0 Hz), 4.42 (1H, d, J=12.0 Hz), 4.11-4.14 (1H, m), 3.80-3.84 (1H, br s), 3.77-3.78 (1H, m), 3.48-3.50 (1H, br s), 3.28-3.35 (1H, br s), 2.59-2.71 (2H, m), 2.50 (1H, d, J=4.8 Hz), 2.03-2.07 (1H, m), 1.84-1.88 (1H, m), 1.44-1.57 (2H, m), 1.37-1.42 (2H, m); LCMS m/z 436.2085 ([M+H⁺], $C_{27}H_{27}F_2NO_2$ requires 436.2083).

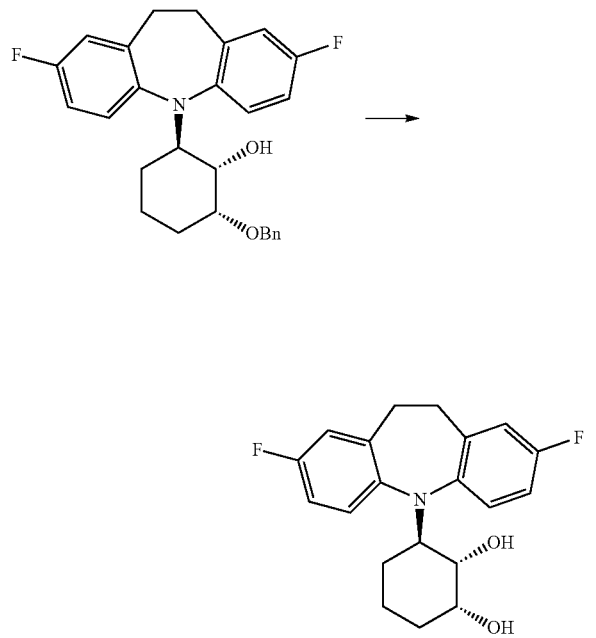

(1R,2S,3R)-3-(2,8-difluoro-10,11-dihydro-5H-dibenzo[b,f]azepin-5-yl)cyclohexane-1,2-diol A solution of (1S,2R,6R)-2-(benzyloxy)-6-(2,8-difluoro-10,11-dihydro-5H-dibenzo[b,f]azepin-5-yl)cyclohexanol (1.57 g, 3.60 mmol) in THF:MEOH (1:1, 10.0 mL) was treated with 10% Pd/C (0.393 g, 0.370 mmol) and then placed under an atmosphere of H₂ (g). The mixture was stirred for 14 h at 25° C. then filtered thru Celite and concentrated in vacuo. The residue was dissolved in a minimal amount of CH₂Cl₂ and purified by flash chromatography (SiO₂, 0-50% ethyl acetate-hexanes) to afford the title compound as a white solid (1.28 g, 99%). ¹H NMR (600 MHz, CDCl₃) δ 7.14-7.23 (2H, br s), 6.78-6.84 (4H, m), 4.13-4.15 (1H, m), 4.04 (1H, td, J=9.0, 3.0 Hz), 3.64 (1H, d, J=6.6 Hz), 3.43-3.49 (1H, br s), 3.34-3.42 (1H, br s), 2.67-2.83 (3H, br m), 2.29-2.38 (1H, br m), 2.08-2.11 (1H, m), 1.78-1.80 (1H, m), 1.57-1.64 (1H, m), 1.43-1.46 (1H, m), 1.38-1.43 (1H, m), 1.32-1.36 (2H, m); LCMS m/z 346.1613 ([M+H⁺], $C_{20}H_{21}F_2NO_2$ requires 346.1613).

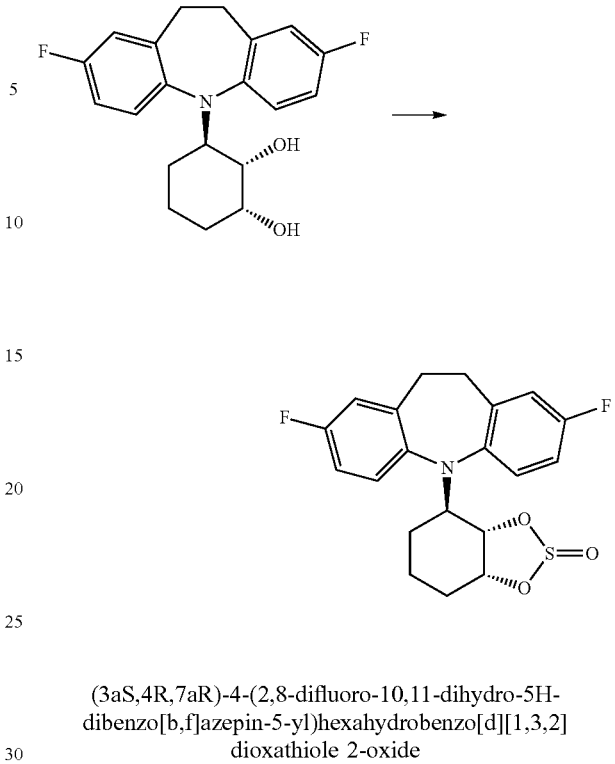

(3aS,4R,7aR)-4-(2,8-difluoro-10,11-dihydro-5H-dibenzo[b,f]azepin-5-yl)hexahydrobenzo[d][1,3,2]dioxathiole 2-oxide A solution of (1R,2S,3R)-3-(2,8-difluoro-10,11-dihydro-5H-dibenzo[b,f]azepin-5-yl)cyclohexane-1,2-diol (1.26 g, 3.65 mmol) in CH₂Cl₂ (10.0 mL) was cooled to 0° C., treated with triethylamine (4.05 mL, 29.2 mmol) and then treated dropwise with thionyl chloride (0.80 mL, 10.94 mmol). The mixture was warmed to 25° C., stirred for 2 h, and then poured over H₂O (200 mL). The aqueous layer was extracted with CH₂Cl₂ (2×100 mL) and then the combined organic layers were washed with H₂O (2×100 mL), dried (Na₂SO₄), and concentrated in vacuo. The residue was dissolved in a minimal amount of CH₂Cl₂ and purified by flash chromatography (SiO₂, 0-15% ethyl acetate-hexanes) to afford the title compound, a mixture of sulfite diastereoisomers, as a clear foam (0.990 g, 69%). ¹H NMR (600 MHz, CDCl₃) δ 7.12-7.15 (1H, m), 7.07 (1H, br s), 1H [5.08-5.09 (m), 4.99 (s), 4.76-4.78 (m), 4.64-4.65 (m)], 1H [4.52 (dd, J=9.0, 4.8 Hz), 4.49 (ddd, J=12.6, 9.0, 3.6 Hz), 4.31 (dd, J=9.6, 5.4 Hz)], 1H [3.72-3.78 (1H, br m), 3.62 (1H, ddd, J=12.0, 9.0, 3.6 Hz), 3.53-3.57 (m), 3.42 (br s), 3.32-3.38 (br m)], 2H [2.71-2.80 (m), 2.65-2.70 (m)], 2H [2.32-2.39 (m), 2.24-2.30 (m)], 6H[1.68-1.83 (m), 1.60-1.66 (m), 1.56-1.60 (m), 1.47-1.55 (m)]; LCMS m/z 392.1123 ([M+H⁺], $C_{20}H_{19}F_2NO_3S$ requires 392.1126).

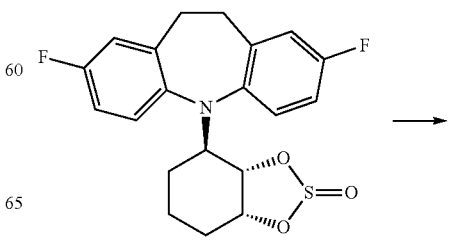

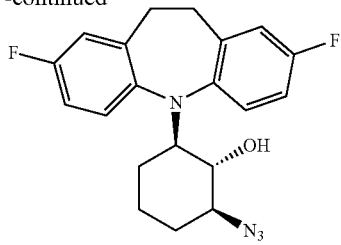

(1S,2S,6R)-2-azido-6-(2,8-difluoro-10,11-dihydro-5H-dibenzo[b,f]azepin-5-yl)cyclohexanol A solution of (3aS,4R,7aR)-4-(2,8-difluoro-10,11-dihydro-5H-dibenzo[b,f]azepin-5-yl)hexahydrobenzo[d][1,3,2]dioxathiole 2-oxide (0.990 g, 2.53 mmol) in DMF (5.0 mL) was treated with NaN$_3$ (0.494 g, 7.59 mmol) and heated to 100° C. for 14 h under microwave irradiation. The mixture was cooled to 25° C., poured over a solution of saturated aqueous NaCl (100 mL), and extracted with CH$_2$Cl$_2$ (3×100 mL). The combined organic layers were washed with H$_2$O (3×100 mL), saturated aqueous NaCl (100 mL), dried (Na$_2$SO$_4$), and concentrated in vacuo. The residue was suspended in a minimal amount of CH$_2$Cl$_2$ and purified by flash chromatography (SiO$_2$, 0-10% ethyl acetate-hexanes) to afford the title compound as a beige oil (0.616 g, 66%). $^1$H NMR (600 MHz, CDCl$_3$) δ 7.48 (1H, br s), 7.23 (1H, br s), 6.81-6.90 (3H, br m), 6.72 (1H, br s), 3.56 (1H, ddd, J=13.2, 9.6, 3.6 Hz), 3.46-3.53 (1H, br m), 3.38-3.44 (2H, m), 3.29 (1H, br m), 2.86 (1H, s), 2.77-2.83 (1H, br m), 2.63-2.70 (1H, br s), 2.12-2.15 (1H, m), 1.97-2.01 (1H, m), 1.75 (1H, dt, J=13.8, 3.0 Hz), 1.33 (1H, qt, J=13.2, 3.6 Hz), 1.25 (2H, quintet of doublets, J=12.6, 3.6 Hz); LCMS m/z 371.1676 ([M+H$^+$], C$_{20}$H$_{20}$F$_2$N$_4$O requires 371.1678).

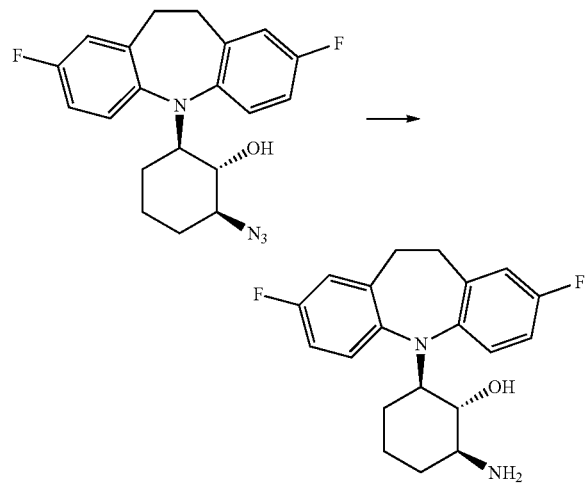

(1R,2S,6R)-2-amino-6-(2,8-difluoro-10,11-dihydro-5H-dibenzo[b,f]azepin-5-yl)cyclohexanol A solution of (1S,2S,6R)-2-azido-6-(2,8-difluoro-10,11-dihydro-5H-dibenzo[b,f]azepin-5-yl)cyclohexanol (0.616 g, 1.66 mmol) in THF (10.0 mL) was cooled to 0° C., treated with PPh$_3$ (0.611 g, 2.33 mmol), H$_2$O (0.2 mL), and stirred for 14 h at 25° C. The solution was concentrated to dryness, dissolved in a minimal amount of CH$_2$Cl$_2$ and purified by flash chromatography (SiO$_2$, 0-20% ethyl acetate-hexanes to remove nonpolar impurities followed by 3% MeOH—CH$_2$Cl$_2$ to remove triphenylphosphine oxide and then 17:2:1 CH$_2$Cl$_2$:MeOH:NH$_4$OH to elute the product). The combined fractions of pure product were concentrated, dried azeotropically with toluene to afford the title compound as a beige oil (0.589 g, 99%). $^1$H NMR (600 MHz, CDCl$_3$) δ (as a mixture of conformers) 1H [8.24 (dd, J=11.4, 7.8 Hz), 8.10-8.14 (m)], 1H [8.03 (td, J=7.8, 2.4 Hz), 7.88 (br s), 7.84 (1H, t, J=7.8 Hz), 1H [7.75 (d, J=7.2 Hz), 7.40 (t, J=7.2 Hz)], 7.37 (1H, td, J=8.4, 2.4 Hz), 1H [7.42 (br s), 7.27 (br s)], 4.12 (1H, td, J=12.6, 3.6 Hz), 4.04-4.09 (1H, br s), 3.83-3.92 (1H, br m), 3.76 (1H, t, J=9.6 Hz), 3.31-3.40 (1H, br m), 3.25 (1H, td, J=12.0, 3.6 Hz), 3.15-3.35 (H, br m), 2.94 (1H, s), 2.65 (1H, d, J=12.0 Hz), 2.38 (1H, d, J=12.0 Hz), 2.21 (1H, d, J=10.8 Hz), 1.87 (1H, qt, J=13.2, 3.6 Hz); 1.77 (1H, qd, J=12.6, 3.6 Hz); 1.64 (1H, dd, J=13.2, 7.8 Hz); LCMS m/z 345.1773 ([M+H$^+$], C$_{20}$H$_{22}$F$_2$N$_2$O requires 345.1773).

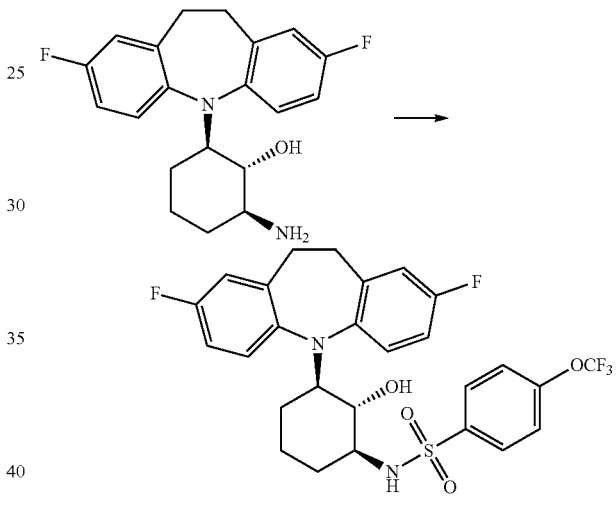

N-((1S,2S,3R)-3-(2,8-difluoro-10,11-dihydro-5H-dibenzo[b,f]azepin-5-yl)-2-hydroxycyclohexyl)-4-(trifluoromethoxy)benzenesulfonamide A solution of (1R,2S,6R)-2-amino-6-(2,8-difluoro-10,11-dihydro-5H-dibenzo[b,f]azepin-5-yl)cyclohexanol (0.150 g, 0.436 mmol) in DMF (1.0 mL) was cooled to 0° C., treated with Et$_3$N (60.0 µL, 0.436 mmol), and 4-trifluoromethoxybenzenesulfonyl chloride (74.0 µL, 0.436 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-35% ethyl acetate-hexanes) to afford the title compound Example 22 as a white foam (0.192 g, 77%). $^1$H NMR (600 MHz, CDCl$_3$) δ 7.95 (2H, d, J=8.4 Hz), 7.37 (1H, br s), 7.34 (2H, d, J=8.4 Hz), 7.16 (1H, br s), 6.82 (1H, br s), 6.77 (2H, br s), 6.69 (1H, br s), 5.05 (1H, d, J=6.6 Hz), 3.48 (1H, td, J=10.8, 3.6 Hz), 3.40-3.46 (1H, br m), 3.30 (1H, td, J=9.6, 1.8 Hz), 3.26 (1H, br s), 3.10-3.16 (1H, m), 3.09 (1H, d, J=1.8 Hz), 2.71-2.78 (1H, br m), 2.60-2.66 (1H, br s), 2.05-2.07 (1H, m), 1.70-1.72 (1H, m), 1.56-1.60 (1H, m), 1.22-1.27 (1H, m), 1.12-1.18 (2H, m), 1.00-1.08 (1H, m); LCMS m/z 569.1524 ([M+H$^+$], C$_{27}$H$_{25}$F$_5$N$_2$O$_4$S requires 569.1528).

Example 23, from Chiral Material

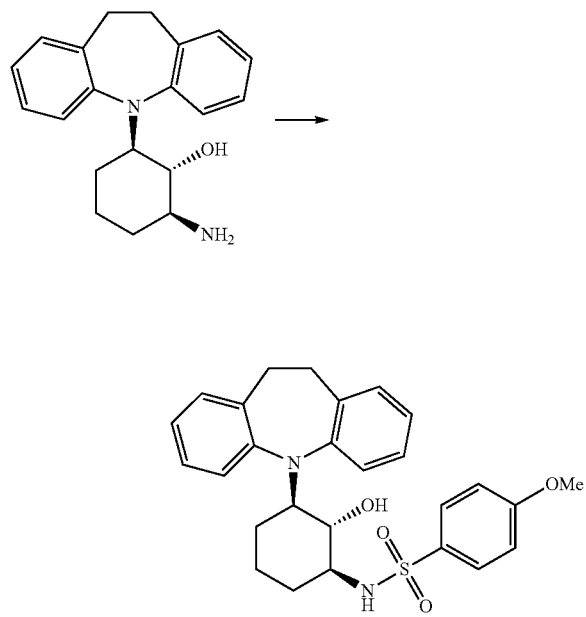 [SMILES: N[C@H]1CCC[C@@H](N2c3ccccc3CCc3ccccc32)[C@@H]1O ; COc1ccc(S(=O)(=O)N[C@H]2CCC[C@@H](N3c4ccccc4CCc4ccccc43)[C@@H]2O)cc1]

N-((1S,2S,3R)-3-(10,11-dihydro-5H-dibenzo[b,f]azepin-5-yl)-2-hydroxycyclohexyl)-4-methoxybenzenesulfonamide A solution of (1R,2S,6R)-2-amino-6-(10,11-dihydro-5H-dibenzo[b,f]azepin-5-yl)cyclohexanol (0.100 g, 0.324 mmol) in DMF (1.0 mL) was cooled to 0° C., treated with Et$_3$N (45.0 μL, 0.324 mmol), and 4-methoxybenzenesulfonyl chloride (0.067 g, 0.324 mmol). The mixture was warmed to 25° C., and stirred for 2 h. The mixture was partitioned between saturated aqueous NaCl (100 mL), and CH$_2$Cl$_2$ (300 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-25% ethyl acetate-hexanes). The purified fractions were combined, dissolved in a minimal amount of ethyl ether, and could either be recrystallized or precipitated with the addition of hexanes to afford the title compound as a white solid (0.115 g, 74%). $^1$H NMR (600 MHz, CDCl$_3$) δ 7.84 (2H, d, J=9.0 Hz), 7.32-7.52 (1H, br m), 7.13 (3H, t, J=8.4 Hz), 7.02-7.12 (2H, br m), 7.00 (2H, d, J=9.0 Hz), 6.88-7.02 (2H, br m), 4.91 (1H, d, J=5.4 Hz), 3.89 (3H, s), 3.64 (1H, td, J=10.8, 3.0 Hz), 3.36 (1H, td, J=9.0, 1.2 Hz), 3.20-3.60 (2H, br m), 3.04-3.10 (1H, m), 3.04 (1H, s), 2.11-2.13 (1H, m), 1.78-1.81 (1H, m), 1.55-1.58 (1H, m), 1.12-1.25 (2H, m), 1.06 (1H, qd, J=11.4, 3.6 Hz); $^{13}$C NMR (150 MHz, CDCl$_3$) δ 152.2, 141.1, 129.9, 129.6, 126.5, 126.4, 123.4, 121.7, 121.3, 120.0, 118.3, 74.4, 68.6, 59.3, 33.1, 31.8, 30.3, 22.1; LCMS m/z 479.2350 ([M+H$^+$], C$_{27}$H$_{30}$N$_2$O$_4$S requires 479.1999).

Example 24

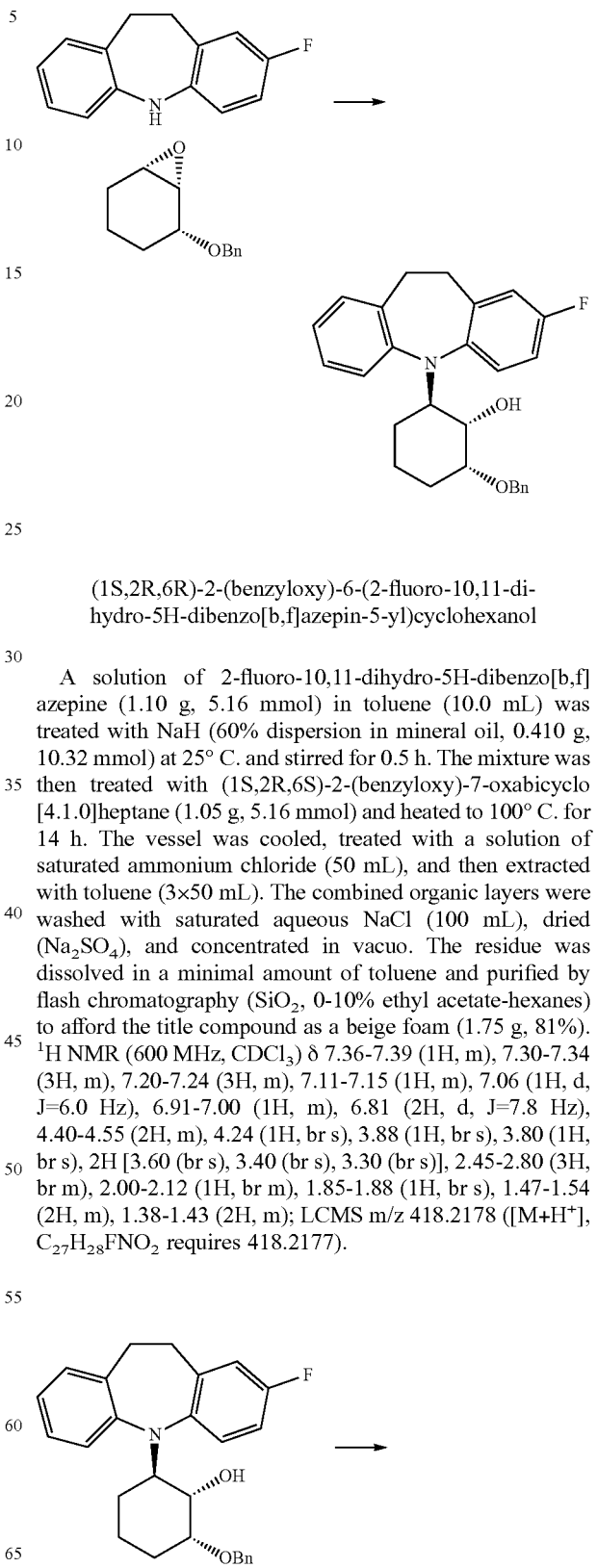

(1S,2R,6R)-2-(benzyloxy)-6-(2-fluoro-10,11-dihydro-5H-dibenzo[b,f]azepin-5-yl)cyclohexanol A solution of 2-fluoro-10,11-dihydro-5H-dibenzo[b,f]azepine (1.10 g, 5.16 mmol) in toluene (10.0 mL) was treated with NaH (60% dispersion in mineral oil, 0.410 g, 10.32 mmol) at 25° C. and stirred for 0.5 h. The mixture was then treated with (1S,2R,6S)-2-(benzyloxy)-7-oxabicyclo[4.1.0]heptane (1.05 g, 5.16 mmol) and heated to 100° C. for 14 h. The vessel was cooled, treated with a solution of saturated ammonium chloride (50 mL), and then extracted with toluene (3×50 mL). The combined organic layers were washed with saturated aqueous NaCl (100 mL), dried (Na$_2$SO$_4$), and concentrated in vacuo. The residue was dissolved in a minimal amount of toluene and purified by flash chromatography (SiO$_2$, 0-10% ethyl acetate-hexanes) to afford the title compound as a beige foam (1.75 g, 81%). $^1$H NMR (600 MHz, CDCl$_3$) δ 7.36-7.39 (1H, m), 7.30-7.34 (3H, m), 7.20-7.24 (3H, m), 7.11-7.15 (1H, m), 7.06 (1H, d, J=6.0 Hz), 6.91-7.00 (1H, m), 6.81 (2H, d, J=7.8 Hz), 4.40-4.55 (2H, m), 4.24 (1H, br s), 3.88 (1H, br s), 3.80 (1H, br s), 2H [3.60 (br s), 3.40 (br s), 3.30 (br s)], 2.45-2.80 (3H, br m), 2.00-2.12 (1H, br m), 1.85-1.88 (1H, br s), 1.47-1.54 (2H, m), 1.38-1.43 (2H, m); LCMS m/z 418.2178 ([M+H$^+$], C$_{27}$H$_{28}$FNO$_2$ requires 418.2177).

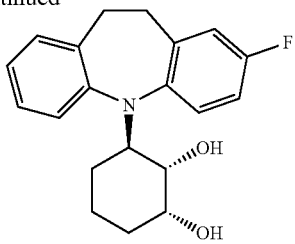

(1R,2S,3R)-3-(2-fluoro-10,11-dihydro-5H-dibenzo[b,f]azepin-5-yl)cyclohexane-1,2-diol A solution of (1S,2R,6R)-2-(benzyloxy)-6-(2-fluoro-10,11-dihydro-5H-dibenzo[b,f]azepin-5-yl)cyclohexanol (1.73 g, 4.14 mmol) in THF:MEOH (1:1, 15.0 mL) was treated with 10% Pd/C (0.433 g) and then placed under an atmosphere of H$_2$ (g). The mixture was stirred for 14 h at 25° C. then filtered thru Celite and concentrated in vacuo. The residue was dissolved in a minimal amount of CH$_2$Cl$_2$ and purified by flash chromatography (SiO$_2$, 0-50% ethyl acetate-hexanes) to afford the title compound as a white solid (1.28 g, 94%). $^1$H NMR (600 MHz, CDCl$_3$) δ 7.23-7.30 (1H, m), 7.16-7.22 (1H, m), 7.14 (1H, t, J=7.2 Hz), 7.07 (1H, d, J=6.6 Hz), 6.92-7.01 (1H, m), 6.81 (2H, td, J=8.4, 2.4 Hz), 4.17 (1H, br s), 4.11-4.15 (1H, m), 3.65 (1H, d, J=6.6 Hz), 3.25-3.55 (2H, br m), 2.63-2.91 (3H, br m), 2.38 (1H, br s), 2.12 (1H, br s), 1.17-1.83 (1H, m), 1.59-1.70 (1H, m), 1.44-1.47 (1H, m), 1.39-1.44 (1H, m); LCMS m/z 328.1711 ([M+H$^+$], C$_{20}$H$_{22}$FNO$_2$ requires 328.1707).

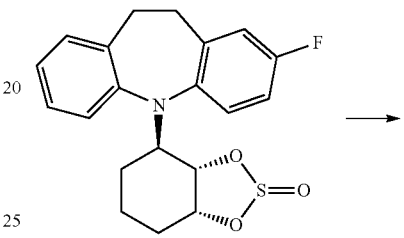

(3aS,4R,7aR)-4-(2-fluoro-10,11-dihydro-5H-dibenzo[b,f]azepin-5-yl)hexahydrobenzo[d][1,3,2]dioxathiole 2-oxide A solution of (1R,2S,3R)-3-(2-fluoro-10,11-dihydro-5H-dibenzo[b,f]azepin-5-yl)cyclohexane-1,2-diol (1.26 g, 3.84 mmol) in CH$_2$Cl$_2$ (10.0 mL) was cooled to 0° C., treated with triethylamine (4.26 mL, 30.7 mmol) and then treated dropwise with thionyl chloride (0.84 mL, 11.5 mmol). The mixture was warmed to 25° C., stirred for 2 h, and then poured over H$_2$O (200 mL). The aqueous layer was extracted with CH$_2$Cl$_2$ (2×100 mL) and then the combined organic layers were washed with H$_2$O (2×100 mL), dried (Na$_2$SO$_4$), and concentrated in vacuo. The residue was dissolved in a minimal amount of CH$_2$Cl$_2$ and purified by flash chromatography (SiO$_2$, 0-15% ethyl acetate-hexanes) to afford the title compound, a mixture of sulfite diastereoisomers, as a brown foam (1.25 g, 87%). $^1$H NMR (600 MHz, CDCl$_3$) δ (as a mixture of diastereoisomers) 7.03-7.23 (4H, m), 6.95 (1H, br s), 6.92 (1H, br s), 6.80-6.86 (2H, m), 1H [5.08 (br s), 4.64 (d, J=4.2 Hz)], 1H [4.56 (td, J=12.0, 9.0, 3.6 Hz), 3.72 (td, J=12.0, 9.6, 3.0 Hz)], 1H [4.50 (1H, br s), 3.84 (1H, br s)], 1H [4.32-4.36 (m), 3.33-3.39 (m)], 2.74-2.85 (4H, m), 2.36-2.40 (1H, m), 2.28 (1H, t, J=16.2 Hz), 1.53-1.84 (4H, m); LCMS m/z 374.1215 ([M+H$^+$], C$_{20}$H$_{20}$FNO$_3$S requires 374.1221).

(1S,2S,6R)-2-azido-6-(2-fluoro-10,11-dihydro-5H-dibenzo[b,f]azepin-5-yl)cyclohexanol A solution of (3aS,4R,7aR)-4-(2-fluoro-10,11-dihydro-5H-dibenzo[b,f]azepin-5-yl)hexahydrobenzo[d][1,3,2]dioxathiole 2-oxide (1.25 g, 3.35 mmol) in DMF (5.0 mL) was treated with NaN$_3$ (0.654 g, 10.0 mmol) and heated to 100° C. for 14 h under microwave irradiation. The mixture was cooled to 25° C., poured over a solution of saturated aqueous NaCl (100 mL), and extracted with CH$_2$Cl$_2$ (3×100 mL). The combined organic layers were washed with H$_2$O (3×100 mL), saturated aqueous NaCl (100 mL), dried (Na$_2$SO$_4$), and concentrated in vacuo. The residue was suspended in a minimal amount of CH$_2$Cl$_2$ and purified by flash chromatography (SiO$_2$, 0-10% ethyl acetate-hexanes) to afford the title compound as a beige oil (0.643 g, 54%). $^1$H NMR (600 MHz, CDCl$_3$) δ 7.35-7.57 (1H, br m), 7.23 (1H, br s), 7.17 (1H, t, J=7.2 Hz), 6.99-7.12 (1H, br m), 6.90 (1H, br s), 6.85 (1H, t, J=7.2 Hz), 6.75-7.83 (1H, m); 3.66 (1H, br s), 3.37-3.53 (2H, m), 3.27 (1H, br s), 2.63-3.00 (3H, m), 2.16 (1H, br s), 1.98 (1H, d, J=12.6 Hz), 1.74 (1H, d, J=12.6 Hz), 1.26-1.33 (2H, m), 1.20-1.26 (1H, m); LCMS m/z 353.1767 ([M+H$^+$], C$_{20}$H$_{21}$FN$_4$O requires 353.1772).

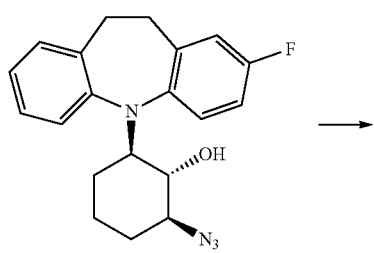

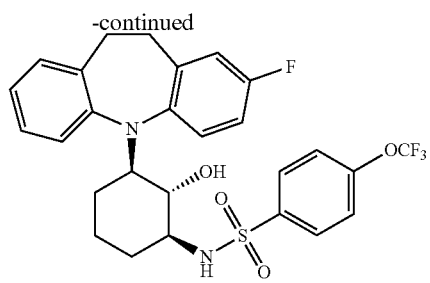

N-((1S,2S,3R)-3-(2-fluoro-10,11-dihydro-5H-dibenzo[b,f]azepin-5-yl)-2-hydroxycyclohexyl)-4-(trifluoromethoxy)benzenesulfonamide A solution of (1R,2S,6R)-2-amino-6-(2-fluoro-10,11-dihydro-5H-dibenzo[b,f]azepin-5-yl)cyclohexanol (0.150 g, 0.460 mmol) in DMF (1.0 mL) was cooled to 0° C., treated with Et₃N (64.0 μL, 0.460 mmol), and 4-trifluoromethoxy-benzenesulfonyl chloride (78.0 μL, 0.460 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (3×50 mL), dried (Na₂SO₄), and concentrated in vacuo. The residue was dissolved in a minimal amount of CH₂Cl₂ and purified by flash chromatography (SiO₂, 0-35% ethyl acetate-hexanes) to afford the title compound Example 24 as a white foam (0.146 g, 58%). ¹H NMR (600 MHz, CDCl₃) δ 7.93-8.01 (2H, m), 7.36 (2H, d, J=8.4 Hz), 7.13 (3H, t, J=7.2 Hz), 6.97-7.10 (1H, br s), 6.73-6.95 (3H, m), 5.02 (1H, d, J=6.0 Hz), 3.58 (1H, br s), 3.38-3.52 (1H, m), 3.34 (1H, t, J=9.6 Hz), 2H [3.27 (br s), 3.15 (br s), 3.06 (1H, br s)], 2.67-2.95 (3H, m), 2.05-2.15 (1H, br m), 1.83 (1H, d, J=12.6 Hz), 1.25-1.35 (1H, m), 1.15-1.25 (2H, m), 1.09-1.15 (1H, m); LCMS m/z 551.1611 ([M+H⁺], C₂₇H₂₆F₄N₂O₄S requires 551.1622).

Example 25

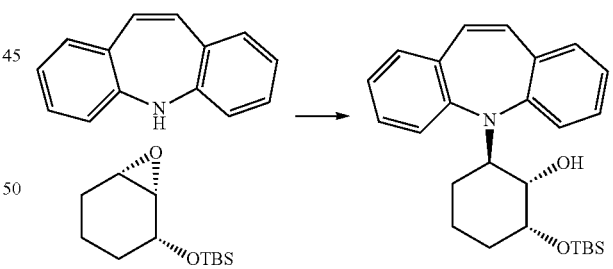

(1R,2S,6R)-2-amino-6-(2-fluoro-10,11-dihydro-5H-dibenzo[b,f]azepin-5-yl)cyclohexanol

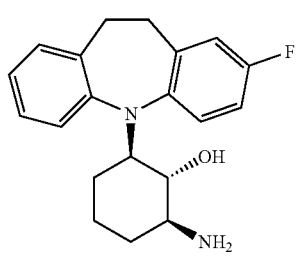

A solution of (1S,2S,6R)-2-azido-6-(2-fluoro-10,11-dihydro-5H-dibenzo[b,f]azepin-5-yl)cyclohexanol (0.643 g, 1.83 mmol) in THF (10.0 mL) was cooled to 0° C., treated with PPh₃ (0.718 g, 2.74 mmol), H₂O (0.25 mL), and stirred for 14 h at 25° C. The solution was concentrated to dryness, dissolved in a minimal amount of CH₂Cl₂ and purified by flash chromatography (SiO₂, 0-20% ethyl acetate-hexanes to remove nonpolar impurities followed by 3% MeOH—CH₂Cl₂ to remove triphenylphosphine oxide and then 17:2:1 CH₂Cl₂:MeOH:NH₄OH to elute the product). The combined fractions of pure product were concentrated, dried azeotropically with toluene to afford the title compound as a beige foam (0.627 g, 99%). ¹H NMR (600 MHz, CDCl₃) δ (as a mixture of conformers) 1H [7.91-7.94 (m), 7.72 (m), 7.62-7.66 (m)], 1H [7.69 (d, J=12.0 Hz), 7.68 (dd, J=12.0, 1.1 Hz)], 7.56 (1H, td, J=7.5, 1.4 Hz), 7.47 (1H, td, J=7.7, 2.8 Hz), 1H [7.29-7.37 (m), 7.27 (t, J=7.8 Hz)], 7.17-7.20 (1H, m), 7.15 (1H, t, J=7.3 Hz), 1H [6.98-7.06 (br m), 6.84-6.92 (br s)], 6.82 (1H, td, J=8.4, 2.8 Hz), 3.64 (1H, br s), 3.34-3.58 (1H, m), 3.19 (1H, t, J=9.6 Hz), 2.86 (1H, br s), 2.65-2.73 (2H, br m), 2.37 (1H, s), 2.10 (1H, br s), 1.79-1.81 (1H, m), 1.62-1.64 (1H, m), 1.26-1.37 (1H, m), 1.10-1.25 (1H, m), 1.04 (1H, qd, J=13.2, 4.2 Hz); LCMS m/z 327.1862 ([M+H⁺], C₂₀H₂₃FN₂O requires 327.1867).

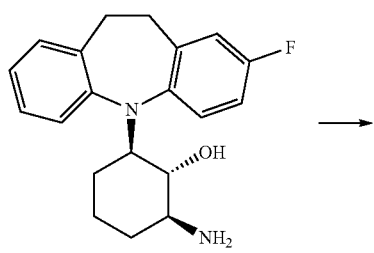

rac-(1S,2R,6R)-2-((tert-butyldimethylsilyl)oxy)-6-(5H-dibenzo[b,f]azepin-5-yl)cyclohexanol A solution of 5H-dibenzo[b,f]azepine (1.50 g, 7.76 mmol) in toluene (10.0 mL) was treated with NaH (60% dispersion in mineral oil (0.621 g, 15.5 mmol) at 25° C. and stirred for 0.5 h. The mixture was then treated with ((1S,2R,6S)-7-oxabicyclo[4.1.0]heptan-2-yloxy)(tert-butyl)dimethylsilane (1.95 g, 8.54 mmol) and heated to 100° C. for 14 h. The vessel was cooled, treated with a solution of saturated ammonium chloride (50 mL), and then extracted with toluene (3×50 mL). The combined organic layers were washed with saturated aqueous NaCl (100 mL), dried (Na$_2$SO$_4$), and concentrated in vacuo. The residue was dissolved in a minimal amount of toluene and purified by flash chromatography (SiO$_2$, 0-10% ethyl acetate-hexanes) to afford the title compound as a beige oil (2.50 g, 76%). $^1$H NMR (600 MHz, CDCl$_3$) δ 7.29-7.33 (3H, m), 7.17 (2H, d, J=7.8 Hz), 7.16 (1H, d, J=7.8 Hz), 7.08 (2H, t, J=7.2 Hz), 6.85 (2H, q, J=11.4 Hz), 4.27 (1H, br s), 3.92-3.94 (1H, m), 3.81 (1H, br s), 2.48 (1H, br s), 1.83 (1H, t, J=13.2 Hz), 1.60-1.66 (1H, m), 1.51-1.58 (1H, m), 1.41-1.46 (1H, m), 1.35-1.38 (1H, m), 1.21-1.27 (1H, m), 0.79 (9H, s), -0.12 (3H, s), -0.20 (3H, s); LCMS m/z 422.3753 ([M+H$^+$], C$_{26}$H$_{35}$NO$_2$Si requires 422.2510).

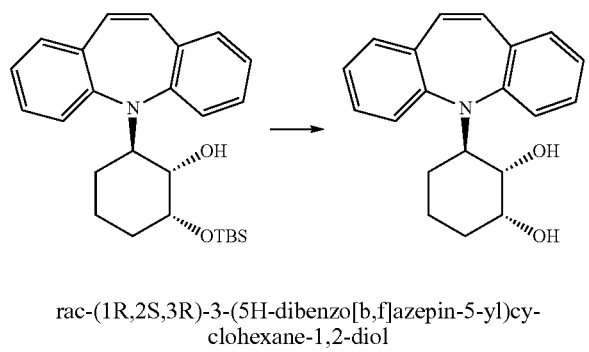

rac-(1R,2S,3R)-3-(5H-dibenzo[b,f]azepin-5-yl)cyclohexane-1,2-diol

A solution of rac-(1S,2R,6R)-2-((tert-butyldimethylsilyl)oxy)-6-(5H-dibenzo[b,f]azepin-5-yl)cyclohexanol (2.50 g, 5.93 mmol) in THF (2.0 mL) was treated with a solution of tetrabutylammonium fluoride (1.0 M in THF, 7.11 mL) and stirred for 14 h at 25° C. The solution was suspended in CH$_2$Cl$_2$ (50 mL), washed with a saturated aqueous sodium chloride (3×50 mL), dried (Na$_2$SO$_4$), and concentrated in vacuo. The residue was suspended in a minimal amount of CH$_2$Cl$_2$ and purified by flash chromatography (SiO$_2$, 0-35% ethyl acetate-hexanes) to afford the title compound as a brown solid (2.11 g, 99%). $^1$H NMR (600 MHz, CDCl$_3$) δ 7.32 (2H, tt, J=7.8, 2.4 Hz), 7.22 (2H, d, J=8.4 Hz), 7.15-7.20 (3H, m), 7.13 (1H, t, J=7.2 Hz), 6.84 (2H, q, J=11.4 Hz), 4.10 (1H, q, J=3.0 Hz), 3.70 (1H, t, J=8.4 Hz), 3.52-3.66 (1H, br m), 3.26 (1H, d, J=7.8 Hz), 2.32-2.38 (1H, br m), 1.81-1.84 (1H, m), 1.65-1.72 (2H, m), 1.52-1.56 (1H, m), 1.31-1.36 (1H, m); LCMS m/z 308.1663 ([M+H$^+$], C$_{20}$H$_{21}$NO$_2$ requires 308.1645).

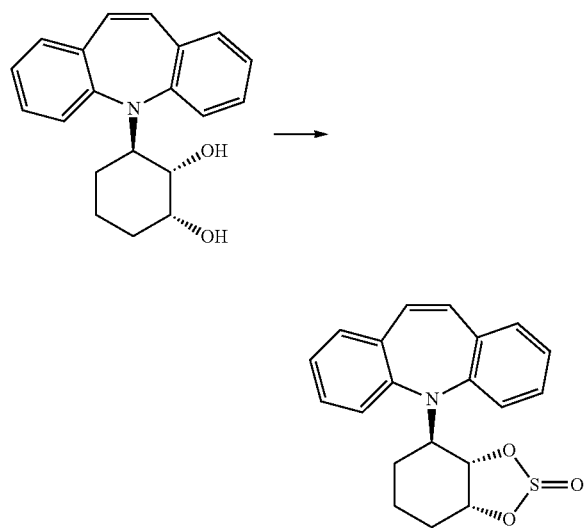

rac-(3aS,4R,7aR)-4-(5H-dibenzo[b,f]azepin-5-yl)hexahydrobenzo[d][1,3,2]dioxathiole 2-oxide A solution of rac-(1R,2S,3R)-3-(5H-dibenzo[b,f]azepin-5-yl)cyclohexane-1,2-diol (1.07 g, 3.48 mmol) in CH$_2$Cl$_2$ (10.0 mL) was cooled to 0° C., treated with triethylamine (3.86 mL, 27.9 mmol) and then treated dropwise with thionyl chloride (0.76 mL, 10.44 mmol). The mixture was warmed to 25° C., stirred for 2 h, and then poured over H$_2$O (200 mL). The aqueous layer was extracted with CH$_2$Cl$_2$ (2×100 mL) and then the combined organic layers were washed with H$_2$O (2×100 mL), dried (Na$_2$SO$_4$), and concentrated in vacuo. The residue was dissolved in a minimal amount of CH$_2$Cl$_2$ and purified by flash chromatography (SiO$_2$, 0-15% ethyl acetate-hexanes) to afford the title compound, a mixture of sulfite diastereoisomers, as a beige oil (1.08 g, 88%). $^1$H NMR (600 MHz, CDCl$_3$) δ (as a mixture of diastereomers) 7.29-7.36 (2H, m), 7.28-7.30 (2H, m), 7.21-7.25 (2H, m), 7.17-7.20 (2H, m), 2H [6.84 (d, J=2.4 Hz), 6.82 (s)], 1H [5.01 (q, J=4.2 Hz), 4.59 (q, J=4.8 Hz)], 1H [4.77 (dd, J=7.2, 4.8 Hz), 4.59 (t, J=6.6 Hz)], 1H [4.21 (ddd, J=10.2, 9.6, 3.6 Hz), 3.56 (ddd, J=9.6, 6.6, 3.6 Hz)], 1H [2.17 (dq, J=15.0, 4.2 Hz), 2.01 (dq, J=9.6, 3.6 Hz)], 2H [1.78-1.86 (m), 1.70-1.76 (m)], 1.49-1.53 (1H, m), 2H [1.34-1.38 (m), 1.22-1.28 (m)]; LCMS m/z 354.1158 ([M+H$^+$], C$_{20}$H$_{19}$NO$_3$S requires 354.1158).

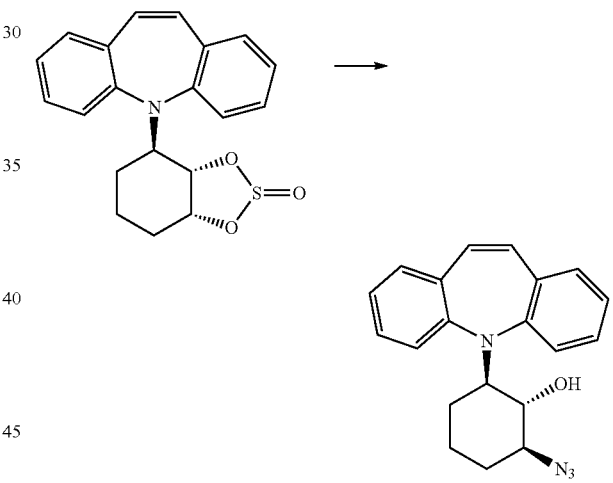

rac-(1S,2S,6R)-2-azido-6-(5H-dibenzo[b,f]azepin-5-yl)cyclohexanol. A solution of rac-(3aS,4R,7aR)-4-(5H-dibenzo[b,f]azepin-5-yl)hexahydrobenzo[d][1,3,2]dioxathiole 2-oxide (1.06 g, 2.99 mmol) in DMF (5.0 mL) was treated with KN$_3$ (0.730 g, 8.99 mmol) and heated to 100° C. for 14 h under microwave irradiation. The mixture was cooled to 25° C., poured over a solution of saturated aqueous NaCl (100 mL), and extracted with CH$_2$Cl$_2$ (3×100 mL). The combined organic layers were washed with H$_2$O (3×100 mL), saturated aqueous NaCl (100 mL), dried (Na$_2$SO$_4$), and concentrated in vacuo. The residue was suspended in a minimal amount of CH$_2$Cl$_2$ and purified by flash chromatography (SiO$_2$, 0-10% ethyl acetate-hexanes) to afford the title compound as a yellow foam (0.753 g, 76%). $^1$H NMR (600 MHz, CDCl$_3$) δ 7.32-7.35 (2H, m), 7.24 (1H, d, J=7.8 Hz), 7.18-7.20 (2H, m), 7.14-7.18 (3H, m), 6.82-6.84 (2H, s), 3.75 (1H, s), 3.29 (1H, ddd, J=12.6, 9.0, 4.8 Hz), 3.22 (1H, ddd, J=13.2, 10.2, 3.6 Hz), 3.14 (1H, t, J=9.0 Hz), 2.37 (1H, dt, J=12.6, 2.4 Hz), 1.87-1.90 (1H, m), 1.78 (1H, doublet of quintets, J=13.8, 3.6 Hz), 1.61 (1H, qd, J=12.6, 3.6 Hz), 1.30 (1H, qt, J=13.8, 3.6 Hz), 1.17 (1H, qd, J=12.6, 3.6 Hz); $^{13}$C NMR (150 MHz, CDCl$_3$) δ 148.7, 146.4, 137.6, 136.7, 132.7, 132.2, 130.2, 130.14, 130.07, 129.9, 129.5, 127.9, 126.2, 125.8, 75.4, 72.1, 65.7, 32.9, 30.0, 22.8; LCMS m/z 333.1708 ([M+H$^+$], C$_{20}$H$_{20}$N$_4$O requires 333.1710).

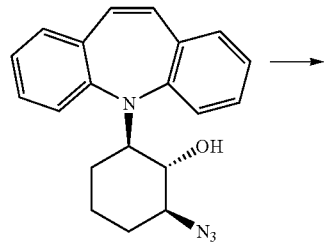

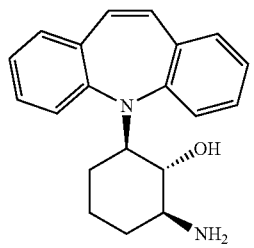

rac-(1R,2S,6R)-2-amino-6-(5H-dibenzo[b,f]azepin-5-yl)cyclohexanol

A solution of rac-(1S,2S,6R)-2-azido-6-(5H-dibenzo[b,f]azepin-5-yl)cyclohexanol (0.733 g, 2.21 mmol) in THF (10.0 mL) was cooled to 0° C., treated with PPh$_3$ (0.810 g, 3.09 mmol), H$_2$O (0.2 mL), and stirred for 14 h at 25° C. The solution was concentrated to dryness, dissolved in a minimal amount of CH$_2$Cl$_2$ and purified by flash chromatography (SiO$_2$, 0-20% ethyl acetate-hexanes to remove nonpolar impurities followed by 3% MeOH—CH$_2$Cl$_2$ to remove triphenylphosphine oxide and then 17:2:1 CH$_2$Cl$_2$:MeOH: NH$_4$OH to elute the product). The combined fractions of pure product were concentrated, dried azeotropically with toluene to afford the title compound as a yellow powder (0.609 g, 90%). $^1$H NMR (600 MHz, CDCl$_3$) δ 7.28-7.32 (2H, m), 7.24 (1H, d, J=7.2 Hz), 7.15-7.19 (2H, m), 7.11-7.15 (3H, m), 6.79 (2H, s), 3.19 (1H, ddd, J=12.0, 9.6, 3.6 Hz), 2.87 (1H, t, J=9.6 Hz), 2.60 (1H, ddd, J=12.0, 9.0, 4.2 Hz), 2.34-2.37 (1H, m), 2.05-2.50 (2H, br m), 1.74-1.78 (1H, m), 1.71 (1H, doublet of quintets, J=13.8, 3.6 Hz), 1.64 (1H, qd, J=12.6, 3.6 Hz), 1.31 (1H, qt, J=13.2, 3.6 Hz), 1.03 (1H, qd, J=13.2, 3.6 Hz); $^{13}$C NMR (150 MHz, CDCl$_3$) δ 149.2, 146.8, 137.6, 136.6, 132.8, 132.1, 130.12, 130.08, 130.0, 129.9, 129.6, 127.9, 126.0, 125.5, 77.1, 72.1, 56.0, 33.6, 32.7, 23.4; LCMS m/z 307.1807 ([M+H$^+$], C$_{20}$H$_{22}$N$_2$O requires 307.1805).

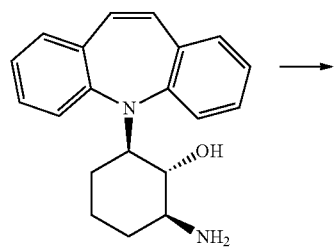

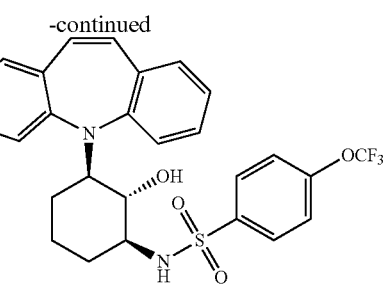

Example 25 rac-N-((1S,2S,3R)-3-(5H-dibenzo[b,f]azepin-5-yl)-2-hydroxycyclohexyl)-4-(trifluoromethoxy)benzenesulfonamide A solution of rac-(1R,2S,6R)-2-amino-6-(5H-dibenzo[b,f]azepin-5-yl)cyclohexanol (0.200 g, 0.653 mmol) in DMF (2.0 mL) was cooled to 0° C., treated with Et$_3$N (90.0 μL, 0.653 mmol), and 4-trifluoromethoxybenzenesulfonyl chloride (110.0 μL, 0.653 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-35% ethyl acetate-hexanes) to afford the title compound Example 25 as a yellow foam (0.322 g, 93%). $^1$H NMR (600 MHz, CDCl$_3$) δ 7.88 (2H, d, J=9.0 Hz), 7.18-7.25 (4H, m), 7.07-7.11 (4H, m), 7.04-7.07 (2H, m), 6.75 (2H, s), 5.09 (1H, br s), 3.32 (1H, br s), 3.14-3.20 (1H, br m), 2.95 (1H, t, J=8.4 Hz), 2.84-2.88 (1H, m), 2.21-2.23 (1H, m), 1.97-2.00 (1H, m), 1.56-1.60 (2H, m), 1.11 (2H, q, J=12.0 Hz); $^{13}$C NMR (150 MHz, CDCl$_3$) δ 152.1, 149.2, 145.7, 139.0, 137.3, 136.1, 132.8, 132.1, 130.2, 130.1, 130.0, 129.8, 129.5, 128.9, 126.8, 126.1, 125.6, 120.9, 119.6, 73.0, 58.3, 31.8, 30.9, 29.3, 22.9; LCMS m/z 531.1549 ([M+H$^+$], C$_{27}$H$_{25}$F$_3$N$_2$O$_4$S requires 531.1560).

Example 26, from Chiral Material

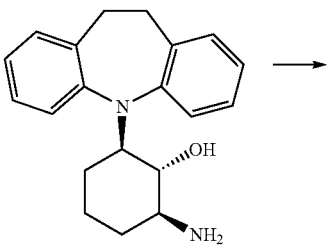

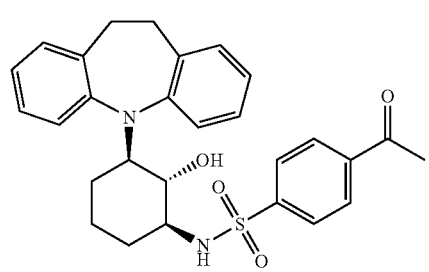

Example 26

4-Acetyl-N-((1S,2S,3R)-3-(10,11-dihydro-5H-dibenzo[b,f]azepin-5-yl)-2-hydroxycyclohexyl)benzenesulfonamide A solution of (1R,2S,6R)-2-amino-6-(10,11-dihydro-5H-dibenzo[b,f]azepin-5-yl)cyclohexanol (0.200 g, 0.648 mmol) in DMF (1.0 mL) was cooled to 0° C., treated with Et$_3$N (89.0 µL, 0.648 mmol), and 4-acetylbenzenesulfonyl chloride (0.142 g, 0.648 mmol). The mixture was warmed to 25° C., and stirred for 2 h. The mixture was partitioned between saturated aqueous NaCl (100 mL), and CH$_2$Cl$_2$ (300 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-25% ethyl acetate-hexanes) to afford the title compound Example 26 as a yellow foam (0.241 g, 76%). $^1$H NMR (600 MHz, CDCl$_3$) δ 8.06 (2H, d, J=8.4 Hz), 8.00 (2H, d, J=8.4 Hz), 7.15-7.45 (2H, br m), 7.10 (2H, d, J=6.6 Hz), 6.85-7.15 (4H, m), 5.41 (1H, d, J=6.0 Hz), 3.64 (1H, td, J=10.8, 3.0 Hz), 3.38 (1H, t, J=9.6 Hz), 3.20-3.55 (2H, br m), 3.16 (1H, heptet, J=5.4 Hz), 3.12 (1H, br s), 2.68-2.90 (2H, br m), 2.65 (3H, s), 2.10-2.14 (1H, m), 1.79-1.83 (1H, m), 1.55-1.59 (1H, m), 1.15-1.23 (2H, m), 1.07-1.13 (1H, m); LCMS m/z 491.1992 ([M+H$^+$], C$_{28}$H$_{30}$N$_2$O$_4$S requires 491.1999).

Example 27

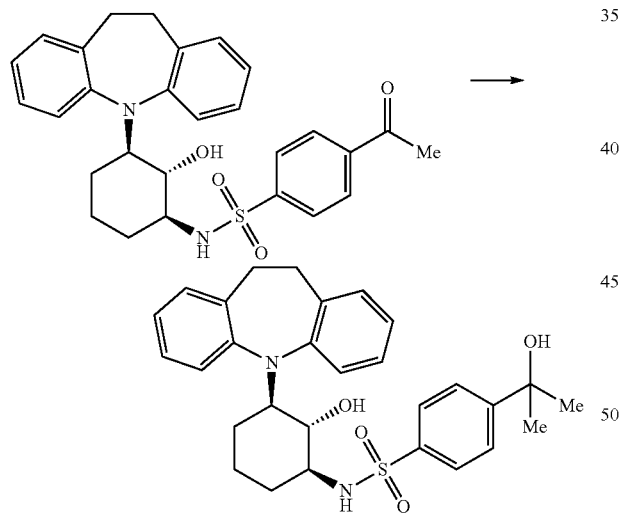

Example 27

N-((1S,2S,3R)-3-(10,11-dihydro-5H-dibenzo[b,f]azepin-5-yl)-2-hydroxycyclohexyl)-4-(2-hydroxypropan-2-yl)benzenesulfonamide A solution of 4-acetyl-N-((1S,2S,3R)-3-(10,11-dihydro-5H-dibenzo[b,f]azepin-5-yl)-2-hydroxycyclohexyl)benzenesulfonamide (0.0600 g, 0.122 mmol) in THF (3.0 mL) was cooled to cooled to 0° C. and treated with MeMgBr (3M in Et$_2$O, 41.0 µL, 1.22 mmol).

The mixture was stirred at 0° C. for 30 minutes, then warmed to 25° C. and stirred for 2 h. The mixture was poured over saturated aqueous NH$_4$Cl (100 mL), and extracted with CH$_2$Cl$_2$ (3×100 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-50% ethyl acetate-hexanes) to afford the title compound Example 27 as a white powder (0.0442 g, 72%). $^1$H NMR (600 MHz, CDCl$_3$) δ 7.85 (2H, d, J=8.4 Hz), 7.64 (2H, d, J=8.4 Hz), 7.15-7.45 (2H, br m), 7.12 (2H, d, J=7.2 Hz), 6.85-7.15 (4H, m), 5.13 (1H, d, J=5.4 Hz), 3.63 (1H, td, J=10.8, 3.0 Hz), 3.38 (1H, t, J=9.6 Hz), 3.20-3.55 (2H, br m), 3.12-3.16 (1H, m), 3.12 (1H, br s), 2.60-2.95 (2H, br m), 2.10-2.14 (1H, m), 1.79-1.84 (1H, m), 1.61 (6H, s), 1.55-1.57 (1H, m), 1.13-1.23 (2H, m), 1.05-1.11 (1H, m); LCMS m/z 507.2305 ([M+H$^+$], C$_{29}$H$_{34}$N$_2$O$_4$S requires 507.2312).

Example 28

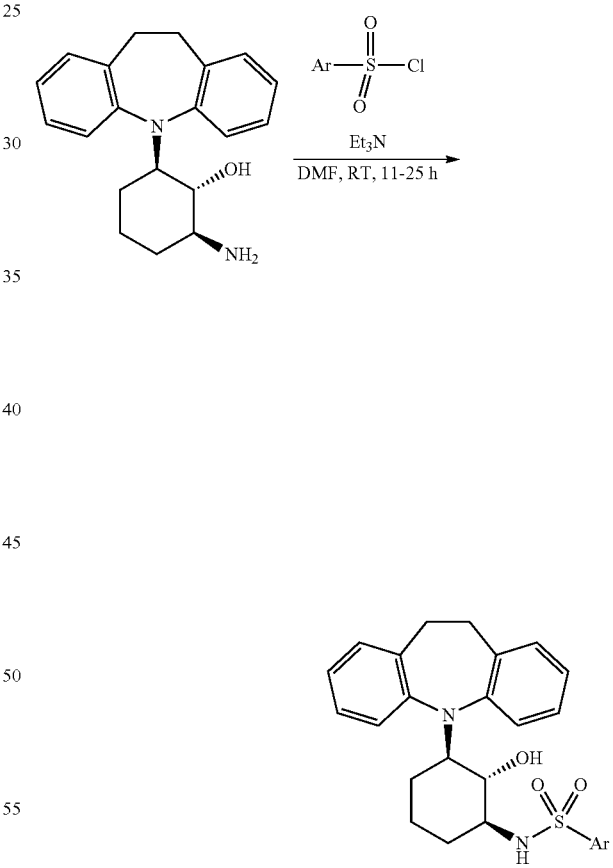

General Procedure for Synthesis:

A solution of 2-amino-6-(tricyclic)cyclohexanol (1 Eq) in DMF was cooled to 0° C., treated with Et$_3$N (4 Eq), and substituted phenyl (or) pyrazolyl sulfonyl chloride (1.1 Eq). The mixture was warmed to RT, and stirred for 11-25 h. The mixture was partitioned between water (10 mL) and CH$_2$Cl$_2$ (10 mL). The organic layer was washed with saturated aqueous NaCl (30 mL×5) to remove DMF, and concentrated in vacuo. The residue was dissolved in a minimal amount of CH$_2$Cl$_2$ and purified by flash chromatography (SiO$_2$) afforded N-(2-hydroxy-3-(tricyclic)cyclohexyl)-substituted arylsulfonamide.

Example 28

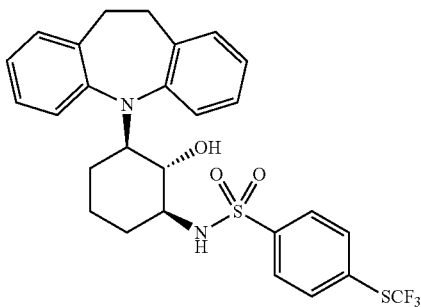

N-(3-(10,11-dihydro-5H-dibenzo[b,f]azepin-5-yl)-2-hydroxycyclohexyl)-4-((trifluoromethyl)thio)benzenesulfonamide Using the general procedure, 2-amino-6-(10,11-dihydro-5H-dibenzo[b,f]azepin-5-yl)cyclohexanol (0.070 g, 0.227 mmol) in DMF (1.0 mL) was reacted with Et$_3$N (0.126 mL, 0.908 mmol), and 4-((trifluoromethyl)thio)benzene-1-sulfonyl chloride (0.053 mL, 0.249 mmol) for 11 h. Flash chromatography (SiO$_2$, 10%-25% ethylacetate-hexanes), afforded N-(3-(10,11-dihydro-5H-dibenzo[b,f]azepin-5-yl)-2-hydroxycyclohexyl)-4-((trifluoromethyl)thio)benzenesulfonamide (Example 28, 0.052 g, 42%). $^1$H NMR (600 MHz, CDCl$_3$) δ 7.94 (2H, d, J=7.2 Hz), 7.80 (2H, d, J=7.8 Hz), 7.37-7.35 (1H, bs), 7.13-7.04 (6H, m), 6.93 (1H, bs), 5.12 (1H, bs), 3.64 (1H, bs), 3.44 (2H, bs), 3.29 (1H, bs), 3.14 (1H, bs), 2.83-2.75 (2H, m), 2.08 (1H, bs), 1.89-1.87 (1H, m), 1.65-1.59 (5H, m); ESI-HRMS m/z 549.1482 ([M+H$^+$], C$_{27}$H$_{28}$F$_3$N$_2$O$_3$S$_2$ requires 549.1488).

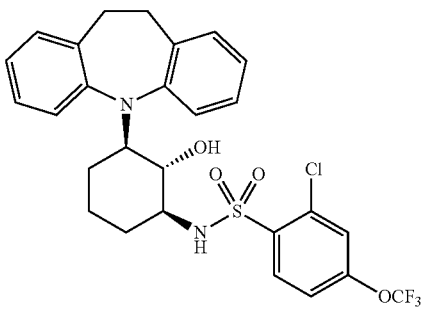 [SMILES: O=S(=O)(N[C@H]1CCC[C@@H](N2c3ccccc3CCc3ccccc32)[C@@H]1O)c1ccc(OC(F)(F)F)cc1Cl]

Example 29

2-chloro-N-(3-(10,11-dihydro-5H-dibenzo[b,f]azepin-5-yl)-2-hydroxycyclohexyl)-4-(trifluoromethoxy)benzenesulfonamide Using the general procedure, 2-amino-6-(10,11-dihydro-5H-dibenzo[b,f]azepin-5-yl)cyclohexanol (0.070 g, 0.027 mmol) in DMF (1.0 mL) was reacted with Et$_3$N (0.126 mL, 0.908 mmol), and 2-chloro-4-(trifluoromethoxy)benzene-1-sulfonyl chloride (0.053 mL, 0.249 mmol) for 11 h. Flash chromatography (SiO$_2$, 10%-25% ethylacetate-hexanes) afforded 2-chloro-N-(3-(10,11-dihydro-5H-dibenzo[b,f]azepin-5-yl)-2-hydroxycyclohexyl)-4-(trifluoromethoxy)benzenesulfonamide (Example 29, 0.088 g, 69%). $^1$H NMR (600 MHz, CDCl$_3$) δ 8.18 (1H, d, J=9.0 Hz), 7.41 (2H, bs), 7.29-7.28 (1H, m), 7.20-7.12 (5H, m), 7.03 (1H, bs), 6.91 (1H, bs), 5.39 (1H, bs), 3.61 (1H, bs), 3.43-3.42 (1H, m), 3.33-3.27 (1H, m), 3.07-3.06 (1H, m), 2.82-2.73 (2H m), 2.08 (1H, bs), 1.81 (1H, bs), 1.64 (3H, bs), 1.15 (3H, bs); ESI-HRMS m/z 567.1328 ([M+H$^+$], C$_{27}$H$_{27}$ClF$_3$N$_2$O$_4$S requires 567.1327).

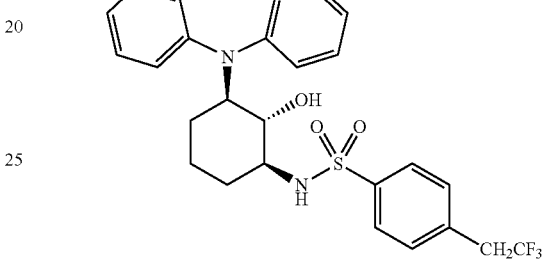

Example 30

N-(3-(10,11-dihydro-5H-dibenzo[b,f]azepin-5-yl)-2-hydroxycyclohexyl)-4-(2,2,2-trifluoroethyl)benzenesulfonamide: Using the general procedure, 2-amino-6-(10,11-dihydro-5H-dibenzo[b,f]azepin-5-yl)cyclohexanol (0.070 g, 0.227 mmol) in DMF (1.0 mL) was reacted with Et$_3$N (0.126 mL, 0.908 mmol), and 4-(2,2,2-trifluoroethyl)benzene-1-sulfonyl chloride (0.064 g, 0.249 mmol) for 15 h. Flash chromatography (SiO$_2$, 10%-25% ethylacetate-hexanes) afforded N-(3-(10,11-dihydro-5H-dibenzo[b,f]azepin-5-yl)-2-hydroxycyclohexyl)-4-(2,2,2-trifluoroethyl)benzenesulfonamide (Example 30, 0.069 g, 58%). $^1$H NMR (600 MHz, MeOD) δ 7.81 (2H, d, J=7.8 Hz), 7.49 (2H, d, J=7.8 Hz), 7.38 (2H, bs), 7.06-7.04 (4H, m), 6.92 (2H, bs), 3.64-3.55 (3H, m), 3.38-3.30 (3H, m), 3.11-3.07 (1H, m), 2.70 (2H, bs), 2.07-2.05 (1H, m), 1.51-1.45 (2H, m), 1.27-1.21 (1H, m), 1.14-1.00 (2H, m); LCMS m/z 531.2170 ([M+H$^+$], C$_{28}$H$_{30}$F$_3$N$_2$O$_3$S requires 531.1924).

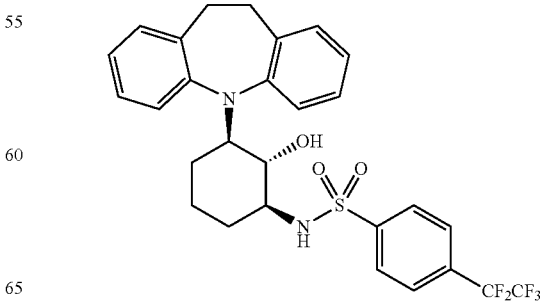

Example 31

N-(3-(10,11-dihydro-5H-dibenzo[b,f]azepin-5-yl)-2-hydroxycyclohexyl)-4-(perfluoroethyl)benzenesulfonamide Using the general procedure, 2-amino-6-(10,11-dihydro-5H-dibenzo[b,f]azepin-5-yl)cyclohexanol (0.070 g, 0.227 mmol) in DMF (1.0 mL) was reacted with Et$_3$N (0.126 mL, 0.908 mmol), and 4-(perfluoroethyl)benzene-1-sulfonyl chloride (0.073 g, 0.249 mmol) for 15 h. The mixture was warmed to RT, and stirred for 15 h. Flash chromatography (SiO$_2$, 10-25% ethylacetate-hexanes) afforded N-(3-(10,11-dihydro-5H-dibenzo[b,f]azepin-5-yl)-2-hydroxycyclohexyl)-4-(perfluoroethyl)benzenesulfonamide (Example 31, 0.081 g, 63%). $^1$H NMR (600 MHz, CDCl$_3$) δ 8.04 (2H, d, J=8.4 Hz), 7.76 (2H, d, J=8.4 Hz), 7.11-7.10 (8H, m), 5.19 (1H, bs), 3.64-3.62 (1H, m), 3.39-3.36 (2H, m), 3.20-3.16 (2H, m), 2.94-2.81 (3H, m), 2.14-2.12 (1H, m), 1.93-1.90 (1H, m), 1.61-1.59 (1H, m), 1.25-1.10 (3H, m); LCMS m/z 567.1947 ([M+H$^+$], C$_{28}$H$_{28}$F$_5$N$_2$O$_3$S requires 567.1736).

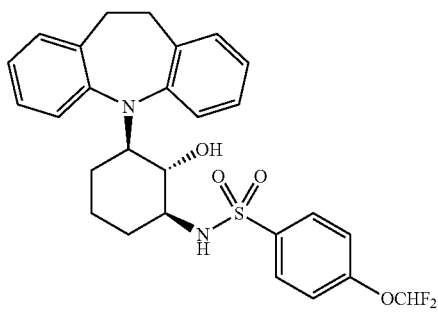 [SMILES: O=S(=O)(N[C@H]1CCC[C@@H](N2c3ccccc3CCc3ccccc32)[C@@H]1O)c1ccc(OC(F)F)cc1]

Example 32

4-(difluoromethoxy)-N-(3-(10,11-dihydro-5H-dibenzo[b,f]azepin-5-yl)-2-hydroxycyclohexyl)benzenesulfonamide Using the general procedure, 2-amino-6-(10,11-dihydro-5H-dibenzo[b,f]azepin-5-yl)cyclohexanol (0.070 g, 0.227 mmol) in DMF (1.0 mL) was reacted with Et$_3$N (0.126 mL, 0.908 mmol), and 4-(difluoromethoxy)benzene-1-sulfonyl chloride (0.039 mL, 0.249 mmol) for 25 h. Flash chromatography (SiO$_2$, 10%-25% ethylacetate-hexanes) afforded 4-(difluoromethoxy)-N-(3-(10,11-dihydro-5H-dibenzo[b,f]azepin-5-yl)-2-hydroxycyclohexyl)benzenesulfonamide (Example 32, 0.073 g, 63%). $^1$H NMR (600 MHz, MeOD) δ 7.85 (2H, d, J=8.4 Hz), 7.37 (2H, bs), 7.25 (2H, d, J=8.4 Hz), 7.09-7.05 (4H, m), 6.92 (2H, bs), 3.66-3.63 (1H, m), 3.42 (1H, bs), 3.34-3.29 (3H, m), 3.09-3.05 (1H, m), 2.72 (2H, bs), 2.09-2.07 (1H, m), 1.56-1.54 (1H, m), 1.51-1.48 (1H, m), 1.29-1.24 (1H, m), 1.17-1.02 (2H, m); LCMS m/z 515.1846 ([M+H$^+$], C$_{27}$H$_{29}$F$_2$N$_2$O$_4$S requires 515.1811).

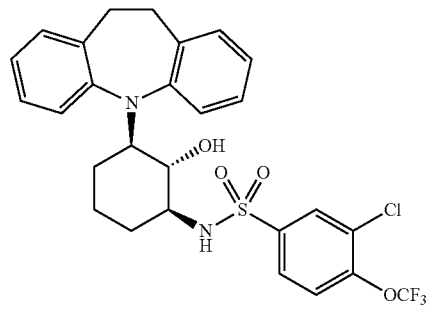 [SMILES: O=S(=O)(N[C@H]1CCC[C@@H](N2c3ccccc3CCc3ccccc32)[C@@H]1O)c1ccc(OC(F)(F)F)c(Cl)c1]

Example 33

3-chloro-N-(3-(10,11-dihydro-5H-dibenzo[b,f]azepin-5-yl)-2-hydroxycyclohexyl)-4-(trifluoromethoxy)benzenesulfonamide Using the general procedure, 2-amino-6-(10,11-dihydro-5H-dibenzo[b,f]azepin-5-yl)cyclohexanol (0.047 g, 0.154 mmol) in DMF (1.0 mL) was reacted with Et$_3$N (0.085 mL, 0.616 mmol), and 3-chloro-4-(trifluoromethoxy)benzene-1-sulfonyl chloride (0.031 mL, 0.169 mmol) for 25 h. Flash chromatography (SiO$_2$, 10%-25% ethylacetate-hexanes) afforded 3-chloro-N-(3-(10,11-dihydro-5H-dibenzo[b,f]azepin-5-yl)-2-hydroxycyclohexyl)-4-(trifluoromethoxy)benzenesulfonamide (Example 33, 0.057 g, 66%). $^1$H NMR (600 MHz, MeOD) δ 8.07 (1H, d, J=1.8 Hz), 7.86 (1H, d, J=8.4 Hz), 7.57 (1H, d, J=8.4 Hz), 7.35 (2H, bs), 7.06-7.01 (4H, m), 6.90 (2H, bs), 3.63-3.60 (1H, m), 3.30-3.26 (3H, m), 3.15-3.11 (1H, m), 2.71 (2H, bs), 2.08 (1H, d, J=12.0 Hz), 1.66 (1H, d, J=10.8 Hz), 1.52-1.50 (1H, m), 1.27-1.06 (3H, m); LCMS m/z 567.1371 ([M+H$^+$], C$_{27}$H$_{27}$ClF$_3$N$_2$O$_4$S requires 567.1327).

H1650 Cell Viability Assays (GI$_{50}$ Determination)

Cell viability assays were performed according to Denizot, F. and R. Lang, Rapid colorimetric assay for cell growth and survival: Modifications to the tetrazolium dye procedure giving improved sensitivity and reliability Journal of Immunological Methods, 1986. 89(22): p. 271-277.

Cells were plated at 150,000 cells per well in a 12 well plate. Twenty-four hours after plating, cells were treated as described with increasing concentrations of drug and control. Forty-eight hours after drug treatment, cells were treated with 100 uL of 3-(4,5-Dimethylthiazol-2-yl)-2,5-diphenyltetrazolium bromide (MTT) and incubated for 2 hours at 37 C. The MTT solution was subsequently replaced with 300 uL of n-propyl alcohol and re-aliquoted to a 96 well plates. Spectrophotometric analysis of each solution was performed using a 96 well plate reader at 600 nm in triplicate. The results are shown below in Table I:

TABLE I

| Example No. | Structure | H1650 GI50 |
|---|---|---|
| Example 1 | 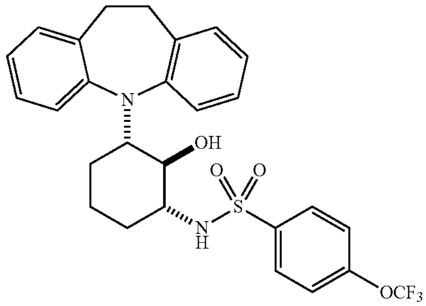 | 5 uM |
| Example 2 | 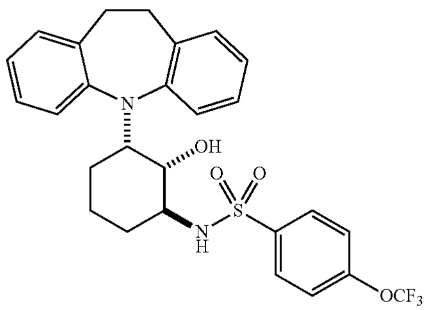 | 15 uM |
| Example 3a | 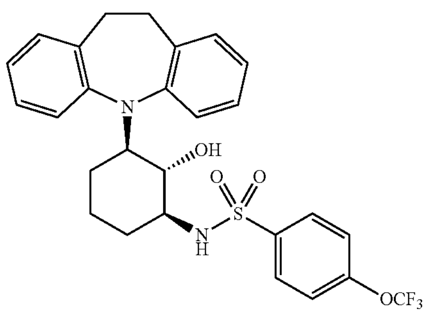 [SMILES: O=S(=O)(N[C@H]1CCC[C@@H](N2c3ccccc3CCc3ccccc32)[C@@H]1O)c1ccc(OC(F)(F)F)cc1] | 5 uM |
| Example 3b | 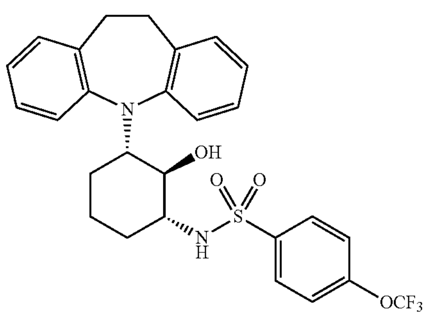 [SMILES: O=S(=O)(N[C@@H]1CCC[C@H](N2c3ccccc3CCc3ccccc32)[C@H]1O)c1ccc(OC(F)(F)F)cc1] | 5 uM |
| Example 4 | 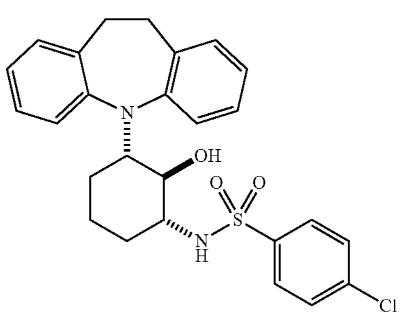 | 10 uM |

TABLE I-continued

| Example No. | Structure | H1650 GI50 |
|---|---|---|
| Example 5 | 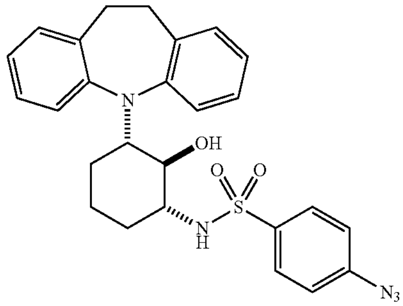 | 15 uM |
| Example 17 | 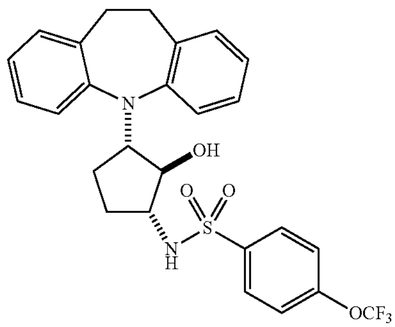 | 15 uM |
| Example 18 | 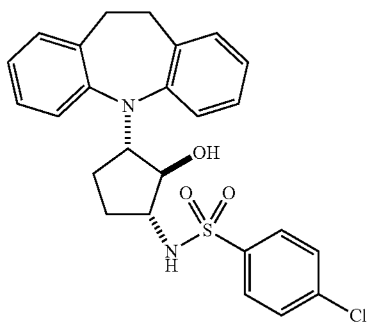 | 20 uM |
| Example 20 | 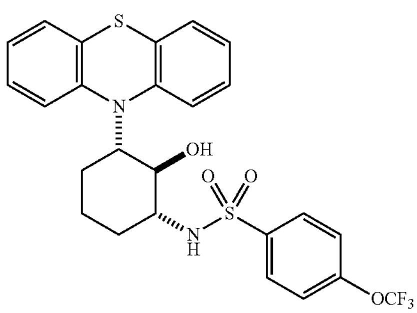 | 5 uM |
| Example 21 | 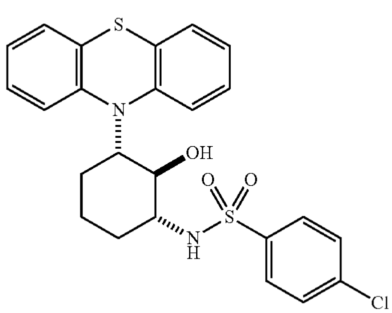 | 10 uM |

TABLE I-continued

| Example No. | Structure | H1650 GI50 |
|---|---|---|
| Example 7 | 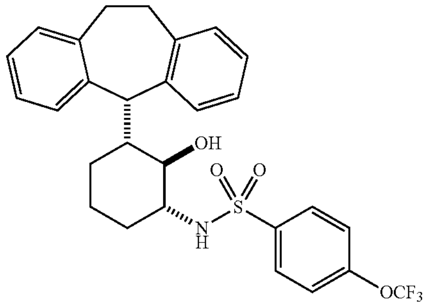 | |
| Example 19 | 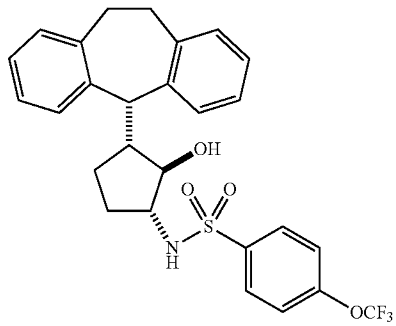 | |
| Example 22 | 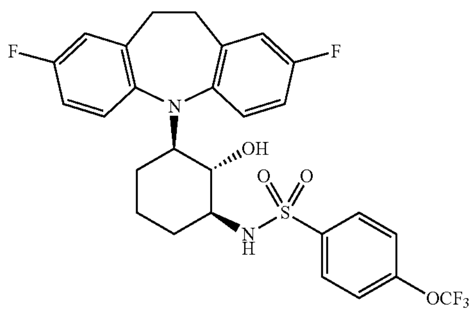 [SMILES: O=S(=O)(N[C@H]1CCC[C@@H](N2c3ccc(F)cc3CCc3cc(F)ccc32)[C@@H]1O)c1ccc(OC(F)(F)F)cc1] | 7 uM |
| Example 23 | 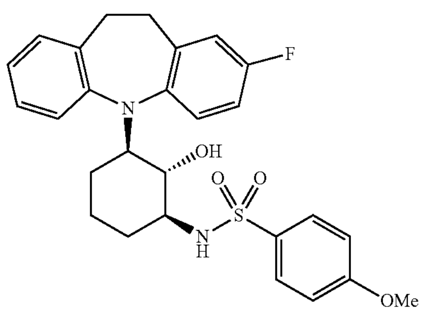 [SMILES: COc1ccc(S(=O)(=O)N[C@H]2CCC[C@@H](N3c4ccccc4CCc4cc(F)ccc43)[C@@H]2O)cc1] | 20 uM |
| Example 24 | 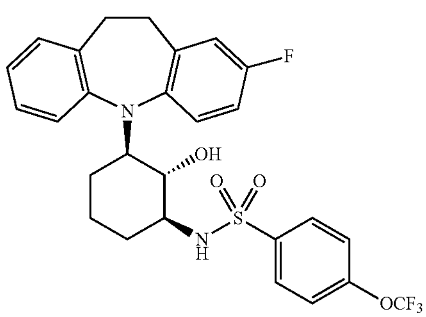 | 5 uM |

TABLE I-continued

| Example No. | Structure | H1650 GI50 |
|---|---|---|
| Example 25 | (dibenzazepine-cyclohexyl-OH-NHSO2-C6H4-OCF3) | 10 uM |
| Example 26 | (dihydrodibenzazepine-cyclohexyl-OH-NHSO2-C6H4-C(O)Me) | 20 uM |
| Example 27 | (dihydrodibenzazepine-cyclohexyl-OH-NHSO2-C6H4-C(Me)2OH) | 15 uM |
| Example 28 | (dibenzazepine-cyclohexyl-OH-NHSO2-C6H4-SCF3) | 5 uM |

TABLE I-continued
| Example No. | Structure | H1650 GI50 |
| --- | --- | --- |
| Example 29 | 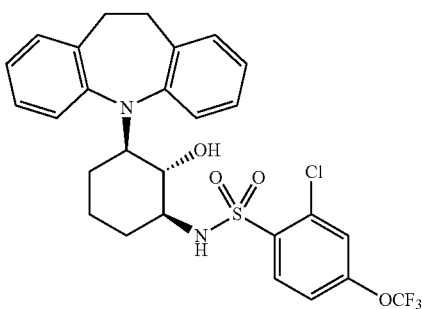 | 5 uM |
| Example 30 | 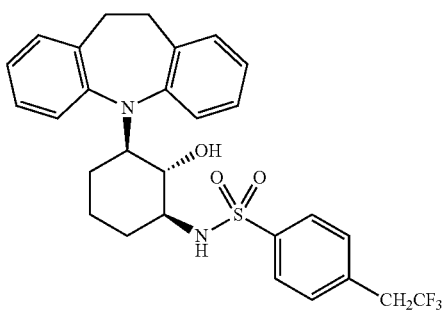 | 5 uM |
| Example 31 | 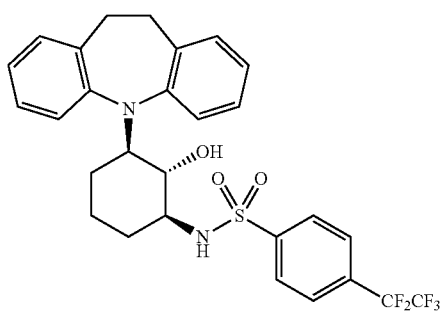 | 5 uM |
| Example 32 | 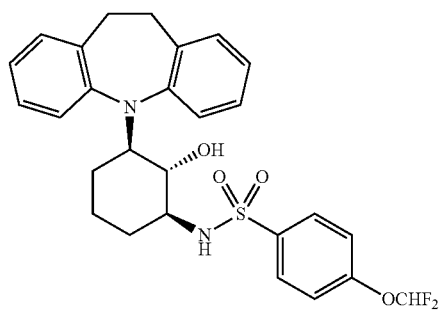 [SMILES: O=S(=O)(N[C@H]1CCC[C@@H](N2c3ccccc3CCc3ccccc32)[C@@H]1O)c1ccc(OC(F)F)cc1] | 10 uM |

TABLE I-continued

| Example No. | Structure | H1650 GI50 |
|---|---|---|
| Example 33 | (structure) | 5 uM |

Mouse Tumor Assay

To assess the in vivo effects of the compounds, subcutaneous xenograft of prostate cancer cell line LNCaP was generated. Cells ($5\times10^6$, 0.1 mL in 1:1 Matrigel:Media) were injected into the right flank of 8-week-old male SCID nude castrated mice (NCI). Tumor volume was assessed three times a week by caliper measurement. Mice were randomized to treatment groups based on initial tumor volume average of 247 mm$^3$ per group. Mice were dosed by oral gauvage with 100 mg/kg of Example 3a twice daily (BID) as a suspension in 0.1% Tween80/0.5% sodium carboxymethylcellulose (CMC) in water. Mouse tumors were measured three times a week for 31 days and animals treated with Example 3a showed tumors 35% versus control at the end of the experiment. Mouse body weights were recorded weekly and percentage of mice body weights during treatment was calculated as: weight at each time point/initial weight×100. Animals were observed for signs of toxicity (mucous diarrhea, abdominal stiffness and weight loss) and no adverse signs were observed. Mice underwent treatment for 31 days and were sacrificed 2 hours after the last dose. Tumors were then excised and cut for both formalin-fixation and snap frozen in liquid nitrogen. Compounds showed statistically significant inhibition of tumor (T) growth versus vehicle control(C) as shown in the Table below. No statistically significant toxicity was observed as judged from animal body weights of compound treated groups versus vehicle control group.

| Compound; dose; frequency | Mean Tumor Volume(T) | % T/C |
|---|---|---|
| Vehicle 0.1% Tween: 0.5% CMC in water | 1402 | 100.00 |
| Example 3a; 100 mg/kg; BID | 485 | 34.6 |

MTS Cell Proliferation Assay $GI_{50}$ for Example 3a and 3b for Molt4 cells was measured using the CellTiter96 AQueous Non-Radioactive Cell Proliferation Assay (Promega). Briefly, two technical replicates of $1\times10^5$ cells suspended in 50 μL RPMI-1640 media were pipetted per well into a 96-well plate for each condition. An equal volume of Example 3a or 3b was dissolved in media or vehicle control (DMSO) was added to each well for final concentration of 0, 5, 10, 15, 20, 30, 40, or 80 μM of 3a or 3b. Cells were allowed to grow for 48 hours at 37° C. with 5% $CO_2$, after which 20 μL of MTS/PMS solution was added to each well and cells were incubated for an additional 4 hrs. At the end of the incubation period, A490 was read on a Biotek uQuant spectrophotometer to measure formazen production. Relative viability was calculated as A490 for each drug condition relative to vehicle alone. Average of 3 biological replicates showed $GI_{50}$ of 6 μM for Example 3a and a $GI_{50}$ of 8 μM for Example 3b.

In summary, the invention relates to:

[1]. A compound of formula I, II, IIIa or IIIb.

[2]. A compound according to [1] above wherein B is —($CH_2$—$CH_2$)—.

[3]. A compound according to [1] above wherein B is —S—.

[4]. A compound according to [1] above wherein B is —CH═CH—.

[5]. A compound according to any of [1] to [4] above wherein A is N.

[6]. A compound according to any of [1] to [4] above wherein A is —CH.

[7]. A compound according to any of [1] to [6] above wherein n is 1.

[8]. A compound according to any of [1] to [6] above wherein n is 0.

[9]. A compound according to any of [1] to [6] above wherein n is 2.

[10]. A compound according to any of [1] to [9] above wherein $X^1$ and $X^2$ are both —H.

[11]. A compound according to any of [1] to [10] above wherein Y represents one substituent selected from —H, —F, —Cl, —($C_1$-$C_3$)haloalkyl, —($C_1$-$C_3$)haloalkoxy, —($C_1$-$C_3$)alkoxy, —C(═O)($C_1$-$C_3$)alkyl, —C(═O)H, —($C_1$-$C_3$)hydroxyalkyl, —($C_1$-$C_3$)haloalkylthio, —$N_3$, and —CN.

[12]. A compound according to any of [1] to [10] above wherein Y represents one substituent selected from —H, —F, —Cl, —$CF_3$, —$CH_2CF_3$, —$CF_2CF_3$, —$OCF_3$, —$OCHF_2$, —$OCH_3$, —C(═O)$CH_3$, —C(═O)H, —C($CH_3$)$_2$OH, —$SCF_3$, —$N_3$, and —CN.

[13]. A compound according to any of [1] to [10] above wherein one instance of Y is H or Cl, and another instance of Y is selected from —H, —F, —Cl, —($C_1$-$C_3$)haloalkyl, —($C_1$-$C_3$)haloalkoxy, —($C_1$-$C_3$)alkoxy, —C(═O)($C_1$-$C_3$)alkyl, —C(═O)H, —($C_1$-$C_3$)hydroxyalkyl, —($C_1$-$C_3$)haloalkylthio, —$N_3$, and —CN.

[14]. A compound according to any of [1] to [10] above wherein one instance of Y is H or Cl, and another instance of Y is —OCF$_3$.

[15]. A compound according to any of [1] to [10] above wherein Y is —OCF$_3$.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

We claim:

1. A compound of formula (I):

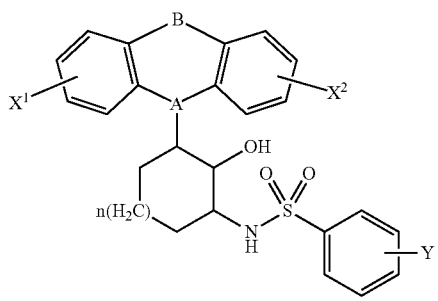

I wherein:
B is selected from the group consisting of: —S—, —(CH$_2$—CH$_2$)—, and —CH=CH—;
A is selected from N and CH;
n is zero, 1 or 2;
X$^1$ is selected from —H, —F, —Cl, —CF$_3$, and —CN;
X$^2$ is selected from —H, —F, —Cl, —CF$_3$, and —CN; and
Y represents one or two substituents each independently selected from —H, —F, —Cl, —(C$_1$-C$_3$)haloalkyl, —(C$_1$-C$_3$)haloalkoxy, —(C$_1$-C$_3$)alkoxy, —C(=O)(C$_1$-C$_3$)alkyl, —C(=O)H, —(C$_1$-C$_3$)hydroxyalkyl, —(C$_1$-C$_3$)haloalkylthio, —N$_3$, and —CN.

2. A compound according to claim 1 of formula (II):

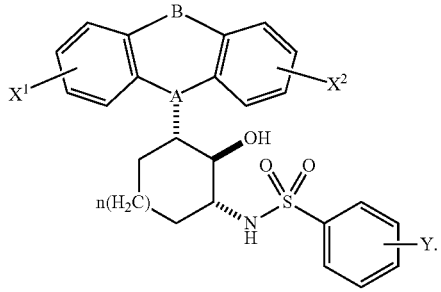

II

3. A compound according to claim 1, wherein B is —(CH$_2$—CH$_2$)—.

4. A compound according to claim 1, wherein B is —S—.

5. A compound according to claim 1, wherein B is —CH=CH—.

6. A compound according to claim 1, wherein A is N.

7. A compound according to claim 6, wherein B is —(CH$_2$—CH$_2$)— and A is N.

8. A compound according to claim 1, wherein A is —CH.

9. A compound according to claim 1, wherein n is 1.

10. A compound according to claim 1, wherein X$^1$ and X$^2$ are both H.

11. A compound according to claim 1, wherein one instance of Y is H or Cl, and another instance of Y is selected from —H, —F, —(C$_1$-C$_3$)haloalkyl, —(C$_1$-C$_3$)haloalkoxy, —(C$_1$-C$_3$)alkoxy, —C(=O)(C$_1$-C$_3$)alkyl, —C(=O)H, —(C$_1$-C$_3$)hydroxyalkyl, —(C$_1$-C$_3$)haloalkylthio, —N$_3$, and —CN.

12. A compound according to claim 11, wherein one instance of Y is H or Cl, and another instance of Y is —OCF$_3$.

13. A compound according to claim 9, wherein B is —(CH$_2$—CH$_2$)— and n is 1.

14. A compound according to claim 1 of formula:

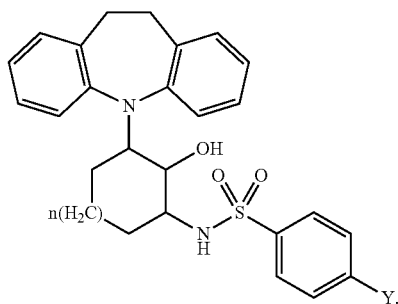

15. A compound according to claim 14 of formula:

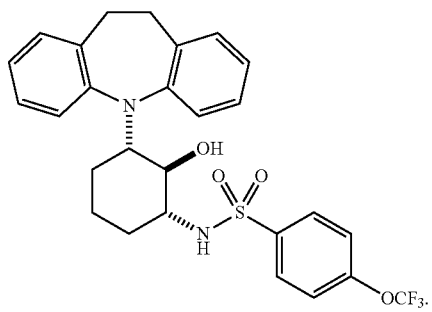

16. A method for treating a disease in a patient chosen from:
breast cancer, prostate cancer, leukemia, lung cancer, and glioblastoma
the method comprising administering to the patient a therapeutically effective amount of a compound according to claim 1.

17. A pharmaceutical composition comprising a pharmaceutically acceptable carrier and a compound according to claim 1.

18. A compound according to claim 1 selected from the following:

| Example No. | Structure |
|---|---|
| Example 1 | 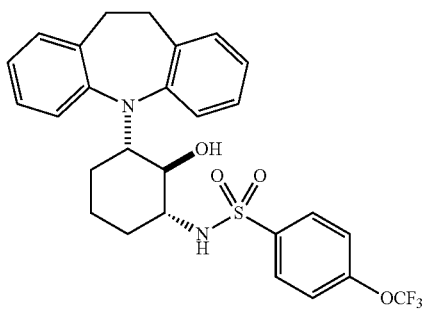 [SMILES: O=S(=O)(N[C@@H]1CCC[C@H](N2c3ccccc3CCc3ccccc32)[C@H]1O)c1ccc(OC(F)(F)F)cc1] |
| Example 2 | 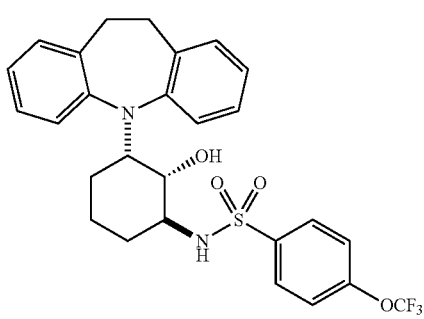 |
| Example 3a | 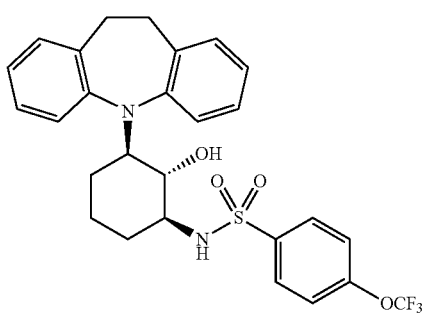 [SMILES: O=S(=O)(N[C@H]1CCC[C@@H](N2c3ccccc3CCc3ccccc32)[C@@H]1O)c1ccc(OC(F)(F)F)cc1] |
| Example 3b | 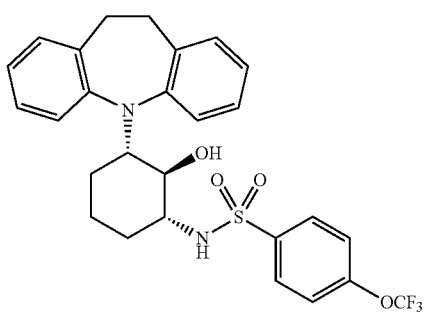 [SMILES: O=S(=O)(N[C@@H]1CCC[C@H](N2c3ccccc3CCc3ccccc32)[C@H]1O)c1ccc(OC(F)(F)F)cc1] |
| Example 4 | 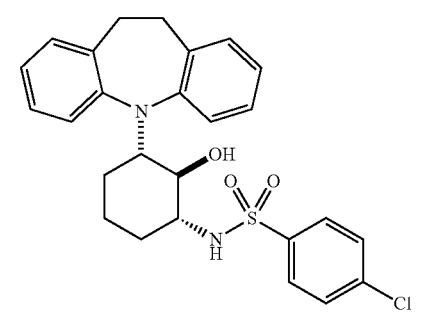 [SMILES: O=S(=O)(N[C@@H]1CCC[C@H](N2c3ccccc3CCc3ccccc32)[C@H]1O)c1ccc(Cl)cc1] |
-continued
| Example No. | Structure |
|---|---|
| Example 5 | 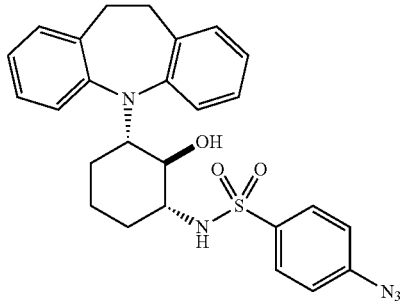 [SMILES: [N-]=[N+]=Nc1ccc(S(=O)(=O)N[C@@H]2CCC[C@H](N3c4ccccc4CCc4ccccc43)[C@H]2O)cc1] |
| Example 17 | 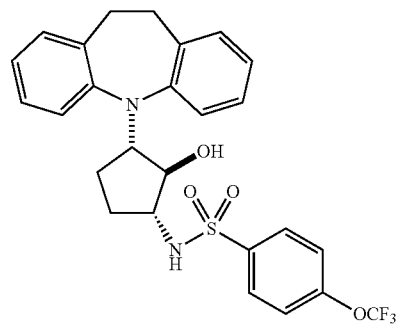 |
| Example 18 | 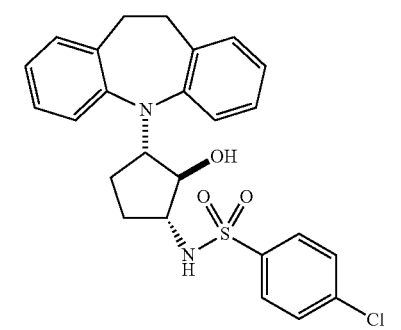 [SMILES: O=S(=O)(N[C@@H]1CC[C@H](N2c3ccccc3CCc3ccccc32)[C@H]1O)c1ccc(Cl)cc1] |
| Example 20 | 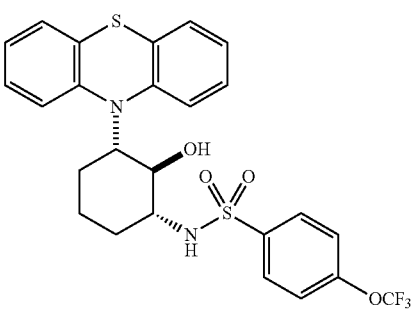 |
| Example 21 | 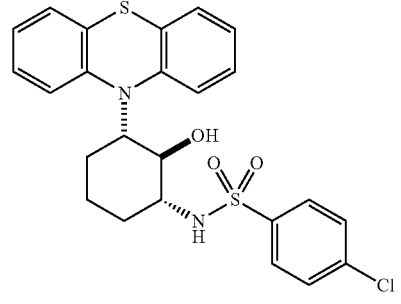 |

| Example No. | Structure |
|---|---|
| Example 7 | 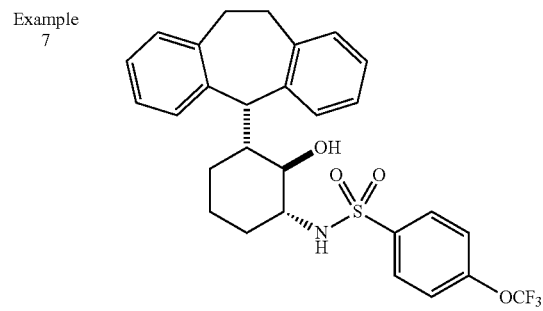 |
| Example 19 | 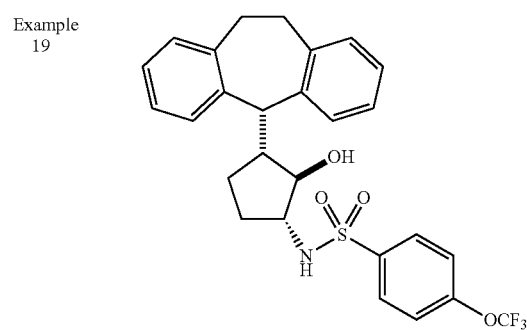 |
| Example 22 | 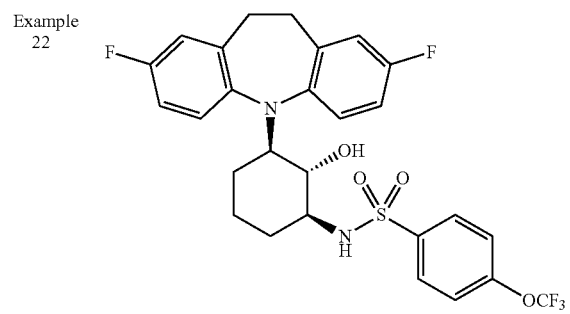 |
| Example 23 | 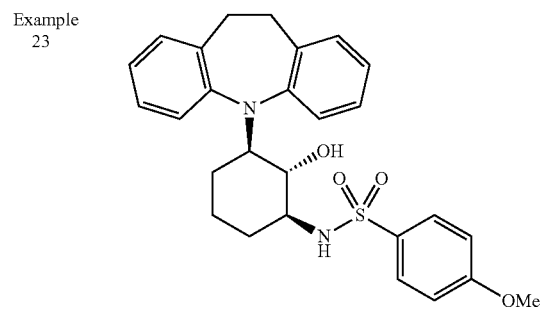 |
| Example 24 | 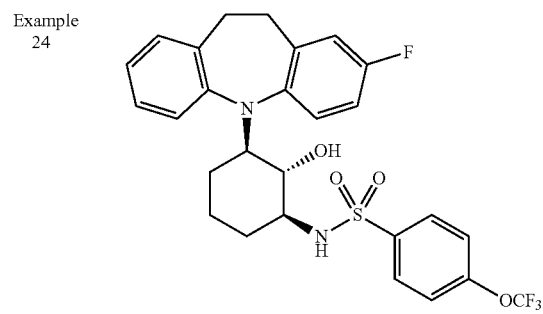 |
| Example No. | Structure |
|---|---|
| Example 25 | 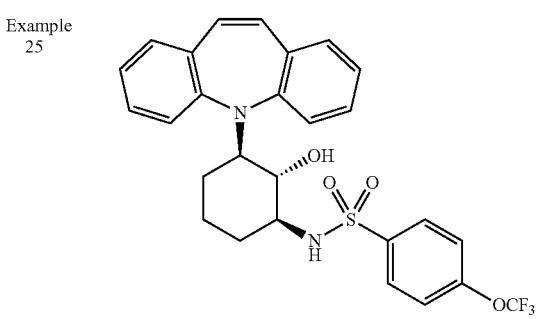 |
| Example 26 | 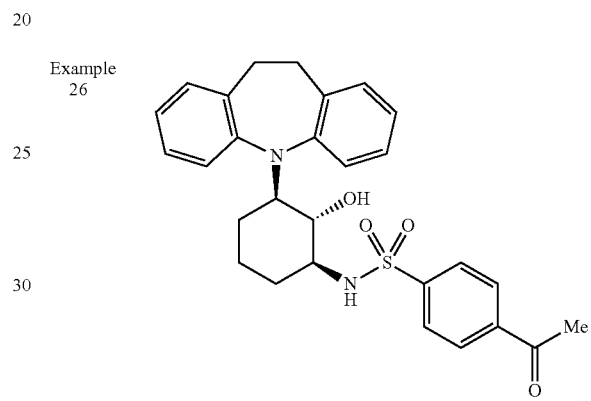 |
| Example 27 | 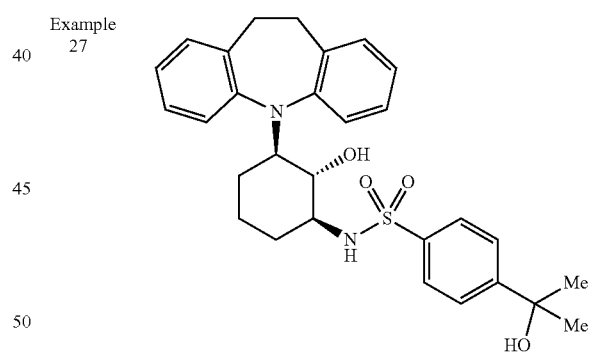 |
| Example 28 | 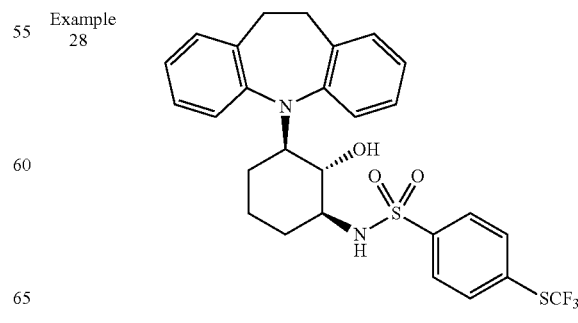 |

-continued
| Example No. | Structure |
|---|---|
| Example 29 | 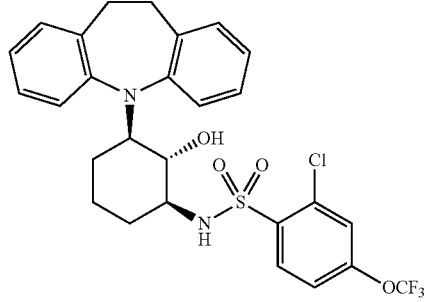 [SMILES: O=S(=O)(N[C@H]1CCC[C@@H](N2c3ccccc3CCc3ccccc32)[C@@H]1O)c1ccc(OC(F)(F)F)cc1Cl] |
| Example 30 | 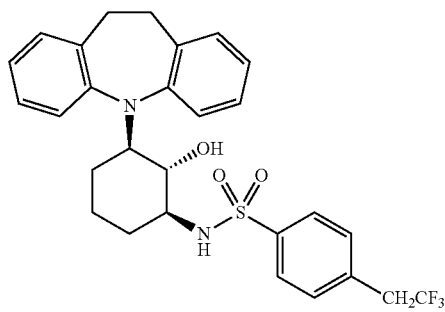 |
| Example 31 | 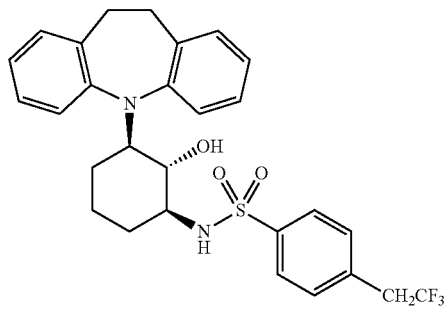 |
-continued
| Example No. | Structure |
|---|---|
| Example 32 | 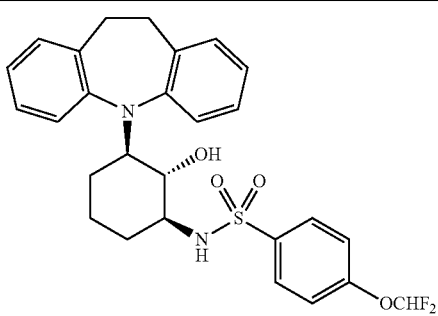 |
| | or |
| Example 33 | 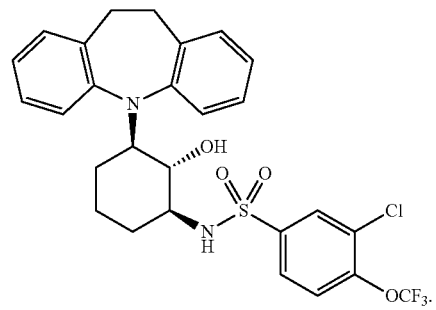 [SMILES: O=S(=O)(N[C@H]1CCC[C@@H](N2c3ccccc3CCc3ccccc32)[C@@H]1O)c1ccc(OC(F)(F)F)c(Cl)c1] |
* * * * *

UNITED STATES PATENT AND TRADEMARK OFFICE
CERTIFICATE OF CORRECTION

PATENT NO. : 9,937,180 B2
APPLICATION NO. : 15/124888
DATED : April 10, 2018
INVENTOR(S) : Ohlmeyer et al.

Page 1 of 1

It is certified that error appears in the above-identified patent and that said Letters Patent is hereby corrected as shown below:

In the Claims

Column 76, Line 12: Claim 11, Delete "-H, -F, -($C_1$-$C_3$)haloalkyl," and insert -- -H, -F, -Cl, -($C_1$-$C_3$)haloalkyl, --

Signed and Sealed this
Twelfth Day of June, 2018

Andrei Iancu
*Director of the United States Patent and Trademark Office*